United States Patent
Lange et al.

(10) Patent No.: US 8,642,587 B2
(45) Date of Patent: Feb. 4, 2014

(54) HETEROCYCLIC COMPOUNDS, PHARMACEUTICAL COMPOSITIONS CONTAINING THEM, AND THEIR USE IN THERAPY

(75) Inventors: Udo Lange, Ludwigshafen (DE); Andreas Heutling, Wiesbaden (DE); Wilhelm Amberg, Wiesbaden (DE); Michael Ochse, Wiesbaden (DE); Berthold Behl, Wiesbaden (DE); Wilfried Hornberger, Wiesbaden (DE); Mario Mezler, Wiesbaden (DE)

(73) Assignee: AbbVie Deutschland GmbH & Co. KG, Wiesbaden (DE)

( * ) Notice: Subject to any disclaimer, the term of this patent is extended or adjusted under 35 U.S.C. 154(b) by 313 days.

(21) Appl. No.: 12/706,321

(22) Filed: Feb. 16, 2010

(65) Prior Publication Data

US 2011/0009378 A1 Jan. 13, 2011

Related U.S. Application Data

(60) Provisional application No. 61/152,822, filed on Feb. 16, 2009.

(51) Int. Cl.
| | | |
|---|---|---|
| A61K 35/55 | (2006.01) | |
| A61K 35/44 | (2006.01) | |
| C07D 421/00 | (2006.01) | |
| C07D 471/00 | (2006.01) | |
| C07D 223/16 | (2006.01) | |

(52) U.S. Cl.
USPC .......... 514/215; 514/300; 514/303; 514/422; 540/593; 546/113; 548/453

(58) Field of Classification Search
USPC ............ 514/215, 300, 303, 422; 540/593; 546/113; 548/453
See application file for complete search history.

(56) References Cited

U.S. PATENT DOCUMENTS

| | | |
|---|---|---|
| 7,189,850 B2 | 3/2007 | Ceccarelli et al. |
| 7,427,612 B2 | 9/2008 | Alberati-Giani et al. |
| 7,462,617 B2 | 12/2008 | Alberati-Giani et al. |
| 2002/0169197 A1 | 11/2002 | Egle et al. |
| 2004/0026364 A1 | 2/2004 | Kihara et al. |
| 2005/0124627 A1 | 6/2005 | Schadt et al. |
| 2005/0153963 A1 | 7/2005 | Dargazanli et al. |
| 2005/0153980 A1 | 7/2005 | Schadt et al. |
| 2005/0159450 A1 | 7/2005 | Dargazanli et al. |
| 2005/0267152 A1 | 12/2005 | Bloomfield et al. |
| 2006/0223802 A1 | 10/2006 | Dargazanli et al. |
| 2006/0223861 A1 | 10/2006 | Dargazanli et al. |
| 2006/0223885 A1 | 10/2006 | Dargazanli et al. |
| 2006/0223886 A1 | 10/2006 | Dargazanli et al. |
| 2007/0155753 A1* | 7/2007 | Ye et al. ............ 514/252.04 |
| 2008/0070941 A1 | 3/2008 | Dargazanli et al. |
| 2008/0119486 A1 | 5/2008 | Jolidon et al. |
| 2011/0105502 A1* | 5/2011 | Amberg et al. ............ 514/235.2 |

FOREIGN PATENT DOCUMENTS

| | | |
|---|---|---|
| EP | 1284257 | 2/2003 |
| WO | 03031435 | 4/2003 |
| WO | 03053942 | 7/2003 |
| WO | 03055478 | 7/2003 |
| WO | 03076420 | 9/2003 |
| WO | 03087086 | 10/2003 |
| WO | 03089411 | 10/2003 |
| WO | 2004013100 | 2/2004 |
| WO | 2004013101 | 2/2004 |
| WO | 2004022528 | 3/2004 |
| WO | 2004072034 | 8/2004 |
| WO | 2004096761 | 11/2004 |
| WO | 2004112787 | 12/2004 |
| WO | 2004113280 | 12/2004 |
| WO | 2004113301 | 12/2004 |
| WO | 2005014563 | 2/2005 |
| WO | 2005023260 | 3/2005 |
| WO | 2005023261 | 3/2005 |
| WO | 2005037781 | 4/2005 |
| WO | 2005037782 | 4/2005 |
| WO | 2005037783 | 4/2005 |
| WO | 2005037785 | 4/2005 |

(Continued)

OTHER PUBLICATIONS

King, F.D. (Ed.), "Bioisosteres, conformational restriction and prodrugs—case history: an example of a conformational restriction approach," Medical Chemistry: Principles and Practice, 1994, Chapter 14, 206-209.*
Lindsley, C.W. et al., Progress Towards Validating the NMDA Receptor Hypofunction Hypothesis of Schizophrenia, Current Topics in Medicinal Chemistry, vol. 6, pp. 771-785 (2006).
Harsing, L.G. et al., Glycine Transporter Type-1 and its Inhibitors, Current Medicinal Chemistry, vol. 13, pp. 1017-1044 (2006).
Hashimoto, Kenji, Glycine Transporter Inhibitors as Therapeutic Agents for Schizophrenia, Recent Patents on CNS Drug Discovery, vol. 1, pp. 43-53 (2006).
Javitt, DC, Glutamate as a therapeutic target in psychiatric disorders, Molecular Psychiatry, vol. 9, pp. 984-997 (2004).
Lindsley, C.W. et al., Progress in the Preparation and Testing of Glycine Transporter Type-1 (GlyT1) Inhibitors, Current Topics in Medicinal Chemistry, vol. 6, pp. 1883-1896 (2006).

*Primary Examiner* — Paul Zarek
(74) *Attorney, Agent, or Firm* — Lisa V. Mueller; Michael Best & Friedrich, LLP

(57) ABSTRACT

The present invention relates to heterocyclic compounds of the formula (I)

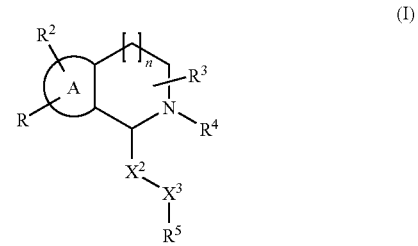

or a physiologically tolerated salt thereof.
The present invention also relates to pharmaceutical compositions comprising such heterocyclic compounds, and the use of such heterocyclic compounds for therapeutic purposes.

19 Claims, No Drawings

(56) References Cited

FOREIGN PATENT DOCUMENTS

| WO | 2005037792 | 4/2005 |
| WO | 2005040166 | 5/2005 |
| WO | 2005046601 | 5/2005 |
| WO | 2005049023 | 6/2005 |
| WO | 2005058317 | 6/2005 |
| WO | 2005058882 | 6/2005 |
| WO | 2005058885 | 6/2005 |

* cited by examiner

HETEROCYCLIC COMPOUNDS, PHARMACEUTICAL COMPOSITIONS CONTAINING THEM, AND THEIR USE IN THERAPY

CROSS-REFERENCE TO RELATED APPLICATIONS

This claims the benefit of U.S. Provisional Patent Application No. 61/152,822, filed on Feb. 16, 2009, the contents of which are incorporated herein by reference.

FIELD OF THE INVENTION

The present invention relates to heterocyclic compounds such as fused tetrahydropyridines, pharmaceutical compositions comprising such heterocyclic compounds, and the use of such heterocyclic compounds for therapeutic purposes.

BACKGROUND OF THE INVENTION

Dysfunction of glutamatergic pathways has been implicated in a number of disease states in the human central nervous system (CNS) including but not limited to schizophrenia, cognitive deficits, dementia, Parkinson disease, Alzheimer disease and bipolar disorder. A large number of studies in animal models lend support to the NMDA hypofunction hypothesis of schizophrenia.

NMDA receptor function can be modulated by altering the availability of the co-agonist glycine. This approach has the critical advantage of maintaining activity-dependent activation of the NMDA receptor because an increase in the synaptic concentration of glycine will not produce an activation of NMDA receptors in the absence of glutamate. Since synaptic glutamate levels are tightly maintained by high affinity transport mechanisms, an increased activation of the glycine site will only enhance the NMDA component of activated synapses.

Two specific glycine transporters, GlyT1 and GlyT2 have been identified and shown to belong to the Na/Cl-dependent family of neurotransmitter transporters which includes taurine, gamma-aminobutyric acid (GABA), proline, monoamines and orphan transporters. GlyT1 and GlyT2 have been isolated from different species and shown to have only 50% identity at the amino acid level. They also have a different pattern of expression in mammalian central nervous system, with GlyT2 being expressed in spinal cord, brainstem and cerebellum and GlyT1 present in these regions as well as forebrain areas such as cortex, hippocampus, septum and thalamus. At the cellular level, GlyT2 has been reported to be expressed by glycinergic nerve endings in rat spinal cord whereas GlyT1 appears to be preferentially expressed by glial cells. These expression studies have led to the suggestion that GlyT2 is predominantly responsible for glycine uptake at glycinergic synapses whereas GlyT1 is involved in monitoring glycine concentration in the vicinity of NMDA receptor expressing synapses. Recent functional studies in rat have shown that blockade of GlyT1 with the potent inhibitor (N-[3-(4'-fluorophenyl)-3-(4'-phenylphenoxy)propyl])-sarcosine (NFPS) potentiates NMDA receptor activity and NMDA receptor-dependent long-term potentiation in rat.

Molecular cloning has further revealed the existence of three variants of GlyT1, termed GlyT-1a, GlyT-1b and GlyT-1c, each of which displays a unique distribution in the brain and peripheral tissues. The variants arise by differential splicing and exon usage, and differ in their N-terminal regions.

The physiological effects of GlyT1 in forebrain regions together with clinical reports showing the beneficial effects of GlyT1 inhibitor sarcosine in improving symptoms in schizophrenia patients suggest that selective GlyT1 inhibitors represent a new class of antipsychotic drugs.

Glycine transporter inhibitors are already known in the art, for example:

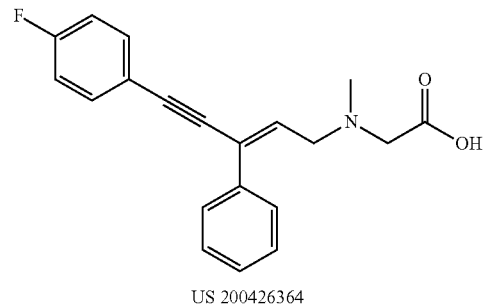

US 200426364

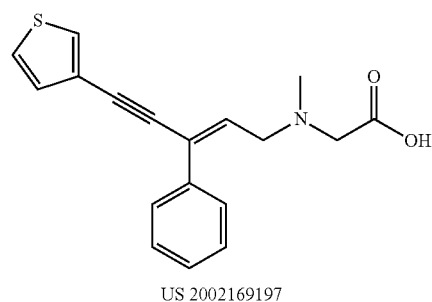

US 2002169197

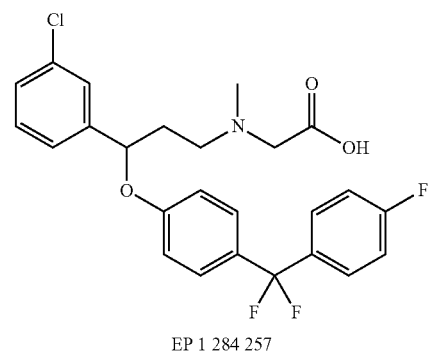

EP 1 284 257

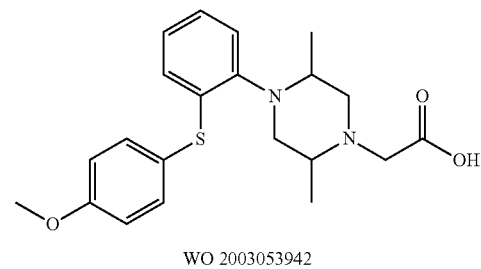

WO 2003053942

3
-continued
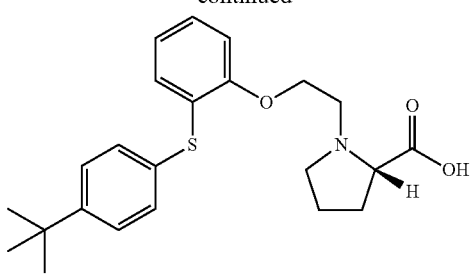
WO 2004096761
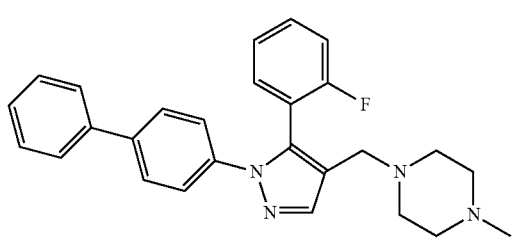
WO 2003031435
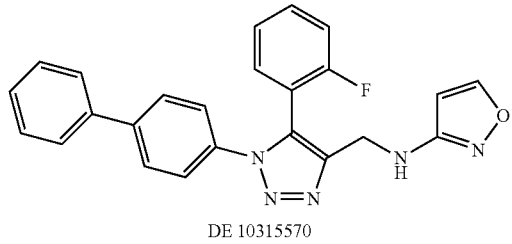
DE 10315570
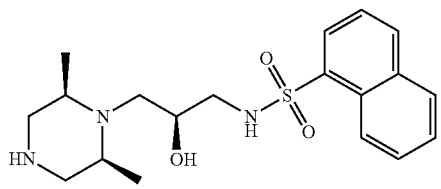
WO 2003055478
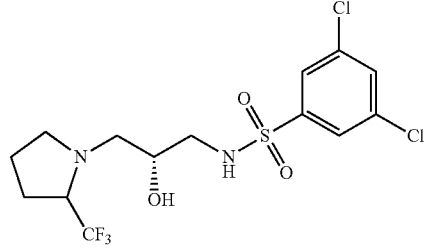
WO 2004113280
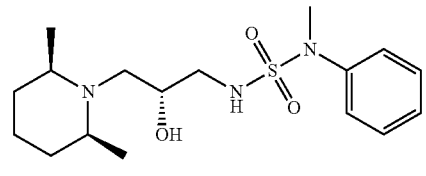
WO 2004112787
4
-continued
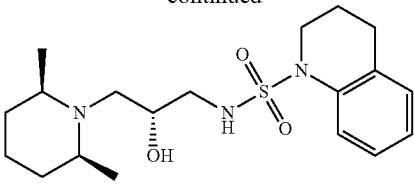
WO 2004113301
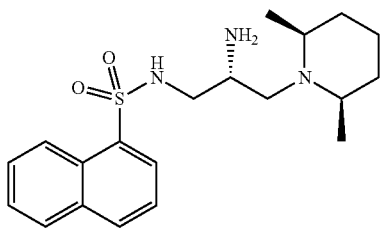
WO 2005049023
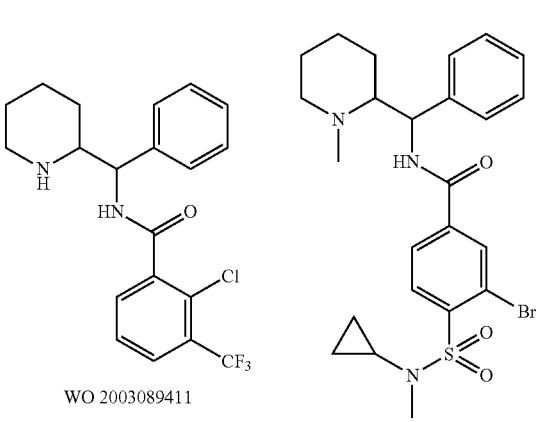
WO 2003089411
WO 2004013100
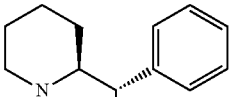
WO 2004013101
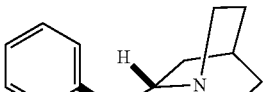
WO 2005037783
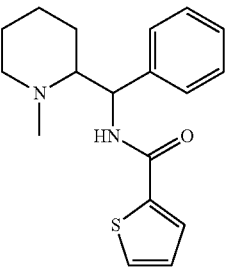
WO 2005037792
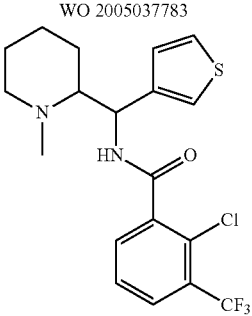
WO 2005037781

-continued
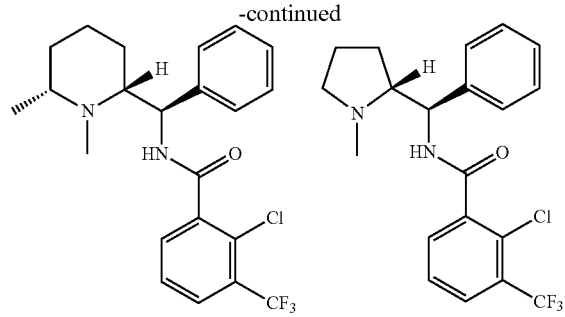
WO 2005037782  WO 2005037785
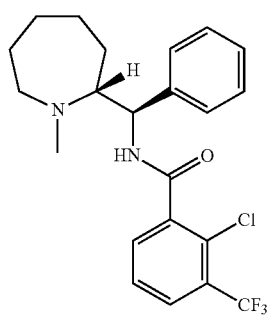
WO 2005037785
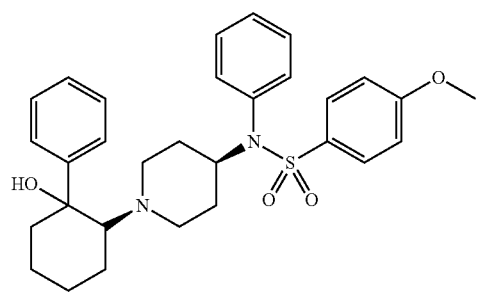
WO 2004072034
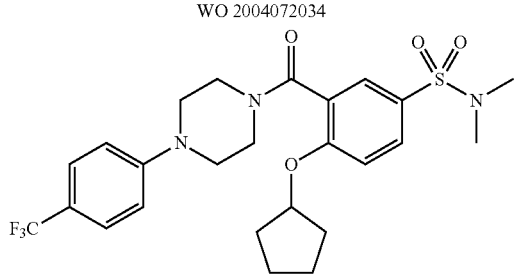
WO 2005014563
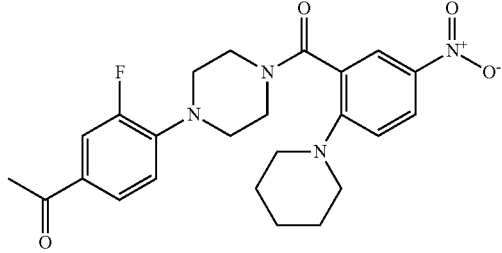
WO 2005023260
-continued
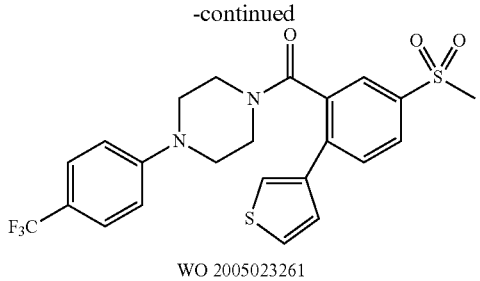
WO 2005023261
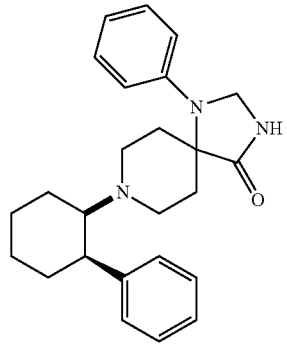
WO 2005040166
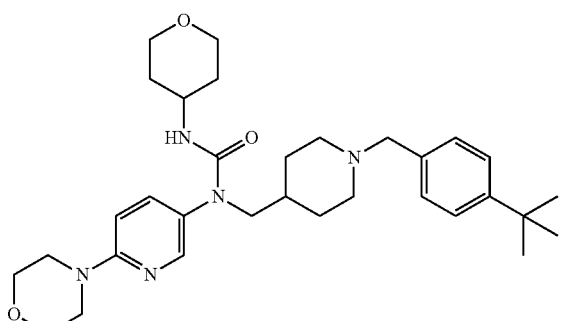
WO 2005058882
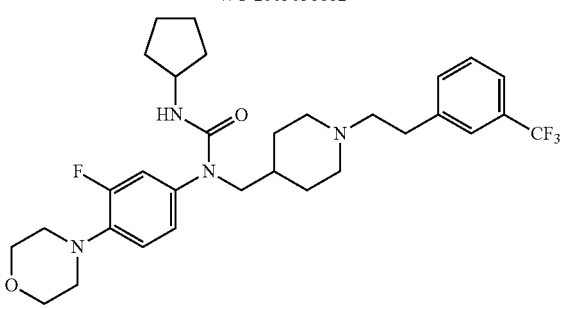
WO 2005058885
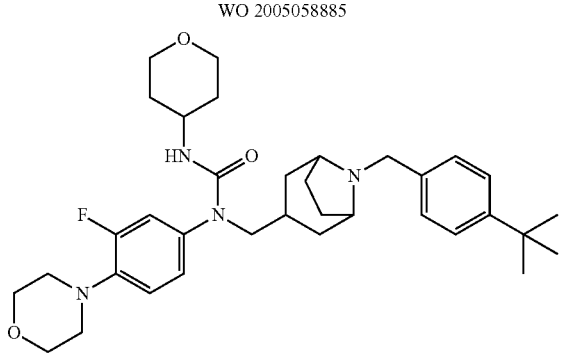
WO 2005058317

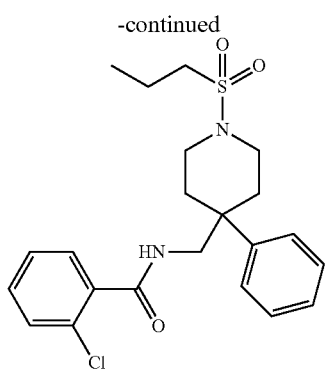

WO 2005046601

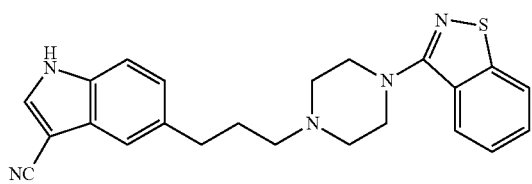

WO 2003087086

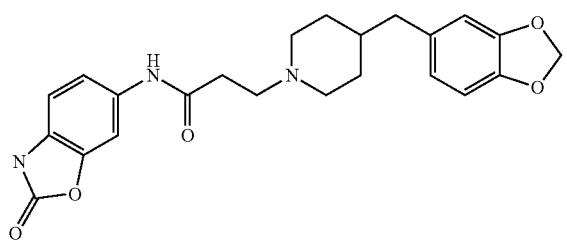

WO 2003076420

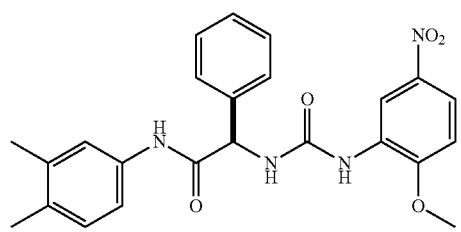

WO 2004022528

(see also Hashimoto K., Recent Patents on CNS Drug Discovery, 2006, 1, 43-53; Harsing L. G. et al., Current Medicinal Chemistry, 2006, 13, 1017-1044; Javitt D. C., Molecular Psychiatry (2004) 9, 984-997; Lindsley, C. W. et al., Current Topics in Medicinal Chemistry, 2006, 6, 771-785; Lindsley C. W. et al., Current Topics in Medicinal Chemistry, 2006, 6, 1883-1896).

It was one object of the present invention to provide further glycine transporter inhibitors.

SUMMARY OF THE INVENTION

The present invention relates to heterocyclic compounds of the formula (I)
wherein

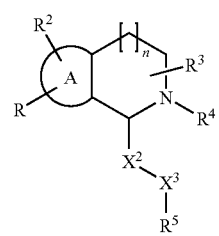

(I)

A is a 5- or 6-membered heterocyclic ring;
R is $R^1$—W-$A^1$-Q-Y-$A^2$-$X^1$—;
$R^1$ is hydrogen, alkyl, cycloalkylalkyl, halogenated alkyl, hydroxyalkyl, alkoxyalkyl, aminoalkyl, alkylaminoalkyl, dialkylaminoalkyl, alkylcarbonylaminoalkyl, alkyloxycarbonylaminoalkyl, alkylaminocarbonylaminoalkyl, dialkylaminocarbonylaminoalkyl, alkylsulfonylaminoalkyl, (optionally substituted arylalkyl)aminoalkyl, optionally substituted arylalkyl, optionally substituted heterocyclylalkyl, cycloalkyl, alkylcarbonyl, alkoxycarbonyl, halogenated alkoxycarbonyl, aryloxycarbonyl, aminocarbonyl, alkylaminocarbonyl, (halogenated alkyl)aminocarbonyl, arylaminocarbonyl, alkenyl, alkynyl, optionally substituted aryl, hydroxy, alkoxy, halogenated alkoxy, hydroxyalkoxy, alkoxyalkoxy, aminoalkoxy, alkylaminoalkoxy, dialkylaminoalkoxy, alkylcarbonylaminoalkoxy, arylcarbonylaminoalkoxy, alkoxycarbonylaminoalkoxy, arylalkoxy, alkylsulfonylaminoalkoxy, (halogenated alkyl)sulfonylaminoalkoxy, arylsulfonylaminoalkoxy, (arylalkyl)sulfonylaminoalkoxy, heterocyclylsulfonylaminoalkoxy, heterocyclylalkoxy, aryloxy, heterocyclyloxy, alkylthio, halogenated alkylthio, alkylamino, (halogenated alkyl)amino, dialkylamino, di-(halogenated alkyl)amino, alkylcarbonylamino, (halogenated alkyl)carbonylamino, arylcarbonylamino, alkylsulfonylamino, (halogenated alkyl)sulfonylamino, arylsulfonylamino or optionally substituted heterocyclyl;
W is —$NR^8$— or a bond;
$A^1$ is optionally substituted alkylene or a bond;
Q is —$S(O)_2$—, —C(O)— or a bond;
Y is —$NR^9$— or a bond;
$A^2$ is optionally substituted alkylene, alkylene-CO—, —CO-alkylene, alkylene-O-alkylene, alkylene-$NR^{10}$-alkylene, optionally substituted alkenylen, optionally substituted alkynylene, optionally substituted arylene, optionally substituted heteroarylene or a bond;
$X^1$ is —O—, —$NR^{11}$—, —S—, optionally substituted alkylene, optionally substituted alkenylen, optionally substituted alkynylene or a bond,
with the proviso that if Q is a bond, W is —$NR^8$— or Y is —$NR^9$—;
$R^2$ is hydrogen, halogen, alkyl, halogenated alkyl, hydroxyalkyl, —CN, alkenyl, alkynyl, optionally substituted aryl, hydroxy, alkoxy, halogenated alkoxy, alkoxycarbonyl, alkenyloxy, arylalkoxy, alkylcarbonyloxy, alkylthio, alkylsulfinyl, alkylsulfonyl, aminosulfonyl, amino, alkylamino, alkenylamino, nitro or optionally substituted heterocyclyl, or two radicals $R^2$ together with the ring atoms of A to which they are bound form an optionally substituted 5- or 6-membered ring;

$R^3$ is hydrogen, halogen, alkyl or alkoxy, or two radicals $R^3$ together with the carbon atom to which they are attached form a carbonyl group;

$R^4$ is hydrogen, alkyl, halogenated alkyl, hydroxyalkyl, alkoxyalkyl, aminoalkyl, $CH_2CN$, —CHO, alkylcarbonyl, (halogenated alkyl)carbonyl, alkoxycarbonyl, arylcarbonyl, alkylaminocarbonyl, alkenyl, —C(=NH)$NH_2$, —C(=NH)NHCN, alkylsulfonyl, arylsulfonyl, amino or heterocyclyl;

$X^2$ is —O—, —$NR^6$—, —S—, >$CR^{12a}R^{12b}$ or a bond;
$X^3$ is —O—, —$NR^7$—, —S—, >$CR^{13a}R^{13b}$ or a bond;
$R^5$ is optionally substituted aryl, optionally substituted cycloalkyl or optionally substituted heterocyclyl;
n is 0, 1, 2;
$R^6$ is hydrogen or alkyl;
$R^7$ is hydrogen or alkyl;
$R^8$ is hydrogen or alkyl;
$R^9$ is hydrogen, alkyl, cycloalkyl, aminoalkyl, optionally substituted arylalkyl or heterocyclyl; or
$R^9, R^1$
together are alkylene; or
$R^9$ is alkylene that is bound to a carbon atom in $A^2$ and $A^2$ is alkylene or to a carbon atom in $X^1$ and $X^1$ is alkylene;
$R^{10}$ is hydrogen, alkyl or alkylsulfonyl;
$R^{11}$ is hydrogen or alkyl, or
$R^9, R^{11}$
together are alkylene,
$R^{12a}$ is hydrogen, optionally substituted alkyl, alkylaminoalkyl, dialkylaminoalkyl, heterocyclylalkyl, optionally substituted aryl or hydroxy;
$R^{12b}$ is hydrogen or alkyl, or
$R^{12a}, R^{12b}$
together are carbonyl or optionally substituted alkylene, wherein one —$CH_2$— of alkylene may be replaced by an oxygen atom or —$NR^{14}$—;
$R^{13a}$ is hydrogen, optionally substituted alkyl, alkylaminoalkyl, dialkylaminoalkyl, heterocyclylalkyl, optionally substituted aryl or hydroxy;
$R^{13b}$ is hydrogen or alkyl, or
$R^{13a}, R^{13b}$
together are carbonyl or optionally substituted alkylene, wherein one —$CH_2$— of alkylene may be replaced by an oxygen atom or —$NR^{15}$—;
$R^{14}$ is hydrogen or alkyl;
$R^{15}$ is hydrogen or alkyl; and
or a physiologically tolerated salt thereof.

Thus, the present invention relates to heterocyclic compounds having the formula (Ia)

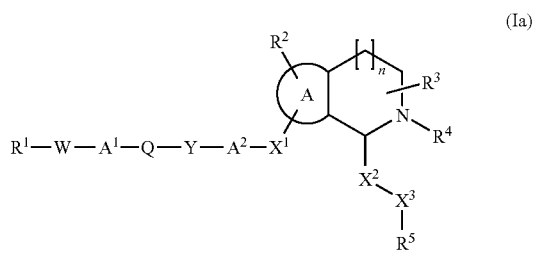

(Ia)

wherein A, $R^1$, W, $A^1$, Q, Y, $A^2$, $X^1$, $R^2$, $R^3$, $R^4$, $X^2$, $X^3$, $R^5$, n are as defined herein.

Further, the present invention relates to heterocyclic compounds of formula (I) wherein R is —CN, i.e. heterocyclic compounds having the formula (Ib)

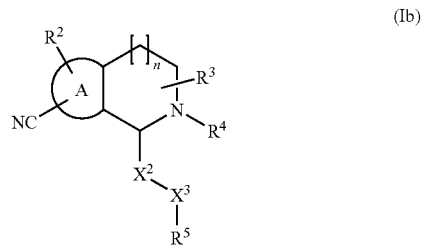

(Ib)

wherein A, $R^2$, $R^3$, $R^4$, $X^2$, $X^3$, $R^5$, n are as defined herein.

Thus, the term heterocyclic compound is used herein to denote in particular tetrahydropyridines (n=1) fused to 5- or 6-membered heterocyclic ring as well as homologous bicyclic compounds wherein n is 0 or 2.

Said compounds of formula (I), i.e., the heterocyclic compounds of formula (I) and their physiologically tolerated acid addition salts, are glycine transporter inhibitors and thus useful as pharmaceuticals.

The present invention thus further relates to the compounds of formula (I) for use in therapy.

The present invention also relates to pharmaceutical compositions which comprise a carrier and a compound of formula (I).

In particular, said compounds, i.e., the heterocyclic compounds and their physiologically tolerated acid addition salts, are inhibitors of the glycine transporter GlyT1.

The present invention thus further relates to the compounds of formula (I) for use in inhibiting the glycine transporter.

The present invention also relates to the use of the compounds of formula (I) in the manufacture of a medicament for inhibiting the glycine transporter GlyT1 and corresponding methods of inhibiting the glycine transporter GlyT1.

Glycine transport inhibitors and in particular inhibitors of the glycine transporter GlyT1 are known to be useful in treating a variety of neurologic and psychiatric disorders.

The present invention thus further relates to the compounds of formula (I) for use in treating a neurologic or psychiatric disorder.

The present invention further relates to the compounds of formula (I) for use in treating pain.

The present invention also relates to the use of the compounds of formula (I) in the manufacture of a medicament for treating a neurologic or psychiatric disorder and corresponding methods of treating said disorders. The present invention also relates to the use of the compounds of formula (I) in the manufacture of a medicament for treating pain and corresponding methods of treating pain.

DETAILED DESCRIPTION

Provided that the heterocyclic compounds of the formula (I) of a given constitution may exist in different spatial arrangements, for example if they possess one or more centers of asymmetry, polysubstituted rings or double bonds, or as different tautomers, it is also possible to use enantiomeric mixtures, in particular racemates, diastereomeric mixtures and tautomeric mixtures, preferably, however, the respective essentially pure enantiomers, diastereomers and tautomers of the compounds of formula (I) and/or of their salts.

According to one embodiment, an enantiomer of the heterocyclic compounds of the present invention has the following formula:

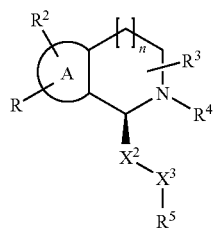

wherein A, R, $R^2$, $R^3$, $X^2$, $X^3$, $R^4$, $R^5$ and n are as defined herein.

According to another embodiment, an enantiomer of the heterocyclic compounds of the present invention has the following formula:

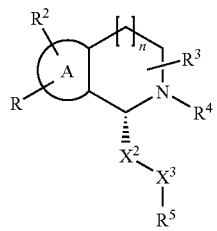

wherein A, R, $R^2$, $R^3$, $X^2$, $X^3$, $R^4$, $R^5$ and n are as defined herein.

The physiologically tolerated salts of the heterocyclic compounds of the formula (I) are especially acid addition salts with physiologically tolerated acids. Examples of suitable physiologically tolerated organic and inorganic acids are hydrochloric acid, hydrobromic acid, phosphoric acid, sulfuric acid, $C_1$-$C_4$-alkylsulfonic acids, such as methanesulfonic acid, cycloaliphatic sulfonic acids, such as S-(+)-10-campher sulfonic acid, aromatic sulfonic acids, such as benzenesulfonic acid and toluenesulfonic acid, di- and tricarboxylic acids and hydroxycarboxylic acids having 2 to 10 carbon atoms, such as oxalic acid, malonic acid, maleic acid, fumaric acid, lactic acid, tartaric acid, citric acid, glycolic acid, adipic acid and benzoic acid. Other utilizable acids are described, e.g., in Fortschritte der Arzneimittelforschung [Advances in drug research], Volume 10, pages 224 ff., Birkhäuser Verlag, Basel and Stuttgart, 1966.

The present invention moreover relates to compounds of formula I as defined herein, wherein at least one of the atoms has been replaced by its stable, non-radioactive isotope (e.g., hydrogen by deuterium, $^{12}C$ by $^{13}C$, $^{14}N$ by $^{15}N$, $^{16}O$ by $^{18}O$) and preferably wherein at least one hydrogen atom has been replaced by a deuterium atom.

Of course, such compounds contain more of the respective isotope than this naturally occurs and thus is anyway present in the compounds I.

Stable isotopes (e.g., deuterium, $^{13}C$, $^{15}N$, $^{18}O$) are nonradioactive isotopes which contain one or more additional neutron than the normally abundant isotope of the respective atom. Deuterated compounds have been used in pharmaceutical research to investigate the in vivo metabolic fate of the compounds by evaluation of the mechanism of action and metabolic pathway of the non deuterated parent compound (Blake et al. J. Pharm. Sci. 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., J. Labelled Comp. Radiopharmaceut., 36(10):927-932 (1995); Kushner et al., Can. J. Physiol. Pharmacol., 77, 79-88 (1999).

Incorporation of a heavy atom particularly substitution of deuterium for hydrogen, can give rise to an isotope effect that could alter the pharmacokinetics of the drug. This effect is usually insignificant if the label is placed at a metabolically inert position of the molecule.

Stable isotope labeling of a drug can alter its physicochemical properties such as pKa and lipid solubility. These changes may influence the fate of the drug at different steps along its passage through the body. Absorption, distribution, metabolism or excretion can be changed. Absorption and distribution are processes that depend primarily on the molecular size and the lipophilicity of the substance. These effects and alterations can affect the pharmacodynamic response of the drug molecule if the isotopic substitution affects a region involved in a ligand-receptor interaction.

Drug metabolism can give rise to large isotopic effect if the breaking of a chemical bond to a deuterium atom is the rate limiting step in the process. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. In any reaction in which the breaking of this bond is the rate limiting step, the reaction will proceed slower for the molecule with the heavy isotope due to "kinetic isotope effect". A reaction involving breaking a C-D bond can be up to 700 percent slower than a similar reaction involving breaking a C—H bond. If the C-D bond is not involved in any of the steps leading to the metabolite, there may not be any effect to alter the behavior of the drug. If a deuterium is placed at a site involved in the metabolism of a drug, an isotope effect will be observed only if breaking of the C-D bond is the rate limiting step. There is evidence to suggest that whenever cleavage of an aliphatic C—H bond occurs, usually by oxidation catalyzed by a mixed-function oxidase, replacement of the hydrogen by deuterium will lead to observable isotope effect. It is also important to understand that the incorporation of deuterium at the site of metabolism slows its rate to the point where another metabolite produced by attack at a carbon atom not substituted by deuterium becomes the major pathway a process called "metabolic switching".

Deuterium tracers, such as deuterium-labeled drugs and doses, in some cases repeatedly, of thousands of milligrams of deuterated water, are also used in healthy humans of all ages, including neonates and pregnant women, without reported incident (e.g. Pons G and Rey E, Pediatrics 1999 104: 633; Coward W A et al., Lancet 1979 7: 13; Schwarcz H P, Control. Clin. Trials 1984 5(4 Suppl): 573; Rodewald L E et al., J. Pediatr. 1989 114: 885; Butte N F et al. Br. J. Nutr. 1991 65: 3; MacLennan A H et al. Am. J. Obstet. Gynecol. 1981 139: 948). Thus, it is clear that any deuterium released, for instance, during the metabolism of compounds of this invention poses no health risk.

The weight percentage of hydrogen in a mammal (approximately 9%) and natural abundance of deuterium (approximately 0.015%) indicates that a 70 kg human normally contains nearly a gram of deuterium. Furthermore, replacement of up to about 15% of normal hydrogen with deuterium has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci. 1960 84: 736; Czakja D M et al., Am. J. Physiol. 1961 201: 357). Higher deuterium concentrations, usually in excess of 20%, can be toxic in animals. However, acute replacement of as high as 15%-23% of the hydrogen in humans' fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Increasing the amount of deuterium present in a compound above its natural abundance is called enrichment or deuterium-enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %.

The hydrogens present on a particular organic compound have different capacities for exchange with deuterium. Certain hydrogen atoms are easily exchangeable under physiological conditions and, if replaced by deuterium atoms, it is expected that they will readily exchange for protons after administration to a patient. Certain hydrogen atoms may be exchanged for deuterium atoms by the action of a deuteric acid such as $D_2SO_4/D_2O$. Alternatively, deuterium atoms may be incorporated in various combinations during the synthesis of compounds of the invention. Certain hydrogen atoms are not easily exchangeable for deuterium atoms. However, deuterium atoms at the remaining positions may be incorporated by the use of deuterated starting materials or intermediates during the construction of compounds of the invention.

Deuterated and deuterium-enriched compounds of the invention can be prepared by using known methods described in the literature. Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure. Relevant procedures and intermediates are disclosed, for instance in Lizondo, J et al., *Drugs Fut,* 21(11), 1116 (1996); Brickner, S J et al., *J Med Chem,* 39(3), 673 (1996); Mallesham, B et al., *Org Lett,* 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; 20090082471, the methods are hereby incorporated by reference.

The organic moieties mentioned in the above definitions of the variables are—like the term halogen—collective terms for individual listings of the individual group members. The prefix $C_n$—$C_m$ indicates in each case the possible number of carbon atoms in the group.

Unless indicated otherwise, the term "substituted" means that a radical is substituted with 1, 2 or 3, especially 1, substituent which are in particular selected from the group consisting of halogen, $C_1$-$C_4$-alkyl, hydroxy-$C_1$-$C_4$-alkyl, $C_3$-$C_{12}$-heterocyclyl-alkyl, $C_1$-$C_4$-alkoxy-$C_1$-$C_4$-alkyl, amino-$C_1$-$C_4$-alkyl, $C_1$-$C_4$-alkenyl, OH, SH, CN, $CF_3$, O—$CF_3$, COOH, O—$CH_2$—COOH, $C_1$-$C_6$-alkoxy, $C_1$-$C_6$-alkylthio, $C_3$-$C_7$-cycloalkyl, COO—$C_1$-$C_6$-alkyl, $CONH_2$, CONH—$C_1$-$C_6$-alkyl, $SO_2NH$—$C_1$-$C_6$-alkyl, CON—($C_1$-$C_6$-alkyl)$_2$, $SO_2N$—($C_1$-$C_6$-alkyl)$_2$, $NH_2$, NH—$C_1$-$C_6$-alkyl, N—($C_1$-$C_6$-alkyl)$_2$, NH—($C_1$-$C_4$-alkyl-$C_6$-$C_{12}$-aryl), NH—CO—$C_1$-$C_6$-alkyl, NH—$SO_2$—$C_1$-$C_6$-alkyl, $SO_2$—$C_1$-$C_6$-alkyl, $C_6$-$C_{12}$-aryl, O—$C_6$-$C_{12}$-aryl, O—$CH_2$—$C_6$-$C_{12}$-aryl, CONH—$C_6$-$C_{12}$-aryl, $SO_2NH$—$C_6$-$C_{12}$-aryl, CONH—$C_3$-$C_{12}$-heterocyclyl, $SO_2NH$—$C_3$-$C_{12}$-heterocyclyl, $SO_2$—$C_6$-$C_{12}$-aryl, NH—$SO_2$—$C_6$-$C_{12}$-aryl, NH—CO—$C_6$-$C_{12}$-aryl, NH—$SO_2$—$C_3$-$C_{12}$-heterocyclyl, NH—CO—$C_3$-$C_{12}$-heterocyclyl and $C_3$-$C_{12}$-heterocyclyl, wherein aryl and heterocyclyl in turn may be unsubstituted or substituted with 1, 2 or 3 substituents selected from the group consisting of halogen, $C_1$-$C_4$-alkyl, $C_1$-$C_4$-haloalkyl, $C_1$-$C_4$-alkoxy and $C_1$-$C_4$-haloalkoxy.

The term halogen denotes in each case fluorine, bromine, chlorine or iodine, in particular fluorine or chlorine.

$C_1$-$C_4$-Alkyl is a straight-chain or branched alkyl group having from 1 to 4 carbon atoms. Examples of an alkyl group are methyl, $C_2$-$C_4$-alkyl such as ethyl, n-propyl, iso-propyl, n-butyl, 2-butyl, iso-butyl or tert-butyl. $C_1$-$C_2$-Alkyl is methyl or ethyl, $C_1$-$C_3$-alkyl is additionally n-propyl or iso-propyl.

$C_1$-$C_6$-Alkyl is a straight-chain or branched alkyl group having from 1 to 6 carbon atoms. Examples include methyl, $C_2$-$C_4$-alkyl as mentioned herein and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

Halogenated $C_1$-$C_4$-alkyl is a straight-chain or branched alkyl group having 1 to 4 carbon atoms, preferably 1 to 3 carbon atoms, more preferably 1 or 2 carbon atoms, wherein at least one, e.g. 1, 2, 3, 4 or all of the hydrogen atoms are replaced by 1, 2, 3, 4 or a corresponding number of identical or different halogen atoms, such as in halogenomethyl, dihalogenomethyl, trihalogenomethyl, (R)-1-halogenoethyl, (S)-1-halogenoethyl, 2-halogenoethyl, 1,1-dihalogenoethyl, 2,2-dihalogenoethyl, 2,2,2-trihalogenoethyl, (R)-1-halogenopropyl, (S)-1-halogenopropyl, 2-halogenopropyl, 3-halogenopropyl, 1,1-dihalogenopropyl, 2,2-dihalogenopropyl, 3,3-dihalogenopropyl, 3,3,3-trihalogenopropyl, (R)-2-halogeno-1-methylethyl, (S)-2-halogeno-1-methylethyl, (R)-2,2-dihalogeno-1-methylethyl, (S)-2,2-dihalogeno-1-methylethyl, (R)-1,2-dihalogeno-1-methylethyl, (S)-1,2-dihalogeno-1-methylethyl, (R)-2,2,2-trihalogeno-1-methylethyl, (S)-2,2,2-trihalogeno-1-methylethyl, 2-halogeno-1-(halogenomethyl)ethyl, 1-(dihalogenomethyl)-2,2-dihalogenoethyl, (R)-1-halogenobutyl, (S)-1-halogenobutyl, 2-halogenobutyl, 3-halogenobutyl, 4-halogenobutyl, 1,1-dihalogenobutyl, 2,2-dihalogenobutyl, 3,3-dihalogenobutyl, 4,4-dihalogenobutyl, 4,4,4-trihalogenobutyl, etc. Particular examples include the fluorinated $C_1$-$C_4$ alkyl groups as defined, such as trifluoromethyl.

$C_6$-$C_{12}$-Aryl-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by $C_6$-$C_{12}$-aryl, such as in benzyl.

Hydroxy-$C_1$-$C_4$-alkyl is a straight-chain or branched alkyl group having 1 to 4 carbon atoms, preferably 1 to 3 carbon atoms, more preferably 1 or 2 carbon atoms, wherein one or two hydrogen atoms are replaced by one or two hydroxyl groups, such as in hydroxymethyl, (R)-1-hydroxyethyl, (S)-

1-hydroxyethyl, 2-hydroxyethyl, (R)-1-hydroxypropyl, (S)-1-hydroxypropyl, 2-hydroxypropyl, 3-hydroxypropyl, (R)-2-hydroxy-1-methylethyl, (S)-2-hydroxy-1-methylethyl, 2-hydroxy-1-(hydroxymethyl)ethyl, (R)-1-hydroxybutyl, (S)-1-hydroxybutyl, 2-hydroxybutyl, 3-hydroxybutyl, 4-hydroxybutyl.

$C_1$-$C_6$-Alkoxy-$C_1$-$C_4$-alkyl is a straight-chain or branched alkyl group having 1 to 4 carbon atoms, preferably 1 to 3 carbon atoms, more preferably 1 or 2 carbon atoms, wherein one or two hydrogen atoms are replaced by one or two alkoxy groups having 1 to 6, preferably 1 to 4, in particular 1 or 2 carbon atoms, such as in methoxymethyl, (R)-1-methoxyethyl, (S)-1-methoxyethyl, 2-methoxyethyl, (R)-1-methoxypropyl, (S)-1-methoxypropyl, 2-methoxypropyl, 3-methoxypropyl, (R)-2-methoxy-1-methylethyl, (S)-2-methoxy-1-methylethyl, 2-methoxy-1-(methoxymethyl)ethyl, (R)-1-methoxybutyl, (S)-1-methoxybutyl, 2-methoxybutyl, 3-methoxybutyl, 4-methoxybutyl, ethoxymethyl, (R)-1-ethoxyethyl, (S)-1-ethoxyethyl, 2-ethoxyethyl, (R)-1-ethoxypropyl, (S)-1-ethoxypropyl, 2-ethoxypropyl, 3-ethoxypropyl, (R)-2-ethoxy-1-methylethyl, (S)-2-ethoxy-1-methylethyl, 2-ethoxy-1-(ethoxymethyl)ethyl, (R)-1-ethoxybutyl, (S)-1-ethoxybutyl, 2-ethoxybutyl, 3-ethoxybutyl, 4-ethoxybutyl.

Amino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by an amino group, such as in amino methyl, 2-aminoethyl.

$C_1$-$C_6$-Alkylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a $C_1$-$C_6$-alkylamino group, in particular by a $C_1$-$C_4$-alkylamino group, such as in methylaminomethyl, ethylaminomethyl, n-propylaminomethyl, iso-propylaminomethyl, n-butylaminomethyl, 2-butylaminomethyl, iso-butylaminomethyl or tert-butylaminomethyl.

Di-$C_1$-$C_6$-Alkylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a di-$C_1$-$C_6$-Alkylamino group, in particular by a di-$C_1$-$C_4$-alkylamino group, such as in dimethylaminomethyl.

$C_1$-$C_6$-Alkylcarbonylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a $C_1$-$C_6$-alkylcarbonylamino group, in particular by a $C_1$-$C_4$-alkylcarbonylamino group, such as in methylcarbonylaminomethyl, ethylcarbonylaminomethyl, n-propylcarbonylaminomethyl, iso-propylcarbonylaminomethyl, n-butylcarbonylaminomethyl, 2-butylcarbonylaminomethyl, iso-butylcarbonylaminomethyl or tert-butylcarbonylaminomethyl.

$C_1$-$C_6$-Alkylaminocarbonylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a $C_1$-$C_6$-alkylaminocarbonylamino group, in particular by a $C_1$-$C_4$-alkylaminocarbonylamino group, such as in methylaminocarbonylaminomethyl, ethylaminocarbonylaminomethyl, n-propylaminocarbonylaminomethyl, iso-propylaminocarbonylaminomethyl, n-butylaminocarbonylaminomethyl, 2-butylaminocarbonylaminomethyl, iso-butylaminocarbonylaminomethyl or tert-butylaminocarbonylaminomethyl.

Di-$C_1$-$C_6$-alkylaminocarbonylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a di-$C_1$-$C_6$-alkylaminocarbonylamino group, in particular by a di-$C_1$-$C_4$-alkylaminocarbonylamino group, such as in dimethylaminocarbonylaminomethyl, dimethylaminocarbonylaminoethyl, dimethylaminocarbonylaminon-propyl.

$C_1$-$C_6$-Alkylsulfonylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a $C_1$-$C_6$-alkylsulfonylamino group, in particular by a $C_1$-$C_4$-alkylsulfonylamino group, such as in methylsulfonylaminomethyl, ethylsulfonylaminomethyl, n-propylsulfonylaminomethyl, iso-propylsulfonylaminomethyl, n-butylsulfonylaminomethyl, 2-butylsulfonylaminomethyl, iso-butylsulfonylaminomethyl or tert-butylsulfonylaminomethyl.

($C_6$-$C_{12}$-Aryl-$C_1$-$C_6$-alkyl)amino-$C_1$-$C_4$ alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a ($C_6$-$C_{12}$-aryl-$C_1$-$C_6$-alkyl)amino group, in particular a ($C_6$-$C_{12}$-aryl-$C_1$-$C_2$-alkyl) amino group, such as in benzylaminomethyl.

$C_3$-$C_{12}$-Heterocyclyl-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by $C_3$-$C_{12}$-heterocyclyl, such as in N-pyrrolidinylmethyl, N-piperidinylmethyl, N-morpholinylmethyl.

$C_3$-$C_{12}$-Cycloalkyl is a cycloaliphatic radical having from 3 to 12 carbon atoms. In particular, 3 to 6 carbon atoms form the cyclic structure, such as cyclopropyl, cyclobutyl, cyclopentyl and cyclohexyl. The cyclic structure may be unsubstituted or may carry 1, 2, 3 or 4 $C_1$-$C_4$ alkyl radicals, preferably one or more methyl radicals.

Carbonyl is >C=O.

$C_1$-$C_6$-Alkylcarbonyl is a radical of the formula R—C(O)—, wherein R is an alkyl radical having from 1 to 6, preferably from 1 to 4, in particular 1 or 2 carbon atoms as defined herein. Examples include acetyl, propionyl, n-butyryl, 2-methylpropionyl, pivaloyl.

Halogenated $C_1$-$C_6$-alkylcarbonyl is $C_1$-$C_6$-alkylcarbonyl as defined herein, wherein at least one, e.g. 1, 2, 3, 4 or all of the hydrogen atoms are replaced by 1, 2, 3, 4 or a corresponding number of identical or different halogen atoms. Examples include fluoromethylcarbonyl, difluoromethylcarbonyl, trifluoromethylcarbonyl. Further examples are 1,1,1-trifluoroeth-2-ylcarbonyl, 1,1,1-trifluoroprop-3-ylcarbonyl.

$C_6$-$C_{12}$-Arylcarbonyl is a radical of the formula R—C(O)—, wherein R is an aryl radical having from 6 to 12 carbon atoms as defined herein. Examples include benzoyl.

$C_1$-$C_6$-Alkoxycarbonyl is a radical of the formula R—O—C(O)—, wherein R is an alkyl radical having from 1 to 6, preferably from 1 to 4, in particular 1 or 2 carbon atoms as defined herein. Examples include methoxycarbonyl and tert-butyloxycarbonyl.

Halogenated $C_1$-$C_6$-alkoxycarbonyl is a $C_1$-$C_6$-alkoxycarbonyl as defined herein, wherein at least one, e.g. 1, 2, 3, 4 or all of the hydrogen atoms are replaced by 1, 2, 3, 4 or a corresponding number of identical or different halogen atoms.

$C_6$-$C_{12}$-Aryloxycarbonyl is a radical of the formula R—O—C(O)—, wherein R is an aryl radical having from 6 to 12 carbon atoms as defined herein. Examples include phenoxycarbonyl.

Cyano is —C≡N.

Aminocarbonyl is $NH_2C(O)$—.

$C_1$-$C_6$-Alkylaminocarbonyl is a radical of the formula R—NH—C(O)—, wherein R is an alkyl radical having from 1 to 6, preferably from 1 to 4, in particular 1 or 2 carbon atoms as defined herein. Examples include methylaminocarbonyl.

(Halogenated $C_1$-$C_4$-alkyl)aminocarbonyl is a $C_1$-$C_4$-alkylaminocarbonyl as defined herein, wherein at least one, e.g. 1, 2, 3, 4 or all of the hydrogen atoms are replaced by 1, 2, 3, 4 or a corresponding number of identical or different hydrogen atoms.

$C_6$-$C_{12}$-Arylaminocarbonyl is a radical of the formula R—NH—C(O)—, wherein R is an aryl radical having from 6 to 12 carbon atoms as defined herein. Examples include phenylaminocarbonyl.

$C_2$-$C_6$-Alkenyl is a singly unsaturated hydrocarbon radical having 2, 3, 4, 5 or 6 carbon atoms, e.g. vinyl, allyl (2-propen-1-yl), 1-propen-1-yl, 2-propen-2-yl, methallyl(2-methylprop-2-en-1-yl) and the like. $C_3$-$C_5$-Alkenyl is, in particular, allyl, 1-methylprop-2-en-1-yl, 2-buten-1-yl, 3-buten-1-yl, methallyl, 2-penten-1-yl, 3-penten-1-yl, 4-penten-1-yl, 1-methylbut-2-en-1-yl or 2-ethylprop-2-en-1-yl.

$C_2$-$C_6$-Alkynyl is a singly unsaturated hydrocarbon radical having 2, 3, 4, 5 or 6 carbon atoms, e.g. ethynyl, 2-propyn-1-yl, 1-propyn-1-yl, 2-propyn-2-yl and the like. $C_3$-$C_5$-Alkynyl is, in particular, 2-propyn-1-yl, 2-butyn-1-yl, 3-butyn-1-yl, 2-pentyn-1-yl, 3-pentyn-1-yl, 4-pentyn-1-yl.

$C_1$-$C_4$-Alkylene is straight-chain or branched alkylene group having from 1 to 4 carbon atoms. Examples include methylene and ethylene. A further example is propylene.

$C_2$-$C_4$-Alkenylene is straight-chain or branched alkenylene group having from 2 to 4 carbon atoms.

$C_2$-$C_4$-Alkynylene is straight-chain or branched alkynylene group having from 2 to 4 carbon atoms. Examples include propynylene.

$C_6$-$C_{12}$-Aryl is a 6- to 12-membered, in particular 6- to 10-membered, aromatic cyclic radical. Examples include phenyl and naphthyl.

$C_3$-$C_{12}$-Arylene is an aryl diradical. Examples include phen-1,4-ylene and phen-1,3-ylene.

Hydroxy is —OH.

$C_1$-$C_6$-Alkoxy is a radical of the formula R—O—, wherein R is a straight-chain or branched alkyl group having from 1 to 6, in particular 1 to 4 carbon atoms. Examples include methoxy, ethoxy, n-propoxy, isopropoxy, n-butoxy, 2-butoxy, isobutoxy (2-methylpropoxy), tert.-butoxy pentyloxy, 1-methylbutoxy, 2-methylbutoxy, 3-methylbutoxy, 2,2-dimethylpropoxy, 1-ethylpropoxy, hexyloxy, 1,1-dimethylpropoxy, 1,2-dimethylpropoxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethylbutyloxy, 2-ethylbutyloxy, 1,1,2-trimethylpropoxy, 1,2,2-trimethylpropoxy, 1-ethyl-1-methylpropoxy and 1-ethyl-2-methylpropoxy.

Halogenated $C_1$-$C_6$-alkoxy is a straight-chain or branched alkoxy group having from 1 to 6, preferably from 1 to 4, in particular 1 or 2 carbon atoms, wherein at least one, e.g. 1, 2, 3, 4 or all of the hydrogen atoms are replaced by 1, 2, 3, 4 or a corresponding number of identical or different halogen atoms, such as in halogenomethoxy, dihalogenomethoxy, trihalogenomethoxy, (R)-1-halogenoethoxy, (S)-1-halogenoethoxy, 2-halogenoethoxy, 1,1-dihalogenoethoxy, 2,2-dihalogenoethoxy, 2,2,2-trihalogenoethoxy, (R)-1-halogenopropoxy, (S)-1-halogenopropoxy, 2-halogenopropoxy, 3-halogenopropoxy, 1,1-dihalogenopropoxy, 2,2-dihalogenopropoxy, 3,3-dihalogenopropoxy, 3,3,3-trihalogenopropoxy, (R)-2-halogeno-1-methylethoxy, (S)-2-halogeno-1-methylethoxy, (R)-2,2-dihalogeno-1-methylethoxy, (S)-2,2-dihalogeno-1-methylethoxy, (R)-1,2-dihalogeno-1-methylethoxy, (S)-1,2-dihalogeno-1-methylethoxy, (R)-2,2,2-trihalogeno-1-methylethoxy, (S)-2,2,2-trihalogeno-1-methylethoxy, 2-halogeno-1-(halogenomethyl)ethoxy, 1-(dihalogenomethyl)-2,2-dihalogenoethoxy, (R)-1-halogenobutoxy, (S)-1-halogenobutoxy, 2-halogenobutoxy, 3-halogenobutoxy, 4-halogenobutoxy, 1,1-dihalogenobutoxy, 2,2-dihalogenobutoxy, 3,3-dihalogenobutoxy, 4,4-dihalogenobutoxy, 4,4,4-trihalogenobutoxy, etc. Particular examples include the fluorinated $C_1$-$C_4$ alkoxy groups as defined, such as trifluoromethoxy.

$C_1$-$C_6$-Hydroxyalkoxy is an alkoxy radical having from 1 to 6, preferably from 1 to 4 carbon atoms as defined herein, wherein one or two hydrogen atoms are replaced by hydroxy. Examples include 2-hydroxyethoxy, 3-hydroxypropoxy, 2-hydroxypropoxy, 1-methyl-2-hydroxyethoxy and the like.

$C_1$-$C_6$-Alkoxy-$C_1$-$C_4$-alkoxy is an alkoxy radical having from 1 to 4 carbon atoms, preferably 1 or 2 carbon atoms as defined herein, wherein one or two hydrogen atoms are replaced by one or two alkoxy radicals having from 1 to 6, preferably from 1 to 4 carbon atoms as defined herein. Examples include methoxymethoxy, 2-methoxyethoxy, 1-methoxyethoxy, 3-methoxypropoxy, 2-methoxypropoxy, 1-methyl-1-methoxyethoxy, ethoxymethoxy, 2-ethoxyethoxy, 1-ethoxyethoxy, 3-ethoxypropoxy, 2-ethoxypropoxy, 1-methyl-1-ethoxyethoxy and the like.

Amino-$C_1$-$C_4$-alkoxy is an alkoxy radical having from 1 to 4, preferably 1 or 2 carbon atoms as defined herein, wherein one hydrogen atom is replaced by an amino group. Examples include 2-aminoethoxy.

$C_1$-$C_6$-Alkylamino-$C_1$-$C_4$-alkoxy is an alkoxy radical having from 1 to 4, preferably 1 or 2 carbon atoms as defined herein, wherein one hydrogen atom is replaced by an alkylamino group having from 1 to 6, preferably from 1 to 4 carbon atoms as defined herein. Examples include methylaminomethoxy, ethylaminomethoxy, n-propylaminomethoxy, iso-propylaminomethoxy, n-butylaminomethoxy, 2-butylaminomethoxy, iso-butylaminomethoxy, tert-butylaminomethoxy, 2-(methylamino)ethoxy, 2-(ethylamino)ethoxy, 2-(n-propylamino)ethoxy, 2-(iso-propylamino)ethoxy, 2-(n-butylamino)ethoxy, 2-(2-butylamino)ethoxy, 2-(iso-butylamino)ethoxy, 2-(tert-butylamino)ethoxy.

Di-$C_1$-$C_6$-alkylamino-$C_1$-$C_4$-alkoxy is an alkoxy radical having from 1 to 4, preferably 1 or 2 carbon atoms as defined herein, wherein one hydrogen atom is replaced by a dialkylamino group having from 1 to 6, preferably from 1 to 4 carbon atoms as defined herein. Examples include dimethylaminomethoxy, diethylaminomethoxy, N-methyl-N-ethylamino)ethoxy, 2-(dimethylamino)ethoxy, 2-(diethylamino)ethoxy, 2-(N-methyl-N-ethylamino)ethoxy.

$C_1$-$C_6$-Alkylcarbonylamino-$C_1$-$C_4$-alkoxy is an alkoxy radical having from 1 to 4, preferably 1 or 2 carbon atoms as defined herein, wherein one hydrogen atom is replaced by an alkylcarbonylamino group wherein the alkyl group has from 1 to 6, preferably from 1 to 4 carbon atoms as defined herein. Examples include methylcarbonylaminomethoxy, ethylcarbonylaminomethoxy, n-propylcarbonylaminomethoxy, iso-propylcarbonylaminomethoxy, n-butylcarbonylaminomethoxy, 2-butylcarbonylaminomethoxy, isobutylcarbonylaminomethoxy, tert-butylcarbonylaminomethoxy, 2-(methylcarbonylamino)ethoxy, 2-(ethylcarbonylamino)ethoxy, 2-(n-propylcarbonylamino)ethoxy, 2-(iso-propylcarbonylamino)ethoxy, 2-(n-butylcarbonylamino)ethoxy, 2-(2-butylcarbonylamino)ethoxy, 2-(iso-butylcarbonylamino)ethoxy, 2-(tert-butylcarbonylamino)ethoxy.

$C_6$-$C_{12}$-Arylcarbonylamino-$C_1$-$C_4$-alkoxy is an alkoxy radical having from 1 to 4, preferably 1 or 2 carbon atoms as defined herein, wherein one hydrogen atom is replaced by a $C_6$-$C_{12}$-arylcarbonylamino group as defined herein. Examples include 2-(benzoylamino)ethoxy.

$C_1$-$C_6$-Alkoxycarbonylamino-$C_1$-$C_4$-alkoxy is an alkoxy radical having from 1 to 4, preferably 1 or 2 carbon atoms as defined herein, wherein one hydrogen atom is replaced by an alkoxycarbonylamino group wherein the alkoxy group has from 1 to 6, preferably from 1 to 4 carbon atoms as defined herein. Examples include methoxycarbonylaminomethoxy, ethoxycarbonylaminomethoxy, n-propoxycarbonylaminomethoxy, iso-propoxycarbonylaminomethoxy, n-butoxycarbonylaminomethoxy, 2-butoxycarbonylaminomethoxy, iso-butoxycarbonylaminomethoxy, tert-butoxycarbonylaminomethoxy, 2-(methoxycarbonylamino)ethoxy, 2-(ethoxycarbonylamino)ethoxy, 2-(n-propoxycarbonylamino)ethoxy, 2-(iso-propoxycarbonylamino)ethoxy, 2-(n-butoxycarbonylamino)ethoxy, 2-(2-butoxycarbonylamino)ethoxy, 2-(iso-butoxycarbonylamino)ethoxy, 2-(tert-butoxycarbonylamino)ethoxy.

$C_2$-$C_6$-Alkenyloxy is a radical of the formula R—O—, wherein R is a straight-chain or branched alkenyl group having from 2 to 6, in particular 2 to 4 carbon atoms. Examples include vinyloxy, allyloxy (2-propen-1-yloxy), 1-propen-1-yloxy, 2-propen-2-yloxy, methallyloxy (2-methylprop-2-en-1-yloxy) and the like. $C_3$-$C_5$-Alkenyloxy is, in particular, allyloxy, 1-methylprop-2-en-1-yloxy, 2-buten-1-yloxy, 3-buten-1-yloxy, methallyloxy, 2-penten-1-yloxy, 3-penten-1-yloxy, 4-penten-1-yloxy, 1-methylbut-2-en-1-yloxy or 2-ethylprop-2-en-1-yloxy.

$C_6$-$C_{12}$-Aryl-$C_1$-$C_4$-alkoxy is an alkoxy radical having from 1 to 4, preferably 1 or 2 carbon atoms as defined herein, wherein one hydrogen atom is replaced by a $C_6$-$C_{12}$-aryl group as defined herein. Examples include benzyloxy.

$C_1$-$C_6$-Alkylsulfonylamino-$C_1$-$C_4$-alkoxy is an alkoxy radical having from 1 to 4, preferably 1 or 2 carbon atoms as defined herein, wherein one hydrogen atom is replaced by an alkylsulfonylamino group having from 1 to 6, preferably from 1 to 4 carbon atoms as defined herein. Examples include 2-(methylsulfonylamino)ethoxy, 2-(ethylsulfonylamino)ethoxy, 2-[(2-methylpropyl)sulfonylamino]ethoxy.

(Halogenated $C_1$-$C_6$-alkyl)sulfonylamino-$C_1$-$C_4$-alkoxy is an alkoxy radical having from 1 to 4, preferably 1 or 2 carbon atoms as defined herein, wherein one hydrogen atom is replaced by an alkylsulfonylamino group having from 1 to 6, preferably from 1 to 4 carbon atoms as defined herein, wherein the alkyl group is halogenated. Examples include 2-(trifluoromethylsulfonylamino)ethoxy.

$C_6$-$C_{12}$-Arylsulfonylamino-$C_1$-$C_4$-alkoxy is an alkoxy radical having from 1 to 4, preferably 1 or 2 carbon atoms as defined herein, wherein one hydrogen atom is replaced by a $C_6$-$C_{12}$-arylsulfonylamino group as defined herein. Examples include 2-(phenylsulfonylamino)ethoxy, 2-(naphthylsulfonylamino)ethoxy.

($C_6$-$C_{12}$-Aryl-$C_1$-$C_6$-alkyl)sulfonylamino-$C_1$-$C_4$-alkoxy is an alkoxy radical having from 1 to 4, preferably 1 or 2 carbon atoms as defined herein, wherein one hydrogen atom is replaced by a ($C_6$-$C_{12}$-aryl-$C_1$-$C_6$-alkyl)sulfonylamino group, preferably by a ($C_6$-$C_{12}$-aryl-$C_1$-$C_2$-alkyl)sulfonylamino group. Examples include 2-(benzylsulfonylamino)ethoxy.

$C_3$-$C_{12}$-Heterocyclylsulfonylamino-$C_1$-$C_4$-alkoxy is an alkoxy radical having from 1 to 4, preferably 1 or 2 carbon atoms as defined herein, wherein one hydrogen atom is replaced by a $C_3$-$C_{12}$-heterocyclylsulfonylamino group as defined herein. Examples include 2-(pyridin-3-yl-sulfonylamino)ethoxy.

$C_3$-$C_{12}$-Heterocyclyl-$C_1$-$C_4$-alkoxy is an alkoxy radical having from 1 to 4, preferably 1 or 2 carbon atoms as defined herein, wherein one hydrogen atom is replaced by a $C_3$-$C_{12}$-heterocyclyl group as defined herein. Examples include 2-(N-pyrrolidinyl)ethoxy, 2-(N-morpholinyl)ethoxy and 2-(N-imidazolyl)ethoxy.

$C_1$-$C_2$-Alkylenedioxo is a radical of the formula —O—R—O—, wherein R is a straight-chain or branched alkylene group having from 1 or 2 carbon atoms as defined herein. Examples include methylenedioxo.

$C_6$-$C_{12}$-Aryloxy is a radical of the formula R—O—, wherein R is an aryl group having from 6 to 12, in particular 6 carbon atoms as defined herein. Examples include phenoxy.

$C_3$-$C_{12}$-Heterocyclyloxy is a radical of the formula R—O—, wherein R is a $C_3$-$C_{12}$-heterocyclyl group having from 3 to 12, in particular from 3 to 7 carbon atoms as defined herein. Examples include pyridin-2-yloxy.

$C_1$-$C_6$-Alkylthio is a radical of the formula R—S—, wherein R is an alkyl radical having from 1 to 6, preferably from 1 to 4 carbon atoms as defined herein. Examples include methylthio, ethylthio, propylthio, butylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropyl and 1-ethyl-2-methylpropyl.

Halogenated $C_1$-$C_6$-alkylthio is a radical of the formula R—S—, wherein R is a halogenated alkyl radical having from 1 to 6, preferably from 1 to 4 carbon atoms as defined herein. Examples include halogenomethylthio, dihalogenomethylthio, trihalogenomethylthio, (R)-1-halogenoethylthio, (S)-1-halogenoethylthio, 2-halogenoethylthio, 1,1-dihalogenoethylthio, 2,2-dihalogenoethylthio, 2,2,2-trihalogenoethylthio, (R)-1-halogenopropylthio, (S)-1-halogenopropylthio, 2-halogenopropylthio, 3-halogenopropylthio, 1,1-dihalogenopropylthio, 2,2-dihalogenopropylthio, 3,3-dihalogenopropylthio, 3,3,3-trihalogenopropylthio, (R)-2-halogeno-1-methylethylthio, (S)-2-halogeno-1-methylethylthio, (R)-2,2-dihalogeno-1-methylethylthio, (S)-2,2-dihalogeno-1-methylethylthio, (R)-1,2-dihalogeno-1-methylethylthio, (S)-1,2-dihalogeno-1-methylethylthio, (R)-2,2,2-trihalogeno-1-methylethylthio, (S)-2,2,2-trihalogeno-1-methylethylthio, 2-halogeno-1-(halogenomethyl)ethylthio, 1-(dihalogenomethyl)-2,2-dihalogenoethylthio, (R)-1-halogenobutylthio, (S)-1-halogenobutylthio, 2-halogenobutylthio, 3-halogenobutylthio, 4-halogenobutylthio, 1,1-dihalogenobutylthio, 2,2-dihalogenobutylthio, 3,3-dihalogenobutylthio, 4,4-dihalogenobutylthio, 4,4,4-trihalogenobutylthio, etc. Particular examples include the fluorinated $C_1$-$C_4$alkylthio groups as defined, such as trifluoromethylthio.

$C_1$-$C_6$-Alkylsulfinyl is a radical of the formula R—S(O)—, wherein R is an alkyl radical having from 1 to 6, preferably from 1 to 4 carbon atoms as defined herein. Examples include methylsulfinyl, ethylsulfinyl, propylsulfinyl, butylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, hexylsulfinyl, 1,1-dimethylpropylsulfinyl, 1,2-dimethylpropylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropyl and 1-ethyl-2-methylpropyl.

$C_1$-$C_6$-Alkylsulfonyl is a radical of the formula R—S(O)$_2$—, wherein R is an alkyl radical having from 1 to 6, preferably from 1 to 4 carbon atoms as defined herein. Examples include methylsulfonyl, ethylsulfonyl, propylsulfonyl, butylsulfonyl, pentylsulfonyl, 1-methylbutylsulfonyl, 2-methylbutylsulfonyl, 3-methylbutylsulfonyl, 2,2-dimethylpropylsulfonyl, 1-ethylpropylsulfonyl, hexylsulfonyl, 1,1-dimethylpropylsulfonyl, 1,2-dimethylpropylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropyl and 1-ethyl-2-methylpropyl.

(Halogenated $C_1$-$C_6$-alkyl)sulfonyl is a $C_1$-$C_6$-alkylsulfonyl as defined herein, wherein at least one, e.g. 1, 2, 3, 4 or all of the hydrogen atoms are replaced by 1, 2, 3, 4 or a corresponding number of identical or different halogen atoms.

$C_6$-$C_{12}$-Arylsulfonyl is a radical of the formula R—S(O)$_2$—, wherein R is an aryl radical having from 6 to 12 carbon atoms as defined herein. Examples include phenylsulfonyl.

($C_6$-$C_{12}$-Aryl-$C_1$-$C_4$-alkyl)sulfonyl is a radical of the formula R—S(O)$_2$—, wherein R is a $C_6$-$C_{12}$-aryl-$C_1$-$C_4$-alkyl radical, in particular a $C_6$-$C_{12}$-aryl-$C_1$-$C_2$-alkyl radical as defined herein. Examples include benzylsulfonyl.

$C_3$-$C_{12}$-Heterocyclylsulfonyl is a radical of the formula R—S(O)$_2$—, wherein R is $C_3$-$C_{12}$-heterocyclyl as defined herein.

Aminosulfonyl is NH$_2$—S(O)$_2$—.

$C_1$-$C_6$-Alkylaminosulfonyl is a radical of the formula R—NH—S(O)$_2$— wherein R is an alkyl radical having from 1 to 6, preferably from 1 to 4 carbon atoms as defined herein. Examples include methylaminosulfonyl, ethylaminosulfonyl, n-propylaminosulfonyl, iso-propylaminosulfonyl, n-butylaminosulfonyl, 2-butylaminosulfonyl, iso-butylaminosulfonyl, tert-butylaminosulfonyl.

Di-$C_1$-$C_6$-alkylaminosulfonyl is a radical of the formula RR'N—S(O)$_2$— wherein R and R' are independently of each other an alkyl radical having from 1 to 6, preferably from 1 to 4 carbon atoms as defined herein. Examples include dimethylaminosulfonyl, diethylaminosulfonyl, N-methyl-N-ethylaminosulfonyl.

$C_6$-$C_{12}$-Arylaminosulfonyl is a radical of the formula R—NH—S(O)$_2$— wherein R is an aryl radical having from 6 to 12, preferably 6 carbon atoms as defined herein.

Amino is NH$_2$.

$C_1$-$C_6$-Alkylamino is a radical of the formula R—NH— wherein R is an alkyl radical having from 1 to 6, in particular from 1 to 4 carbon atoms as defined herein. Examples include methylamino, ethylamino, n-propylamino, iso-propylamino, n-butylamino, 2-butylamino, iso-butylamino, tert-butylamino.

(Halogenated $C_1$-$C_6$-alkyl)amino is a $C_1$-$C_6$-alkylamino as defined herein, wherein at least one, e.g. 1, 2, 3, 4 or all of the hydrogen atoms are replaced by 1, 2, 3, 4 or a corresponding number of identical or different halogen atoms.

Di-$C_1$-$C_6$-alkylamino is a radical of the formula RR'N— wherein R and R' are independently of each other an alkyl radical having from 1 to 6, in particular from 1 to 4 carbon atoms as defined herein. Examples include dimethylamino, diethylamino, N-methyl-N-ethylamino.

Di-(halogenated $C_1$-$C_6$-alkyl)amino is a di-$C_1$-$C_6$-alkylamino as defined herein, wherein at least one, e.g. 1, 2, 3, 4 or all of the hydrogen atoms are replaced by 1, 2, 3, 4 or a corresponding number of identical or different halogen atoms.

$C_1$-$C_6$-Alkylcarbonylamino is a radical of the formula R—C(O)—NH—, wherein R is an alkyl radical having from 1 to 6, in particular from 1 to 4 carbon atoms as defined herein. Examples include acetamido (methylcarbonylamino), propionamido, n-butyramido, 2-methylpropionamido (isopropylcarbonylamino), 2,2-dimethylpropionamido and the like.

(Halogenated $C_1$-$C_6$-alkyl)carbonylamino is a $C_1$-$C_6$-alkylcarbonylamino as defined herein, wherein at least one, e.g. 1, 2, 3, 4 or all of the hydrogen atoms are replaced by 1, 2, 3, 4 or a corresponding number of identical or different halogen atoms.

$C_6$-$C_{12}$-Arylcarbonylamino is a radical of the formula R—C(O)—NH—, wherein R is an aryl radical having from 6 to 12 carbon atoms as defined herein. Examples include phenylcarbonylamino.

$C_2$-$C_6$-Alkenylamino is a radical of the formula R—NH—, wherein R is a straight-chain or branched alkenyl group having from 2 to 6, in particular 2 to 4 carbon atoms. Examples include vinylamino, allylamino (2-propen-1-ylamino), 1-propen-1-ylamino, 2-propen-2-ylamino, methallylamino (2-methylprop-2-en-1-ylamino) and the like. $C_3$-$C_5$-Alkenylamino is, in particular, allylamino, 1-methylprop-2-en-1-ylamino, 2-buten-1-ylamino, 3-buten-1-ylamino, methallylamino, 2-penten-1-ylamino, 3-penten-1-ylamino, 4-penten-1-ylamino, 1-methylbut-2-en-1-ylamino or 2-ethylprop-2-en-1-ylamino.

$C_1$-$C_6$-Alkylsulfonylamino is a radical of the formula R—S(O)$_2$—NH—, wherein R is an alkyl radical having from 1 to 6, in particular from 1 to 4 carbon atoms as defined herein. Examples include methylsulfonylamino, ethylsulfonylamino, n-propylsulfonylamino, iso-propylsulfonylamino, n-butylsulfonylamino, 2-butylsulfonylamino, iso-butylsulfonylamino, tert-butylsulfonylamino.

(Halogenated $C_1$-$C_6$ alkyl)sulfonylamino is a $C_1$-$C_6$-alkylsulfonylamino as defined herein, wherein at least one, e.g. 1, 2, 3, 4 or all of the hydrogen atoms are replaced by 1, 2, 3, 4 or a corresponding number of identical or different halogen atoms.

$C_6$-$C_{12}$-Arylsulfonylamino is a radical of the formula R—S(O)$_2$—NH—, wherein R is an aryl radical having from 6 to 12 carbon atoms as defined herein. Examples include phenylsulfonylamino.

Nitro is —NO$_2$.

$C_3$-$C_{12}$-Heterocyclyl is a 3- to 12-membered heterocyclic radical including a saturated heterocyclic radical, which generally has 3, 4, 5, 6, or 7 ring forming atoms (ring members), an unsaturated non-aromatic heterocyclic radical, which generally has 5, 6 or 7 ring forming atoms, and a heteroaromatic radical (hetaryl), which generally has 5, 6 or 7 ring forming atoms. The heterocyclic radicals may be bound via a carbon atom (C-bound) or a nitrogen atom (N-bound). Preferred heterocyclic radicals comprise 1 nitrogen atom as ring member atom and optionally 1, 2 or 3 further heteroatoms as ring members, which are selected, independently of each other from O, S and N. Likewise preferred heterocyclic radicals comprise 1 heteroatom as ring member, which is selected from O, S and N, and optionally 1, 2 or 3 further nitrogen atoms as ring members.

Examples of $C_3$-$C_{12}$-heterocyclyl include:

C- or N-bound 3-4-membered, saturated rings, such as
2-oxiranyl, 2-oxetanyl, 3-oxetanyl, 2-aziridinyl, 3-thiethanyl, 1-azetidinyl, 2-azetidinyl, 3-azetidinyl;

C-bound, 5-membered, saturated rings, such as
tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, tetrahydropyrazol-3-yl, tetrahydro-pyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 1,3,2-dioxathiolan-4-yl;

C-bound, 6-membered, saturated rings, such as
tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl;

N-bound, 5-membered, saturated rings, such as
tetrahydropyrrol-1-yl (pyrrolidin-1-yl), tetrahydropyrazol-1-yl, tetrahydroisoxazol-2-yl, tetrahydroisothiazol-2-yl, tetrahydroimidazol-1-yl, tetrahydrooxazol-3-yl, tetrahydrothiazol-3-yl;

N-bound, 6-membered, saturated rings, such as
piperidin-1-yl, hexahydropyrimidin-1-yl, hexahydropyrazin-1-yl (piperazin-1-yl), hexahydropyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl (morpholin-1-yl), tetrahydro-1,2-oxazin-2-yl;

C-bound, 5-membered, partially unsaturated rings, such as
2,3-dihydrofuran-2-yl, 2,3-dihydrofuran-3-yl, 2,5-dihydrofuran-2-yl, 2,5-di-hydrofuran-3-yl, 4,5-dihydrofuran-2-yl, 4,5-dihydrofuran-3-yl, 2,3-dihydro-thien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydro-oxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl;

C-bound, 6-membered, partially unsaturated rings, such as
2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydrothiopyran-6-yl, 2H-3,4-dihydrothiopyran-5-yl, 2H-3,4-dihydrothiopyran-4-yl, 2H-3,4-dihydrothiopyran-3-yl, 2H-3,4-dihydrothiopyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetra-hydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl-, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydro-pyridin-3-yl, 1,2-dihydropyridin-4-yl, 1,2-dihydropyridin-5-yl, 1,2-dihydro-pyridin-6-yl, 3,4-dihydropyridin-2-yl, 3,4-dihydropyridin-3-yl, 3,4-dihydro-pyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2- oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydropyridazin-4-yl, 1,2,5,6-tetra-hydropyridazin-5-yl, 1,2,5,6-tetrahydropyridazin-6-yl, 1,2,3,6-tetrahydro-pyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5-6-tetrahydropyrimidin-2-yl, 3,4,5,6-tetrahydropyrimidin-4-yl, 3,4,5,6-tetrahydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydro-pyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-oxazin-4-yl, 6H-1,3-oxazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl or 3,4-dihydropyrimidin-6-yl;

N-bound, 5-membered, partially unsaturated rings, such as 2,3-dihydro-1H-pyrrol-1-yl, 2,5-dihydro-1H-pyrrol-1-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl;

N-bound, 6-membered, partially unsaturated rings, such as 1,2,3,4-tetrahydropyridin-1-yl, 1,2,5,6-tetrahydropyridin-1-yl, 1,4-dihydro-pyridin-1-yl, 1,2-dihydropyridin-1-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazin-2-yl, 2H-3,4-dihydro-1,2-oxazin-2-yl, 2H-3,4-dihydro-1,2-thiazin-2-yl, 2,3,4,5-tetrahydropyridazin-2-yl, 1,2,5,6-tetrahydropyridazin-1-yl, 1,2,5,6-tetrahydropyridazin-2-yl, 1,2,3,6-tetrahydropyridazin-1-yl, 3,4,5,6-tetrahydropyrimidin-3-yl, 1,2,3,4-tetrahydropyrazin-1-yl, 1,2,3,4-tetrahydropyrimidin-1-yl, 1,2,3,4-tetrahydropyrimidin-3-yl, 2,3-dihydro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl;

C-bound, 5-membered, heteroaromatic rings, such as 2-furyl, 3-furyl, 2-thienyl, 3-thienyl, pyrrol-2-yl, pyrrol-3-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, oxazol-2-yl, oxazol-4-yl, oxazol-5-yl, thiazol-2-yl, thiazol-4-yl, thiazol-5-yl, 1,2,3-oxadiazol-4-yl, 1,2,3-oxadiazol-5-yl, 1,2,4-oxadiazol-3-yl, 1,2,4,-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl, 1,2,3-triazol-4-yl, 1,2,4-triazol-3-yl, tetrazol-5-yl;

C-bound, 6-membered, heteroaromatic rings, such as pyridin-2-yl, pyridin-3-yl, pyridin-4-yl (4-pyridyl), pyridazin-3-yl, pyridazin-4-yl, pyrimidin-2-yl, pyrimidin-4-yl, pyrimidin-5-yl, pyrazin-2-yl, 1,3,5-triazin-2-yl, 1,2,4-triazin-3-yl, 1,2,4-triazin-5-yl, 1,2,4-triazin-6-yl, 1,2,4,5-tetrazin-3-yl;

N-bound, 5-membered, heteroaromatic rings, such as pyrrol-1-yl, pyrazol-1-yl, imidazol-1-yl, 1,2,3-triazol-1-yl, 1,2,4-triazol-1-yl, tetrazol-1-yl.

Heterocyclyl also includes bicyclic heterocycles, which comprise one of the described 5- or 6-membered heterocyclic rings and a further anellated, saturated or unsaturated or aromatic carbocycle, such as a benzene, cyclohexane, cyclohexene or cyclohexadiene ring, or a further anellated 5- or 6-membered heterocyclic ring, this heterocyclic ring being saturated or unsaturated or aromatic. These include quinolinyl, isoquinolinyl, indolyl, indolizinyl, isoindolyl, indazolyl, benzofuryl, benzothienyl, benzo[b]thiazolyl, benzoxazolyl, benzthiazolyl and benzimidazolyl. Examples of 5- or 6-membered heteroaromatic compounds comprising an anellated cycloalkenyl ring include dihydroindolyl, dihydroindolizinyl, dihydroisoindolyl, dihydrochinolinyl, dihydroisoquinolinyl, chromenyl and chromanyl.

$C_3$-$C_{12}$-Heteroarylene is a heteroaryl diradical. Examples include pyrid-2,5-ylene and pyrid-2,4-ylene.

With respect to the compounds' capability of inhibiting glycine transporter 1, the variables A, R, $R^1$, W, $A^1$, Q, Y, $A^2$, $X^1$, $R^2$, $R^3$, $R^4$, $X^2$, $X^3$, $R^5$, $R^6$, $R^7$, $R^8$, $R^9$, $R^{10}$, $R^{11}$, $R^{12}$, $R^{13}$, $R^{14}$, $R^{15}$, n preferably have the following meanings which, when taken alone or in combination, represent particular embodiments of the heterocyclic compounds of the formula (I) or any other formula disclosed herein.

In said formula (I), there may be one or more than one substituent R, $R^2$ and/or $R^3$. More particularly, there may be up to 3 substituents R², and up to 5 substituents R³. Preferably there is one substituent R and 1, 2 or 3 substituents R². Formula (I) may thus be depicted as follows:

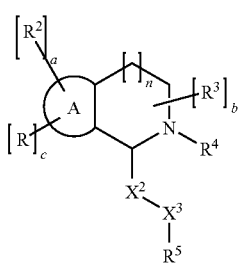
(I)

wherein a is 1, 2 or 3, b is 1, 2, 3, 4 or 5 and c is 1. If there is more than one radical R², these may be the same or different radicals. If there is more than one radical R³, these may be the same or different radicals.

A is a 5- or 6-membered heterocyclic ring which includes two carbon atoms from the cyclic moiety to which A is fused. The ring may be saturated, unsaturated non-aromatic or aromatic. As a heterocyclic ring, A may include 1, 2 or 3 heteroatoms as ring member atoms, which are selected, independently of each other from N, S and O. Preferred heterocyclic rings comprise 1 nitrogen atom as ring member atom and optionally 1 or 2 further heteroatoms as ring members, which are selected, independently of each other from O, S and N. Likewise preferred heterocyclic radicals comprise 1 heteroatom as ring member atom, which is selected from O, S and N, and optionally 1 or 2 further nitrogen atoms as ring member atoms. According to a particular embodiment, A is a heterocyclic ring selected from the group consisting of the following 5- or 6-membered heterocyclic rings:

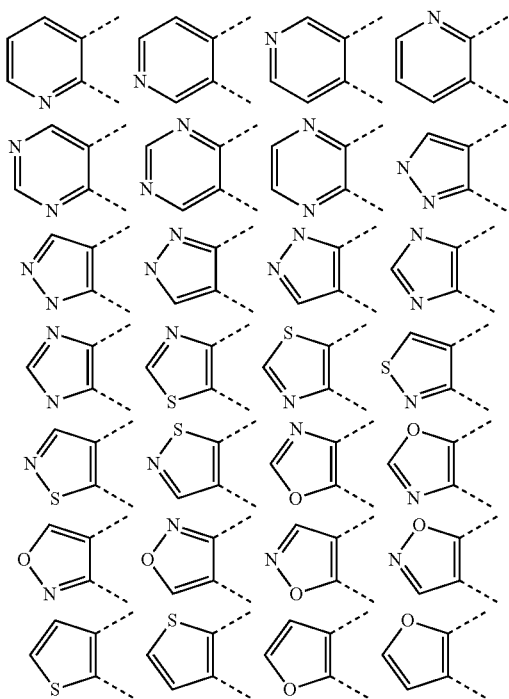

-continued

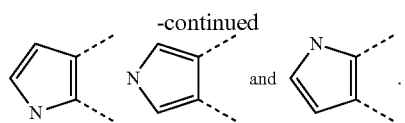

In said formulae, hydrogen atoms are not depicted. This is meant to illustrate that the free valency of a carbon or nitrogen atom may be either bound to a hydrogen atom, to R or to R². Accordingly, R and R² may be C- or N-bound at any position of ring A.

The skilled person will appreciate that some of the rings depicted above may be represented with a different structure, e.g. with hydrogen atoms having other positions than those shown above, for instance as given in the following structures:

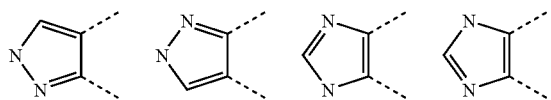

Preferably, A is a heterocyclic ring selected from the group consisting of the following 5- or 6-membered heterocyclic rings:

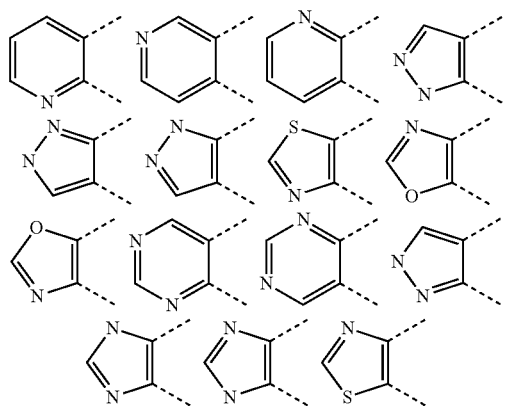

According to a further particular embodiment, A is a heterocyclic ring selected from the group consisting of the following 5- or 6-membered heterocyclic rings:

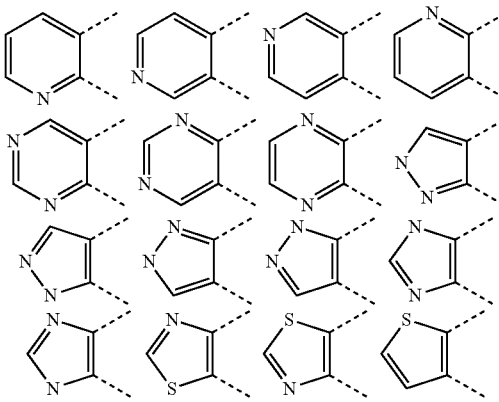

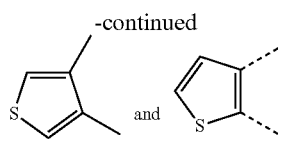 and

According to a preferred embodiment, A is a heterocyclic ring selected from the group consisting of the following 5- or 6-membered heterocyclic rings:

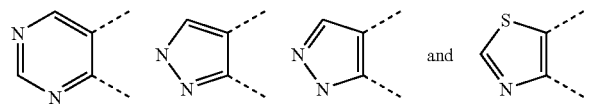

If ring A is a 5-membered heterocyclic ring it is preferred that R is bound to $G^1$ or $G^2$, in particular $G^2$:

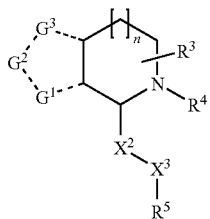

In said formula, $G^1$, $G^2$ and $G^3$ independently are —CH=, —CH$_2$—, —N=, —NH—, S or O, the dotted line represents a single or a double bond and $R^3$, $R^4$, $X^2$, $X^3$, $R^5$ are as defined herein.

If ring A is 6-membered heterocyclic ring it is preferred that R is bound to $G^1$ or $G^2$, in particular $G^2$:

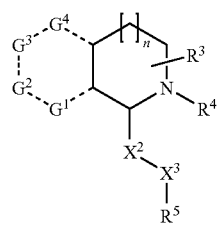

In said formula, $G^1$, $G^2$, $G^3$ and $G^4$ independently are —CH=, —CH$_2$—, —N=, —NH—, S or O, the dotted line represents a single or a double bond and $R^3$, $R^4$, $X^2$, $X^3$, $R^5$ are as defined herein.

Heterocyclic compounds having the following partial structures are preferred:

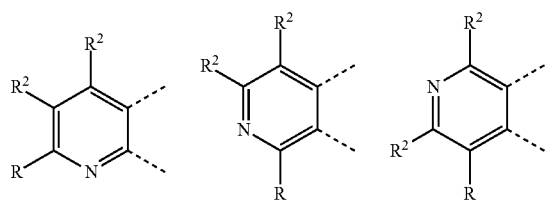
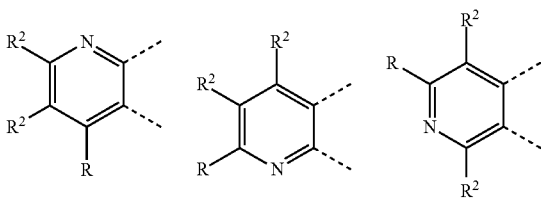
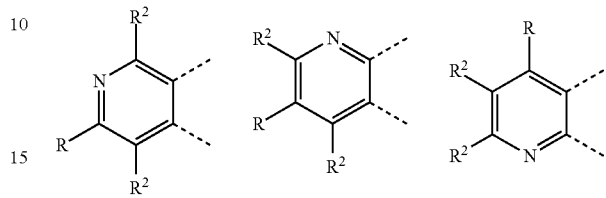
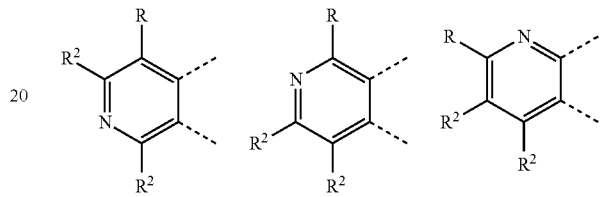
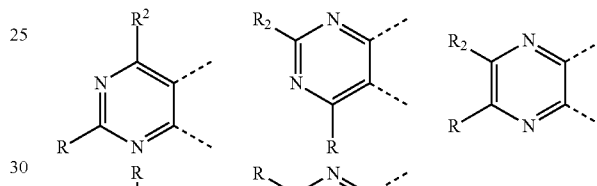
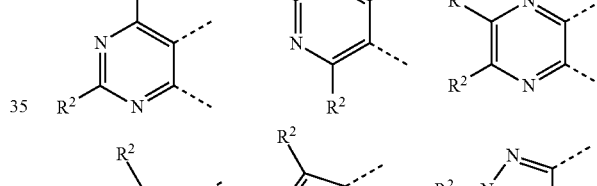
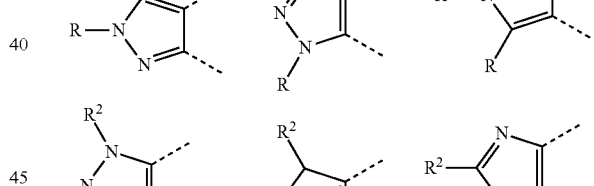
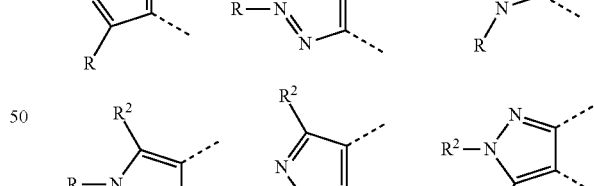
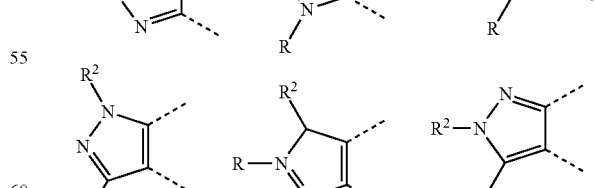
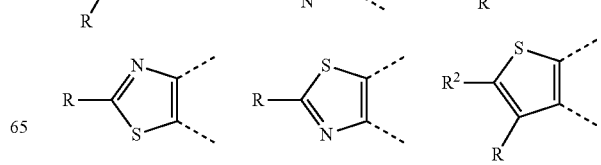

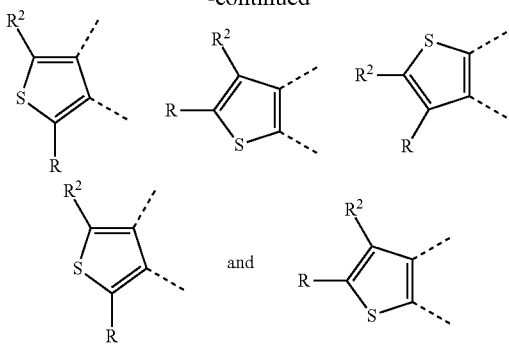

Heterocyclic compounds having the following partial structures are particularly preferred:

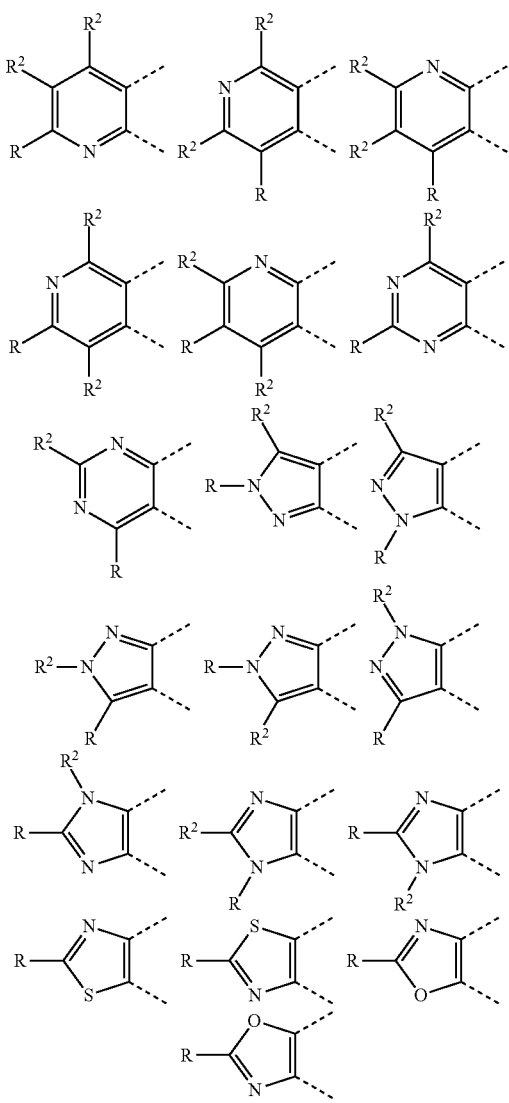

In said formulae, R and $R^2$ are as defined herein. If there is more than one radical $R^2$, these may be the same or different radicals.

According to a particular embodiment, the partial structures depicted above are fused with a tetrahydropyridine moiety (i.e., n is 1). The same applies to the preferred and particular embodiments disclosed for ring A.

According to one embodiment, R is NC-$A^1$-$X^1$—, in particular cyano (i.e. $A^1$ and $X^1$ are both a bond).

Preferably, R is $R^1$—W-$A^1$-Q-Y-$A^2$-$X^1$—, and A, $R^1$, W, $A^1$, Q, Y, $A^2$, $X^1$, $R^2$, $R^3$, $R^4$, $X^2$, $X^3$, $R^5$ are as defined herein.

$R^1$ is hydrogen, $C_1$-$C_6$-alkyl (e.g. methyl, ethyl, n-propyl or n-butyl, a further example being isopropyl or sec-butyl), $C_3$-$C_{12}$-cycloalkyl-$C_1$-$C_4$-alkyl (e.g. cyclopropylmethyl), halogenated $C_1$-$C_6$-alkyl (e.g. 3-fluoroprop-1-yl), hydroxy-$C_1$-$C_4$-alkyl, $C_1$-$C_6$-alkoxy-$C_1$-$C_4$-alkyl, amino-$C_1$-$C_4$-alkyl, $C_1$-$C_6$-alkylamino-$C_1$-$C_4$-alkyl, di-$C_1$-$C_6$-alkylamino-$C_1$-$C_4$-alkyl, $C_1$-$C_6$-alkylcarbonylamino-$C_1$-$C_4$-alkyl, $C_1$-$C_6$-alkyloxycarbonylamino-$C_1$-$C_4$-alkyl, $C_1$-$C_6$-alkylaminocarbonylamino-$C_1$-$C_4$-alkyl, di-$C_1$-$C_6$-alkylaminocarbonylamino-$C_1$-$C_4$-alkyl, $C_1$-$C_6$-alkylsulfonylamino-$C_1$-$C_4$-alkyl, (optionally substituted $C_6$-$C_{12}$-aryl-$C_1$-$C_6$-alkyl)amino-$C_1$-$C_4$-alkyl, optionally substituted $C_6$-$C_{12}$-aryl-$C_1$-$C_4$-alkyl, optionally substituted $C_3$-$C_{12}$-heterocyclyl-$C_1$-$C_4$-alkyl, $C_3$-$C_{12}$-cycloalkyl (e.g. cyclobutyl), $C_1$-$C_6$-alkylcarbonyl, $C_1$-$C_6$-alkoxycarbonyl, halogenated $C_1$-$C_6$-alkoxycarbonyl, $C_6$-$C_{12}$-aryloxycarbonyl, aminocarbonyl, $C_1$-$C_6$-alkylaminocarbonyl, (halogenated $C_1$-$C_4$-alkyl)aminocarbonyl, $C_6$-$C_{12}$-arylaminocarbonyl, $C_2$-$C_6$-alkenyl, $C_2$-$C_6$-alkynyl, optionally substituted $C_6$-$C_{12}$-aryl (e.g. phenyl), hydroxy, $C_1$-$C_6$-alkoxy, halogenated $C_1$-$C_6$-alkoxy, $C_1$-$C_6$-hydroxyalkoxy, $C_1$-$C_6$-alkoxy-$C_1$-$C_4$-alkoxy, amino-$C_1$-$C_4$-alkoxy, $C_1$-$C_6$-alkylamino-$C_1$-$C_4$-alkoxy, di-$C_1$-$C_6$-alkylamino-$C_1$-$C_4$-alkoxy, $C_1$-$C_6$-alkylcarbonylamino-$C_1$-$C_4$-alkoxy, $C_6$-$C_{12}$-arylcarbonylamino-$C_1$-$C_4$-alkoxy, $C_1$-$C_6$-alkoxycarbonylamino-$C_1$-$C_4$-alkoxy, $C_6$-$C_{12}$-aryl-$C_1$-$C_4$-alkoxy, $C_1$-$C_6$-alkylsulfonylamino-$C_1$-$C_4$-alkoxy, (halogenated $C_1$-$C_6$-alkyl)sulfonylamino-$C_1$-$C_4$-alkoxy, $C_6$-$C_{12}$-arylsulfonylamino-$C_1$-$C_4$-alkoxy, ($C_6$-$C_{12}$-aryl-$C_1$-$C_6$-alkyl)sulfonylamino-$C_1$-$C_4$-alkoxy, $C_3$-$C_{12}$-heterocyclylsulfonylamino-$C_1$-$C_4$-alkoxy, $C_3$-$C_{12}$-heterocyclyl-$C_1$-$C_4$-alkoxy, $C_6$-$C_{12}$-aryloxy, $C_3$-$C_{12}$-heterocyclyloxy, $C_1$-$C_6$-alkylthio, halogenated $C_1$-$C_6$-alkylthio, $C_1$-$C_6$-alkylamino, (halogenated $C_1$-$C_6$-alkyl)amino, di-$C_1$-$C_6$-alkylamino, di-(halogenated $C_1$-$C_6$-alkyl)amino, $C_1$-$C_6$-alkylcarbonylamino, (halogenated $C_1$-$C_6$-alkyl)carbonylamino, $C_6$-$C_{12}$-arylcarbonylamino, $C_1$-$C_6$-alkylsulfonylamino, (halogenated $C_1$-$C_6$-alkyl)sulfonylamino, $C_6$-$C_{12}$-arylsulfonylamino or optionally substituted $C_3$-$C_{12}$-heterocyclyl (e.g. 3-pyridyl, 1-methyl-1,2-diazol-4-yl or 1-methyl-1,3-diazol-4-yl, a further example being 2-pyridyl or 4-pyridyl).

Preferably, $R^1$ is hydrogen, $C_1$-$C_6$-alkyl (e.g. methyl, ethyl, n-propyl or n-butyl, a further example being isopropyl or sec-butyl), $C_3$-$C_{12}$-cycloalkyl-$C_1$-$C_4$-alkyl (e.g. cyclopropylmethyl), halogenated $C_1$-$C_6$-alkyl (e.g. 3-fluoroprop-1-yl), $C_1$-$C_6$-alkoxy-$C_1$-$C_4$-alkyl, amino-$C_1$-$C_4$-alkyl, $C_1$-$C_6$-alkylamino-$C_1$-$C_4$-alkyl, di-$C_1$-$C_6$-alkylamino-$C_1$-$C_4$-alkyl, $C_1$-$C_6$-alkyloxycarbonylamino-$C_1$-$C_4$-alkyl, $C_1$-$C_6$-alkylaminocarbonylamino-$C_1$-$C_4$-alkyl, $C_6$-$C_{12}$-aryl-$C_1$-$C_4$-alkyl, $C_3$-$C_{12}$-cycloalkyl (e.g. cyclobutyl), $C_2$-$C_6$-alkenyl, optionally substituted $C_6$-$C_{12}$-aryl (e.g. phenyl), hydroxy, $C_1$-$C_6$-alkylamino, (halogenated $C_1$-$C_6$-alkyl)amino, di-$C_1$-$C_6$-alkylamino or optionally substituted $C_3$-$C_{12}$-heterocyclyl (e.g. 3-pyridyl, 1-methyl-1,2-diazol-4-yl or 1-methyl-1,3-diazol-4-yl, a further example being 2-pyridyl or 4-pyridyl).

In particular, $R^1$ is hydrogen, $C_1$-$C_6$-alkyl (e.g. methyl, ethyl, n-propyl or n-butyl, a further example being isopropyl or sec-butyl), $C_3$-$C_{12}$-cycloalkyl-$C_1$-$C_4$-alkyl (e.g. cyclopropylmethyl), halogenated $C_1$-$C_6$-alkyl (e.g. 3-fluoroprop-1-yl), $C_3$-$C_{12}$-cycloalkyl (e.g. cyclobutyl), optionally substituted $C_6$-$C_{12}$-aryl (e.g. phenyl) or optionally substituted $C_3$-$C_{12}$-heterocyclyl (e.g. 3-pyridyl, 1-methyl-1,2-diazol-4-yl or 1-methyl-1,3-diazol-4-yl, a further example being 2-pyridyl or 4-pyridyl).

In connection with $R^1$, substituted $C_6$-$C_{12}$-aryl in particular includes $C_6$-$C_{12}$-aryl, such as phenyl or naphthyl, substituted with 1, 2 or 3 substituents selected from the group consisting of halogen, $C_1$-$C_4$-alkyl, $C_1$-$C_4$-haloalkyl, cyano, $C_1$-$C_4$-alkoxy, $C_1$-$C_4$-haloalkoxy, amino, $C_1$-$C_4$-alkylamino, $C_1$-$C_4$-dialkylamino, morpholino and piperidinyl. The same applies to substituted $C_6$-$C_{12}$-aryl in substituted $C_6$-$C_{12}$-aryl-$C_1$-$C_4$-alkyl.

In connection with $R^1$, substituted $C_3$-$C_{12}$-heterocyclyl in particular includes $C_3$-$C_{12}$-heterocyclyl, such as pyridyl, thienyl, diazolyl, quinolinyl, piperidinyl, piperazinyl or morpholinyl, substituted with 1, 2 or 3 substituents selected from the group consisting of halogen, $C_1$-$C_4$-alkyl, $C_1$-$C_4$-haloalkyl, $C_1$-$C_4$-alkoxycarbonyl, cyano, $C_1$-$C_4$-alkoxy, $C_1$-$C_4$-haloalkoxy, $C_1$-$C_4$-alkylsulfonyl, amino, $C_1$-$C_4$-alkylamino, $C_1$-$C_4$-dialkylamino, $C_6$-$C_{12}$-arylamino and $C_3$-$C_{12}$-heterocyclyl (e.g., morpholino or piperidinyl). The same applies to substituted $C_3$-$C_{12}$-heteroaryl in substituted $C_3$-$C_{12}$-heteroaryl-$C_1$-$C_4$-alkyl.

According to one embodiment, W is —$NR^8$— and Y is a bond. According to an alternative embodiment, W is a bond and Y is —$NR^9$—. According to a further alternative embodiment, W is a bond and Y is a bond, especially if $R^1$ is a nitrogen-bound radical, e.g. nitrogen-bound heterocyclyl such as piperazinyl or morpholinyl.

According to one embodiment, Q is —$S(O)_2$—. According to an alternative embodiment, Q is —$C(O)$—. If Q is a bond, at least one of W and Y is not a bond, e.g., W is a bond and Y is —$NR^9$—.

According to a particular embodiment, —W-$A^1$-Q-Y— is —W-$A^1$-$S(O)_2$—$NR^9$—, —$NR^8$—$S(O)_2$—, -$A^1$-$S(O)_2$— or —$S(O)_2$—. According to a further particular embodiment, —W-$A^1$-Q-Y— is —W-$A^1$-CO—$NR^9$— or —$NR^8$—CO—.

$A^1$ is optionally substituted $C_1$-$C_4$-alkylene or a bond. In connection with $A^1$, substituted $C_1$-$C_4$-alkylene in particular includes $C_1$-$C_4$-alkylene substituted with 1, 2 or 3 substituents selected from the group consisting of halogen, $C_1$-$C_4$-alkyl and cyano. Preferably, $A^1$ is a bond. If $A^1$ is $C_1$-$C_4$-alkylene, W is preferably —$NR^8$—.

$A^2$ is optionally substituted $C_1$-$C_4$-alkylene (e.g. methylene or 1,2-ethylene, a further example being 1,3-propylene), $C_1$-$C_4$-alkylene-CO—, —CO—$C_1$-$C_4$-alkylene, $C_1$-$C_4$-alkylene-O—$C_1$-$C_4$-alkylene, $C_1$-$C_4$-alkylene-$NR^{10}$—$C_1$-$C_4$-alkylene, optionally substituted $C_6$-$C_{12}$-arylene, optionally substituted $C_6$-$C_{12}$-heteroarylene or a bond. Additionally, $A^2$ may be optionally substituted $C_2$-$C_4$-alkenylen or optionally substituted $C_2$-$C_4$-alkynylene. Preferably, $A^2$ is optionally substituted $C_1$-$C_4$-alkylene (e.g. methylene or 1,2-ethylene, a further example being 1,3-propylene). More preferably, $A^2$ is $C_1$-$C_4$-alkylene (e.g. methylene or 1,2-ethylene, a further example being 1,3-propylene). Alternatively, it is preferred that $A^2$ is optionally substituted $C_6$-$C_{12}$-arylene, in particular $C_6$-$C_{12}$-arylene selected from the group consisting of phen-1,4-ylene and phen-1,3-ylene, or optionally substituted $C_6$-$C_{12}$-heteroarylene, in particular $C_6$-$C_{12}$-heteroarylene selected from the group consisting of pyrid-2,5-ylene and pyrid-2,4-ylene. If $A^2$ is a bond, $X^1$ is preferably optionally substituted $C_1$-$C_4$-alkylene. Alternatively, if $A^2$ is a bond, $X^1$ is in particular optionally substituted $C_2$-$C_4$-alkenylene or optionally substituted $C_2$-$C_4$-alkynylene.

In connection with $A^2$, substituted $C_1$-$C_4$-alkylene in particular includes $C_1$-$C_4$-alkylene substituted with 1, 2 or 3 substituents selected from the group consisting of halogen, $C_1$-$C_4$-alkyl, $C_1$-$C_4$-haloalkyl and cyano.

In connection with $A^2$, substituted $C_2$-$C_4$-alkenylene or substituted $C_2$-$C_4$-alkynylene in particular includes $C_2$-$C_4$-alkenylene or $C_2$-$C_4$-alkynylene substituted with 1, 2 or 3 substituents selected from the group consisting of halogen, $C_1$-$C_4$-alkyl, $C_1$-$C_4$-haloalkyl and cyano.

In connection with $A^2$, substituted $C_6$-$C_{12}$-arylene in particular includes $C_6$-$C_{12}$-arylene substituted with 1, 2 or 3 substituents selected from the group consisting of $C_1$-$C_4$-alkyl, $C_1$-$C_4$-haloalkyl, $C_1$-$C_4$-alkoxycarbonyl, cyano, $C_1$-$C_4$-alkoxy, $C_1$-$C_4$-haloalkoxy, $C_1$-$C_4$-alkylsulfonyl, amino, $C_1$-$C_4$-alkylamino, $C_1$-$C_4$-dialkylamino, $C_6$-$C_{12}$-arylamino and $C_3$-$C_{12}$-heterocyclyl (e.g., morpholino or piperidinyl).

In connection with $A^2$, substituted $C_6$-$C_{12}$-heteroarylene in particular includes $C_6$-$C_{12}$-heteroarylene substituted with 1, 2 or 3 substituents selected from the group consisting of $C_1$-$C_4$-alkyl, $C_1$-$C_4$-haloalkyl, $C_1$-$C_4$-alkoxycarbonyl, cyano, $C_1$-$C_4$-alkoxy, $C_1$-$C_4$-haloalkoxy, $C_1$-$C_4$-alkylsulfonyl, amino, $C_1$-$C_4$-alkylamino, $C_1$-$C_4$-dialkylamino, $C_6$-$C_{12}$-arylamino and $C_3$-$C_{12}$-heterocyclyl (e.g., morpholino or piperidinyl).

$X^1$ is —O—, —$NR^{11}$—, —S— optionally substituted $C_1$-$C_4$-alkylene (e.g. —$CH_2$—) or a bond. In connection with $X^1$, substituted $C_1$-$C_4$-alkylene in particular includes $C_1$-$C_4$-alkylene substituted with 1, 2 or 3 substituents selected from the group consisting of halogen, $C_1$-$C_4$-alkyl, $C_1$-$C_4$-haloalkyl and cyano. Additionally, $X^1$ may be optionally substituted $C_2$-$C_4$-alkenylen or optionally substituted $C_2$-$C_4$-alkynylene (e.g. propynylene). In connection with $X^1$, substituted $C_2$-$C_4$-alkenylene or substituted $C_2$-$C_4$-alkynylene in particular includes $C_2$-$C_4$-alkenylene or $C_2$-$C_4$-alkynylene substituted with 1, 2 or 3 substituents selected from the group consisting of halogen, $C_1$-$C_4$-alkyl, $C_1$-$C_4$-haloalkyl and cyano. According to one embodiment, $X^1$ is —O—, —$NR^{11}$— or —S—, in particular —O—. According to another embodiment, $X^1$ is a bond. Alternatively, it is preferred if $X^1$ is optionally substituted $C_1$-$C_4$-alkylene (e.g. —$CH_2$—, 1,2-ethylene and 1,3-propylene).

According to a particular embodiment, $A^2$ is a bond and $X^1$ is optionally substituted $C_1$-$C_4$-alkylene, optionally substituted $C_2$-$C_4$-alkenylene or optionally substituted $C_2$-$C_4$-alkynylene.

According to a particular embodiment, the structural element —Y-$A^2$-$X^1$— comprises at least 2, 3 or 4 atoms in the main chain. According to further particular embodiments the structural element —Y-$A^2$-$X^1$— has up to 4, 5 or 6 atoms in the main chain, such as 2 to 6, 2 to 5 or 2 to 4 atoms in the main chain, especially 2, 3 or 4 atoms in the main chain.

According to a particular embodiment, $R^1$—W-$A^1$-Q-Y-$A^2$-$X^1$— is $R^1$—$S(O)_2$—NH-$A^2$-$X^1$—, $R^1$—NH—$S(O)_2$-$A^2$-$X^1$—, $R^1$—C(O)—NH-$A^2$-$X^1$—, $R^1$—NH—C(O)-$A^2$-$X^1$— or $R^1$—NH-$A^2$-$X^1$—.

According to a further particular embodiment, —Y-$A^2$-$X^1$— is —$C_1$-$C_4$-alkylene-O— or —$NR^9$—$C_1$-$C_4$-alkylene-O—, with —Y-$A^2$-$X^1$— preferably having 2 to 6, 3 to 5 and especially 4 atoms in the main chain. Particular examples of —Y-$A^2$-$X^1$— include —$(CH_2)_3$—O— and —$NR^9$—$(CH_2)_2$—O—. In this particular embodiment, $R^9$ is as defined herein and preferably $R^9$ is hydrogen, $C_1$-$C_6$-alkyl (e.g. methyl or ethyl) or $C_3$-$C_{12}$-cycloalkyl (e.g. cyclopropyl), or $R^9$ is $C_1$-$C_4$-alkylene that is bound to a carbon atom in $A^2$ which is $C_1$-$C_4$-alkylene.

According to a further particular embodiment, —Y-$A^2$-$X^1$— is —$NR^9$—$C_1$-$C_4$-alkylene- (e.g. —NH—$CH_2$—, a further example being —NH—$(CH_2)_2$— or —NH—$(CH_2)_3$—), with —Y-$A^2$-$X^1$— preferably having 2 to 6, 3 to 5 and especially 2, 3 or 4 atoms in the main chain. In this particular embodiment, $R^9$ is as defined herein and preferably $R^9$ is hydrogen, $C_1$-$C_6$-alkyl (e.g. methyl) or $C_3$-$C_{12}$-heterocyclyl (e.g. 3-azetidinyl); or $R^9$ is $C_1$-$C_4$-alkylene that is bound to a carbon atom in $A^2$ which is $C_1$-$C_4$-alkylene.

According to a further particular embodiment, —Y-$A^2$-$X^1$— is —$NR^9$—$C_2$-$C_4$-alkenylene- or —$NR^9$—$C_2$-$C_4$-alkynylene- (e.g. —NH—$CH_2$—C≡C—), with —Y-$A^2$-$X^1$— preferably having 2 to 6, 3 to 5 and especially 4 atoms in the main chain. In this particular embodiment, $R^9$ is as defined herein and preferably is $R^9$ is hydrogen, $C_1$-$C_6$-alkyl (e.g. methyl or ethyl) or $C_3$-$C_{12}$-cycloalkyl (e.g. cyclopropyl or cyclobutyl).

According to a further particular embodiment, —Y-$A^2$-$X^1$— is —$C_1$-$C_4$-alkylene- (e.g. —$(CH_2)_2$—), with —Y-$A^2$-$X^1$— preferably having 2 to 6, 2 to 5, 2 to 4 and especially 2 atoms in the main chain. If A is a heterocyclic ring, this embodiment of —Y-$A^2$-$X^1$— is particularly suitable.

According to a further particular embodiment, the structural motif —Y-$A^2$-$X^1$ as disclosed herein is bound to Q being —S(O)$_2$— or —C(O)—. Particular examples for this embodiment include heterocyclic compounds of the invention wherein R is $R^1$—S(O)$_2$—Y-$A^2$-$X^1$ or $R^1$—C(O)—Y-$A^2$-$X^1$.

The radical R and in particular the radical $R^1$—W-$A^1$-Q-Y-$A^2$-$X^1$— may, in principle, be bound to any position of the heterocyclic ring A. Particular examples include:

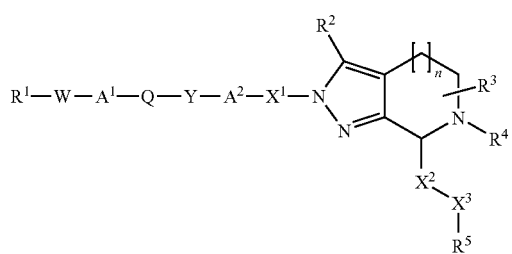

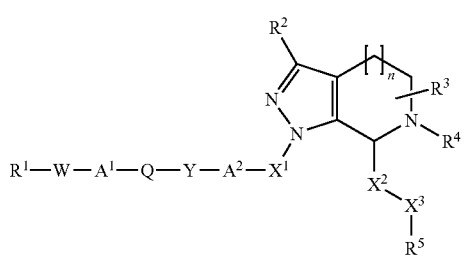

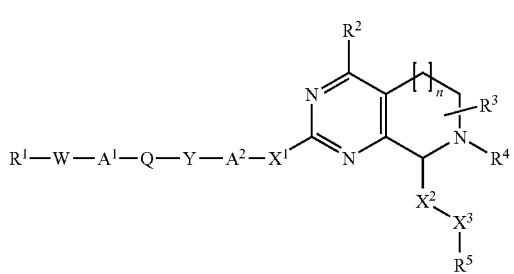

Further particular examples include:

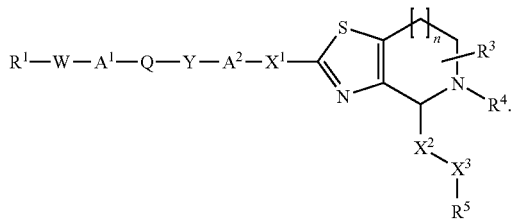

In said formulae, $R^1$, W, $A^1$, Q, Y, $A^2$, $X^1$, $R^2$, $R^3$, $R^4$, $X^2$, $X^3$, $R^5$, n are as defined herein.

Further particular examples include heterocyclic compounds of the above formulae wherein the radical $R^1$—W-$A^1$-Q-Y-$A^2$-$X^1$— is replaced by the radical —CN.

In addition to the radical $R^1$—W-$A^1$-Q-Y-$A^2$-X—, the heterocyclic compounds of the invention may have one or more than one further substituent bound to the heterocyclic ring A. In these positions, the skeleton of the heterocyclic compounds may thus be substituted with one or more than one radical $R^2$. If there is more than one radical $R^2$, these may be the same or different radicals.

$R^2$ is hydrogen, halogen, $C_1$-$C_6$-alkyl, halogenated $C_1$-$C_4$-alkyl, hydroxy-$C_1$-$C_4$-alkyl, —CN, $C_2$-$C_6$-alkenyl, $C_2$-$C_6$-alkynyl, optionally substituted $C_6$-$C_{12}$-aryl, hydroxy, $C_1$-$C_6$-alkoxy, halogenated $C_1$-$C_6$-alkoxy, $C_1$-$C_6$-alkoxycarbonyl, $C_2$-$C_6$-alkenyloxy, $C_6$-$C_{12}$-aryl-$C_1$-$C_4$-alkoxy, $C_1$-$C_6$-alkylcarbonyloxy, $C_1$-$C_6$-alkylthio, $C_1$-$C_6$-alkylsulfinyl, $C_1$-$C_6$-alkylsulfonyl, aminosulfonyl, amino, $C_1$-$C_6$-alkylamino, $C_2$-$C_6$-alkenylamino, nitro or optionally substituted $C_3$-$C_{12}$-heterocyclyl, or two radicals $R^2$ together with the ring atoms of A to which they are bound form an optionally substituted 5- or 6-membered ring.

In connection with $R^2$, substituted $C_6$-$C_{12}$-aryl in particular includes $C_6$-$C_{12}$-aryl, such as phenyl, substituted with 1, 2 or 3 substituents selected from the group consisting of halogen and $C_1$-$C_4$-alkyl, $C_1$-$C_4$-haloalkyl, cyano, $C_1$-$C_4$-alkoxy and $C_1$-$C_4$-haloalkoxy.

In connection with $R^2$, substituted $C_3$-$C_{12}$-heterocyclyl in particular includes $C_3$-$C_{12}$-heterocyclyl, such as morpholinyl, pyrrolidinyl and piperidinyl, substituted with 1, 2 or 3 substituents selected from the group consisting of halogen, $C_1$-$C_4$-alkyl, $C_1$-$C_4$-haloalkyl, cyano, $C_1$-$C_4$-alkoxy and $C_1$-$C_4$-haloalkoxy.

An optionally substituted 5- or 6-membered ring that is formed by two radicals $R^2$ together with the ring atoms of A to which they are bound is, for instance, a benzene ring.

Preferably, $R^2$ is hydrogen, halogen, or $C_1$-$C_6$-alkoxy. In particular, $R^2$ is hydrogen.

In 1-, 3-, 4- and/or 5-(if n is 2) position, the heterocyclic compounds of the invention may be substituted with one or more than one radical $R^3$. If there is more than one radical $R^3$, these may be the same or different radicals. The heterocyclic compounds of the invention may therefore be represented by the following formula.

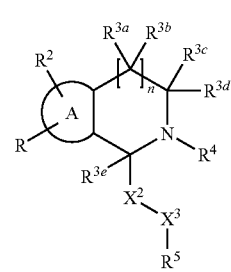

wherein $R^{3a}$, $R^{3b}$, $R^{3c}$, $R^{3d}$, $R^{3e}$ independently have one of the meanings given for $R^3$, and A, R, $R^2$, $R^3$, $R^4$, $X^2$, $X^3$, $R^5$, n are as defined herein.

According to a particular embodiment, the heterocyclic compounds of the invention have one of the following formulae:

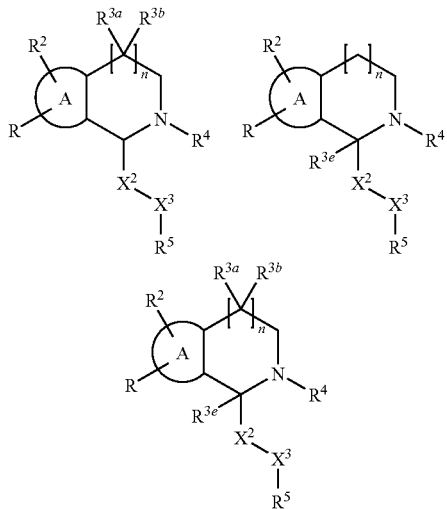

wherein $R^{3a}$, $R^{3b}$, $R^{3e}$ independently have the meaning of $R^3$ and A, R, $R^2$, $R^3$, $R^4$, $X^2$, $X^3$, $R^5$, n are as defined herein.

$R^3$ is hydrogen, halogen, $C_1$-$C_6$-alkyl, $C_1$-$C_6$-alkoxy, or two radicals $R^3$ together with the carbon atom to which they are attached form a carbonyl group.

Preferably, $R^3$ is hydrogen or $C_1$-$C_6$-alkyl. In particular, $R^3$ is hydrogen.

$R^4$ is hydrogen, $C_1$-$C_6$-alkyl, halogenated $C_1$-$C_4$-alkyl, hydroxy-$C_1$-$C_4$-alkyl, $C_1$-$C_6$-alkoxy-$C_1$-$C_4$-alkyl, amino-$C_1$-$C_4$-alkyl, $CH_2CN$, —CHO, $C_1$-$C_4$-alkylcarbonyl, (halogenated $C_1$-$C_4$-alkyl)carbonyl, $C_1$-$C_4$-alkoxycarbonyl (e.g. t-butyloxycarbonyl), $C_6$-$C_{12}$-arylcarbonyl, $C_1$-$C_6$-alkylaminocarbonyl, $C_2$-$C_6$-alkenyl, —C(=NH)NH$_2$, —C(=NH)NHCN, $C_1$-$C_6$-alkylsulfonyl, $C_6$-$C_{12}$-arylsulfonyl, amino or $C_3$-$C_{12}$-heterocyclyl.

Preferably, $R^4$ is hydrogen, $C_1$-$C_6$-alkyl, halogenated $C_1$-$C_4$-alkyl, amino-$C_1$-$C_4$-alkyl, $CH_2CN$, $C_1$-$C_4$-alkylcarbonyl, (halogenated $C_1$-$C_4$-alkyl)carbonyl, $C_1$-$C_4$-alkoxycarbonyl (e.g. t-butyloxycarbonyl), —C(=NH)NH$_2$, —C(=NH)NHCN, $C_1$-$C_6$-alkylsulfonyl, amino or $C_3$-$C_{12}$-heterocyclyl.

$X^2$ is —O—, —$NR^6$—, —S—, >$CR^{12a}R^{12b}$ or a bond. Preferably, $X^2$ is >$CR^{12a}R^{12b}$.

$X^3$ is —O—, —S—, >$CR^{13a}R^{13b}$ or a bond. Preferably, $X^3$ is a bond.

Thus, it is preferred if $X^2$ is >$CR^{12a}R^{12b}$ and $X^3$ is a bond.

$R^{12a}$ is hydrogen, optionally substituted $C_1$-$C_6$-alkyl, $C_1$-$C_6$-alkylamino-$C_1$-$C_4$-alkyl, di-$C_1$-$C_6$-alkylamino-$C_1$-$C_4$-alkyl, $C_3$-$C_{12}$-heterocyclyl-$C_1$-$C_6$-alkyl, optionally substituted $C_6$-$C_{12}$-aryl or hydroxy. In particular, $R^{12a}$ is hydrogen or $C_1$-$C_6$-alkyl.

$R^{13a}$ is hydrogen, optionally substituted $C_1$-$C_6$-alkyl, $C_1$-$C_6$-alkylamino-$C_1$-$C_4$-alkyl, di-$C_1$-$C_6$-alkylamino-$C_1$-$C_4$-alkyl, $C_3$-$C_{12}$-heterocyclyl-$C_1$-$C_6$-alkyl, optionally substituted $C_6$-$C_{12}$-aryl or hydroxy. In particular, $R^{13a}$ is hydrogen or $C_1$-$C_6$-alkyl.

In connection with $R^{12a}$ and $R^{13a}$, substituted $C_1$-$C_6$-alkyl in particular includes $C_1$-$C_6$-alkyl substituted with 1, 2 or 3 substituents selected from the group consisting of halogen, hydroxy, $C_1$-$C_4$-alkoxy and amino.

In connection with $R^{12a}$ and $R^{13a}$, substituted $C_6$-$C_{12}$-aryl in particular includes $C_6$-$C_{12}$-aryl, such as phenyl, substituted with 1, 2 or 3 substituents selected from the group consisting of $C_1$-$C_4$-alkyl, $C_1$-$C_4$-haloalkyl, cyano, $C_1$-$C_4$-alkoxy and $C_1$-$C_4$-haloalkoxy.

$R^{12b}$ is hydrogen or $C_1$-$C_6$-alkyl. According to a particular embodiment, $R^{12b}$ is hydrogen.

$R^{13b}$ is hydrogen or $C_1$-$C_6$-alkyl. According to a particular embodiment, $R^{13b}$ is hydrogen.

Alternatively, $R^{12a}$ and $R^{12b}$, or $R^{13a}$ and $R^{13b}$, together are together are carbonyl or, preferably, optionally substituted $C_1$-$C_4$-alkylene (e.g. 1,3-propylene), wherein one —$CH_2$— of $C_1$-$C_4$-alkylene may be replaced by an oxygen atom or —$NR^{14}$—.

In connection with $R^{12a}$ and $R^{12b}$, or $R^{13a}$ and $R^{13b}$, substituted $C_1$-$C_4$-alkylene in particular includes $C_1$-$C_4$-alkylene substituted with 1, 2 or 3 substituents selected from the group consisting of halogen, $C_1$-$C_4$-alkyl, $C_1$-$C_4$-haloalkyl, cyano, $C_1$-$C_4$-alkoxy and $C_1$-$C_4$-haloalkoxy.

According to a particular embodiment, $R^{12a}$ is $C_1$-$C_6$-alkyl and $R^{12b}$ is hydrogen or $C_1$-$C_6$-alkyl, or $R^{13a}$ is $C_1$-$C_6$-alkyl and $R^{13b}$ is hydrogen or $C_1$-$C_6$-alkyl.

According to a further particular embodiment, $R^{12a}$ is hydrogen and $R^{12b}$ is hydrogen, or $R^{13a}$ is hydrogen and $R^{13b}$ is hydrogen.

According to a further particular embodiment, $R^{12a}$ and $R^{12b}$ together are optionally substituted 1,3-propylene, or $R^{13a}$ and $R^{13b}$ together are optionally substituted 1,3-propylene.

$R^5$ is optionally substituted $C_6$-$C_{12}$-aryl (e.g. 4-chlorophenyl, a further example being phenyl), optionally substituted $C_3$-$C_{12}$-cycloalkyl or optionally substituted $C_3$-$C_{12}$-heterocyclyl.

In connection with $R^5$, substituted $C_3$-$C_{12}$-cycloalkyl in particular includes $C_3$-$C_{12}$-cycloalkyl, such as cyclopropyl or cyclohexyl, substituted with 1, 2 or 3 substituents selected from the group consisting of halogen, optionally substituted $C_1$-$C_6$-alkyl, halogenated $C_1$-$C_6$-alkyl, CN, hydroxy, $C_1$-$C_6$-alkoxy, halogenated $C_1$-$C_6$-alkoxy, amino, $C_1$-$C_6$-alkylamino, di-$C_1$-$C_6$-alkylamino and $C_3$-$C_{12}$-heterocyclyl.

In connection with $R^5$, substituted $C_6$-$C_{12}$-aryl in particular includes $C_6$-$C_{12}$-aryl, such as phenyl, substituted with 1, 2 or 3 substituents selected from the group consisting of halogen (e.g. F, Cl, Br), optionally substituted $C_1$-$C_6$-alkyl (e.g. methyl), halogenated $C_1$-$C_6$-alkyl (e.g. trifluormethyl), CN, hydroxy, $C_1$-$C_6$-alkoxy (e.g. methoxy), halogenated $C_1$-$C_6$-alkoxy, amino, $C_1$-$C_6$-alkylamino, di-$C_1$-$C_6$-alkylamino and $C_3$-$C_{12}$-heterocyclyl.

In connection with $R^5$, substituted $C_3$-$C_{12}$-heterocyclyl in particular includes $C_3$-$C_{12}$-heterocyclyl substituted with 1, 2 or 3 substituents selected from the group consisting of halogen, optionally substituted $C_1$-$C_6$-alkyl, halogenated $C_1$-$C_6$-alkyl, CN, hydroxy, $C_1$-$C_6$-alkoxy, halogenated $C_1$-$C_6$-alkoxy, amino, $C_1$-$C_6$-alkylamino, di-$C_1$-$C_6$-alkylamino and $C_3$-$C_{12}$-heterocyclyl.

In connection with $R^5$, $C_3$-$C_{12}$-heterocyclyl in particular is $C_3$-$C_{12}$-heteroaryl.

Preferably, $R^5$ is optionally substituted $C_6$-$C_{12}$-aryl, in particular as in heterocyclic compounds of the formula:

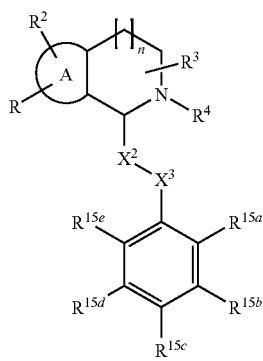

wherein A, R, $R^2$, $R^3$, $R^4$, $X^2$, $X^3$, n are as defined herein; and $R^{15a}$, $R^{15b}$, $R^{15c}$, $R^{15d}$, $R^{15e}$, $R^{15f}$ independently are hydrogen, halogen (e.g. chloro), optionally substituted $C_1$-$C_6$-alkyl, halogenated $C_1$-$C_6$-alkyl, CN, hydroxy, $C_1$-$C_6$-alkoxy, amino, $C_1$-$C_6$-alkylamino, di-$C_1$-$C_6$-alkylamino or $C_3$-$C_{12}$-heterocyclyl.

According to a particular embodiment, the invention relates to heterocyclic compounds of the formula:

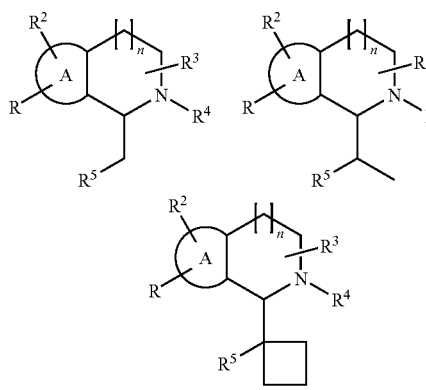

wherein A, R, $R^2$, $R^3$, $R^4$, $R^5$, n are as defined herein, $R^5$ preferably being optionally substituted aryl and in particular optionally substituted phenyl as disclosed herein.

In connection with $R^5$ or $R^{15a}$, $R^{15b}$, $R^{15c}$, $R^{15d}$, $R^{15e}$, substituted $C_1$-$C_6$-alkyl in particular includes $C_1$-$C_6$-alkyl, especially $C_1$-$C_4$-alkyl, substituted with 1, 2 or 3 substituents selected from the group consisting of hydroxy, $C_1$-$C_6$-alkoxy, amino, $C_1$-$C_6$-alkylamino, di-$C_1$-$C_6$-alkylamino and $C_3$-$C_{12}$-heterocyclyl (e.g. morpholinyl or piperidinyl).

According to a particular embodiment, $R^{15a}$, $R^{15b}$, $R^{15d}$, $R^{15e}$ are hydrogen and $R^{15c}$ is different from hydrogen (para-mono-substitution).

According to a further particular embodiment, $R^{15a}$, $R^{15c}$, $R^{15d}$, $R^{15e}$ are hydrogen and $R^{15b}$ is different from hydrogen (meta-mono-substitution).

In connection with $R^{15a}$, $R^{15b}$, $R^{15c}$, $R^{15d}$, $R^{15e}$, $C_3$-$C_{12}$-heterocyclyl in particular includes morpholinyl, imidazolyl and pyrazolyl.

The index n is 0, 1 or 2. According to a particular embodiment, n is 1.

$R^6$ is hydrogen or $C_1$-$C_6$-alkyl. Preferably, $R^6$ is hydrogen.
$R^7$ is hydrogen or $C_1$-$C_6$-alkyl. Preferably, $R^7$ is hydrogen.
$R^8$ is hydrogen or $C_1$-$C_6$-alkyl. Preferably, $R^8$ is hydrogen.
$R^9$ is hydrogen, $C_1$-$C_6$-alkyl, $C_3$-$C_{12}$-cycloalkyl, amino-$C_1$-$C_6$-alkyl, optionally substituted $C_6$-$C_{12}$-aryl-$C_1$-$C_4$-alkyl or $C_3$-$C_{12}$-heterocyclyl (e.g. 3-azetidinyl). Preferably, $R^9$ is hydrogen or $C_1$-$C_6$-alkyl.

According to a particular embodiment, $R^9$ and $R^1$ together are $C_1$-$C_4$-alkylene (e.g. 1,3-propylene) so as that $R^9$ and $R^1$ together with the atom in Q to which $R^1$ is bound and the nitrogen atom to which $R^9$ is bound form an heterocyclic ring having, in particular, 4, 5 or 6 ring member atoms (including the nitrogen atom and Q). With W and $A^1$ both being a bond, such a ring may be represented by the following partial structure:

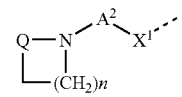

wherein Q is as defined herein (e.g. $S(O)_2$) and n is 0, 1, 2, 3 or 4

According to a further particular embodiment, $R^9$ is $C_1$-$C_4$-alkylene (e.g. methylene or 1,3-propylene) that is bound to a carbon atom in $A^2$ and $A^2$ is $C_1$-$C_4$-alkylene so that $R^9$ and at least part of $A^2$ together with the nitrogen atom to which $R^9$ is bound form an N-containing heterocyclic ring having, in particular, 4, 5, 6 or 7 ring member atoms (including the nitrogen atom). Such a ring may be represented by the following partial structure:

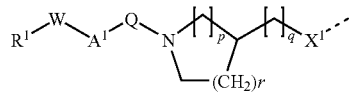

wherein $R^1$, W, $A^1$, Q and $X^1$ are as defined herein, p is 1 or 2, r is 0, 1 or 2 and q is 0, 1 or 2. In this particular embodiment, $X^1$ preferably is —O—. Particular combinations of p, r and q include p=1, r=0, q=1; and p=1, r=0, q=0. Alternatively, p is 0, r is 3 and q is 1, with $X^1$ preferably being —O—.

According to a further particular embodiment, $R^9$ is $C_1$-$C_4$-alkylene (e.g. methylene or 1,3-propylene) that is bound to a carbon atom in $X^1$ and $X^1$ is $C_1$-$C_4$-alkylene so that $R^9$ and at least part of $X^1$ together with the nitrogen atom to which $R^9$ is bound form an N-containing heterocyclic ring having, in particular, 4, 5, 6 or 7 ring member atoms (including the nitrogen atom). With $A^2$ being a bond, such a ring may be represented by the following partial structure:

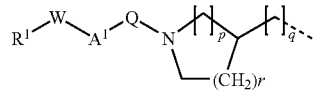

wherein $R^1$, W, $A^1$, Q and $X^1$ are as defined herein, p is 1 or 2, r is 0, 1 or 2 and q is 0, 1 or 2. Particular combinations of p, r and q include p=1, r=0, q=0.

$R^{10}$ is hydrogen, $C_1$-$C_6$-alkyl or $C_1$-$C_6$-alkylsulfonyl. Preferably, $R^{10}$ is hydrogen.

$R^{11}$ is hydrogen or $C_1$-$C_6$-alkyl. Preferably, $R^{11}$ is hydrogen.

Alternatively, $R^9$, $R^{11}$ together are $C_1$-$C_4$-alkylene.

$R^{14}$ is hydrogen or $C_1$-$C_6$-alkyl. Preferably, $R^{14}$ is hydrogen.

$R^{15}$ is hydrogen or $C_1$-$C_6$-alkyl. Preferably, $R^{15}$ is hydrogen.

Particular embodiments of heterocyclic compounds of the invention result if

A is a 5- or 6-membered heterocyclic ring;

R is $R^1$—W-$A^1$-Q-Y-$A^2$-$X^1$— or NC-$A^1$-$X^1$—;

$R^1$ is hydrogen, $C_1$-$C_6$-alkyl, $C_3$-$C_{12}$-cycloalkyl-$C_1$-$C_4$-alkyl, halogenated $C_1$-$C_6$-alkyl, hydroxy-$C_1$-$C_4$-alkyl, $C_1$-$C_6$-alkoxy-$C_1$-$C_4$-alkyl, amino-$C_1$-$C_4$-alkyl, $C_1$-$C_6$-alkylamino-$C_1$-$C_4$-alkyl, di-$C_1$-$C_6$-alkylamino-$C_1$-$C_4$-alkyl, $C_1$-$C_6$-alkylcarbonylamino-$C_1$-$C_4$-alkyl, $C_1$-$C_6$-alkyloxycarbonylamino-$C_1$-$C_4$-alkyl, $C_1$-$C_6$-alkylaminocarbonylamino-$C_1$-$C_4$-alkyl, di-$C_1$-$C_6$-alkylaminocarbonylamino-$C_1$-$C_4$-alkyl, $C_1$-$C_6$-alkylsulfonylamino-$C_1$-$C_4$-alkyl, (optionally substituted $C_6$-$C_{12}$-aryl-$C_1$-$C_6$-alkyl)amino-$C_1$-$C_4$-alkyl, optionally substituted $C_6$-$C_{12}$-aryl-$C_1$-$C_4$-alkyl, optionally substituted $C_3$-$C_{12}$-heterocyclyl-$C_1$-$C_4$-alkyl, $C_3$-$C_{12}$-cycloalkyl, $C_1$-$C_6$-alkylcarbonyl, $C_1$-$C_6$-alkoxycarbonyl, halogenated $C_1$-$C_6$-alkoxycarbonyl, $C_6$-$C_{12}$-aryloxycarbonyl, aminocarbonyl, $C_1$-$C_6$-alkylaminocarbonyl, (halogenated $C_1$-$C_4$-alkyl)aminocarbonyl, $C_6$-$C_{12}$-arylaminocarbonyl, $C_2$-$C_6$-alkenyl, $C_2$-$C_6$-alkynyl, optionally substituted $C_6$-$C_{12}$-aryl, hydroxy, $C_1$-$C_6$-alkoxy, halogenated $C_1$-$C_6$-alkoxy, $C_1$-$C_6$-hydroxyalkoxy, $C_1$-$C_6$-alkoxy-$C_1$-$C_4$-alkoxy, amino-$C_1$-$C_4$-alkoxy, $C_1$-$C_6$-alkylamino-$C_1$-$C_4$-alkoxy, di-$C_1$-$C_6$-alkylamino-$C_1$-$C_4$-alkoxy, $C_1$-$C_6$-alkylcarbonylamino-$C_1$-$C_4$-alkoxy, $C_6$-$C_{12}$-arylcarbonylamino-$C_1$-$C_4$-alkoxy, $C_1$-$C_6$-alkoxycarbonylamino-$C_1$-$C_4$-alkoxy, $C_6$-$C_{12}$-aryl-$C_1$-$C_4$-alkoxy, $C_1$-$C_6$-alkylsulfonylamino-$C_1$-$C_4$-alkoxy, (halogenated $C_1$-$C_6$-alkyl)sulfonylamino-$C_1$-$C_4$-alkoxy, $C_6$-$C_{12}$-arylsulfonylamino-$C_1$-$C_4$-alkoxy, ($C_6$-$C_{12}$-aryl-$C_1$-$C_6$-alkyl)sulfonylamino-$C_1$-$C_4$-alkoxy, $C_3$-$C_{12}$-heterocyclylsulfonylamino-$C_1$-$C_4$-alkoxy, $C_3$-$C_{12}$-heterocyclyl-$C_1$-$C_4$-alkoxy, $C_6$-$C_{12}$-aryloxy, $C_3$-$C_{12}$-heterocyclyloxy, $C_1$-$C_6$-alkylthio, halogenated $C_1$-$C_6$-alkylthio, $C_1$-$C_6$-alkylamino, (halogenated $C_1$-$C_6$-alkyl)amino, di-$C_1$-$C_6$-alkylamino, di-(halogenated $C_1$-$C_6$-alkyl)amino, $C_1$-$C_6$-alkylcarbonylamino, (halogenated $C_1$-$C_6$-alkyl)carbonylamino, $C_6$-$C_{12}$-arylcarbonylamino, $C_1$-$C_6$-alkylsulfonylamino, (halogenated $C_1$-$C_6$-alkyl)sulfonylamino, $C_6$-$C_{12}$-arylsulfonylamino or optionally substituted $C_3$-$C_{12}$-heterocyclyl;

W is —$NR^8$— or a bond;

$A^1$ is optionally substituted $C_1$-$C_4$-alkylene or a bond;

Q is —S(O)$_2$—, —C(O)— or a bond;

Y is —$NR^9$— or a bond;

$A^2$ is optionally substituted $C_1$-$C_4$-alkylene, $C_1$-$C_4$-alkylene-CO—, —CO—$C_1$-$C_4$-alkylene, $C_1$-$C_4$-alkylene-O—$C_1$-$C_4$-alkylene, $C_1$-$C_4$-alkylene-$NR^{10}$—$C_1$-$C_4$-alkylene, optionally substituted $C_6$-$C_{12}$-arylene, optionally substituted $C_6$-$C_{12}$-heteroarylene or a bond;

$X^1$ is —O—, —$NR^{11}$—, —S—, optionally substituted $C_1$-$C_4$-alkylene or a bond, with the proviso that if Q is a bond, W is —$NR^8$— or Y is —$NR^9$—;

$R^2$ is hydrogen, halogen, $C_1$-$C_6$-alkyl, halogenated $C_1$-$C_4$-alkyl, hydroxy-$C_1$-$C_4$-alkyl, —CN, $C_2$-$C_6$-alkenyl, $C_2$-$C_6$-alkynyl, optionally substituted $C_6$-$C_{12}$-aryl, hydroxy, $C_1$-$C_6$-alkoxy, halogenated $C_1$-$C_6$-alkoxy, $C_1$-$C_6$-alkoxycarbonyl, $C_2$-$C_6$-alkenyloxy, $C_6$-$C_{12}$-aryl-$C_1$-$C_4$-alkoxy, $C_1$-$C_6$-alkylcarbonyloxy, $C_1$-$C_6$-alkylthio, $C_1$-$C_6$-alkylsulfinyl, $C_1$-$C_6$-alkylsulfonyl, aminosulfonyl, amino, $C_1$-$C_6$-alkylamino, $C_2$-$C_6$-alkenylamino, nitro or optionally substituted $C_3$-$C_{12}$-heterocyclyl, or two radicals $R^2$ together with the ring atoms of A to which they are bound form an optionally substituted 5- or 6-membered ring;

$R^3$ is hydrogen, halogen, $C_1$-$C_6$-alkyl or $C_1$-$C_6$-alkoxy, or two radicals $R^3$ together with the carbon atom to which they are attached form a carbonyl group;

$R^4$ is hydrogen, $C_1$-$C_6$-alkyl, halogenated $C_1$-$C_4$-alkyl, hydroxy-$C_1$-$C_4$-alkyl, $C_1$-$C_6$-alkoxy-$C_1$-$C_4$-alkyl, amino-$C_1$-$C_4$-alkyl, $CH_2CN$, —CHO, $C_1$-$C_4$-alkylcarbonyl, (halogenated $C_1$-$C_4$-alkyl)carbonyl, $C_1$-$C_4$-alkoxycarbonyl, $C_6$-$C_{12}$-arylcarbonyl, $C_1$-$C_6$-alkylaminocarbonyl, $C_2$-$C_6$-alkenyl, —C(=NH)$NH_2$, —C(=NH)NHCN, $C_1$-$C_6$-alkylsulfonyl, $C_6$-$C_{12}$-arylsulfonyl, amino or $C_3$-$C_{12}$-heterocyclyl;

$X^2$ is —O—, —$NR^6$—, —S—, >$CR^{12a}R^{12b}$ or a bond;

$X^3$ is —O—, —$NR^7$—, —S—, >$CR^{13a}R^{13b}$ or a bond;

$R^5$ is optionally substituted $C_6$-$C_{12}$-aryl, optionally substituted $C_3$-$C_{12}$-cycloalkyl or optionally substituted $C_3$-$C_{12}$-heterocyclyl;

n is 0, 1, or 2;

$R^6$ is hydrogen or $C_1$-$C_6$-alkyl;

$R^7$ is hydrogen or $C_1$-$C_6$-alkyl;

$R^8$ is hydrogen or $C_1$-$C_6$-alkyl;

$R^9$ is hydrogen, $C_1$-$C_6$-alkyl, $C_3$-$C_{12}$-cycloalkyl, amino-$C_1$-$C_6$-alkyl, optionally substituted $C_6$-$C_{12}$-aryl-$C_1$-$C_4$-alkyl; or $R^9$, $R^{11}$ together are $C_1$-$C_4$-alkylene; or $R^9$ is $C_1$-$C_4$-alkylene that is bound to a carbon atom in $A^2$ and $A^2$ is $C_1$-$C_4$-alkylene or to a carbon atom in $X^1$ and $X^1$ is $C_1$-$C_4$-alkylene;

$R^{10}$ is hydrogen, $C_1$-$C_6$-alkyl or $C_1$-$C_6$-alkylsulfonyl;

$R^{11}$ is hydrogen or $C_1$-$C_6$-alkyl, or $R^9$, $R^{11}$ together are $C_1$-$C_4$-alkylene, $R^{12a}$ is hydrogen, optionally substituted $C_1$-$C_6$-alkyl, $C_1$-$C_6$-alkylamino-$C_1$-$C_4$-alkyl, di-$C_1$-$C_6$-alkylamino-$C_1$-$C_4$-alkyl, $C_3$-$C_{12}$-heterocyclyl-$C_1$-$C_6$-alkyl, optionally substituted $C_6$-$C_{12}$-aryl or hydroxy;

$R^{12b}$ is hydrogen or $C_1$-$C_6$-alkyl, or $R^{12a}$, $R^{12b}$ together are carbonyl or optionally substituted $C_1$-$C_4$-alkylene, wherein one —$CH_2$— of $C_1$-$C_4$-alkylene may be replaced by an oxygen atom or —$NR^{14}$—;

$R^{13a}$ is hydrogen, optionally substituted $C_1$-$C_6$-alkyl, $C_1$-$C_6$-alkylamino-$C_1$-$C_4$-alkyl, di-$C_1$-$C_6$-alkylamino-$C_1$-$C_4$-alkyl, $C_3$-$C_{12}$-heterocyclyl-$C_1$-$C_6$-alkyl, optionally substituted $C_6$-$C_{12}$-aryl or hydroxy;

$R^{13b}$ is hydrogen or $C_1$-$C_6$-alkyl, or $R^{13a}$, $R^{13b}$ together are carbonyl or optionally substituted $C_1$-$C_4$-alkylene, wherein one —$CH_2$— of $C_1$-$C_4$-alkylene may be replaced by an oxygen atom or —$NR^{15}$—;

$R^{14}$ is hydrogen or $C_1$-$C_6$-alkyl; and $R^{15}$ is hydrogen or $C_1$-$C_6$-alkyl, or if one or more of said variables A, R, $R^1$, W, $A^1$, Q, Y, $A^2$, $X^1$, $R^2$, $R^3$, $R^4$, $X^2$, $X^3$, $R^5$, $R^6$, $R^7$, $R^8$, $R^9$, $R^{10}$, $R^{11}$, $R^{12}$, $R^{13}$, $R^{14}$, $R^{15}$, n are defined more precisely as disclosed herein.

Further particular embodiments of heterocyclic compounds of the invention result if A is a ring selected from the group consisting of the following 5- or 6-membered heterocyclic rings:

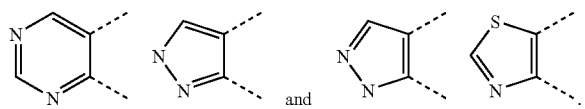

and

R is R$^1$—W-A$^1$-Q-Y-A$^2$-X$^1$—;

R$^1$ is hydrogen, C$_1$-C$_6$-alkyl (e.g. methyl; ethyl; n-propyl; isopropyl, n-butyl, sec-butyl), C$_3$-C$_{12}$-cycloalkyl-C$_1$-C$_4$-alkyl (e.g. cyclopropylmethyl), halogenated C$_1$-C$_6$-alkyl (e.g. 3-fluoroprop-1-yl), C$_3$-C$_{12}$-cycloalkyl (e.g. cyclobutyl), optionally substituted C$_6$-C$_{12}$-aryl (e.g. phenyl), or optionally substituted C$_3$-C$_{12}$-heterocyclyl (e.g. 2-pyridyl, 3-pyridyl, 4-pyridyl, 1-methyl-1,2-diazol-4-yl, 1-methyl-1,3-diazol-4-yl);

W is a bond;

A$^1$ is a bond;

Q is —S(O)$_2$—, —C(O)— or a bond;

Y is —NR$^9$— or a bond;

with the proviso that if Q is a bond, Y is —NR$^9$—;

A$^2$ is C$_1$-C$_4$-alkylene (e.g. methylene; 1,2-ethylene, 1,3-propylene);

X$^1$ is a bond;

R$^2$ is hydrogen;

R$^3$ is hydrogen;

R$^4$ is hydrogen or C$_1$-C$_4$-alkoxycarbonyl (e.g. t-butyloxycarbonyl);

X$^2$ is >CR$^{12a}$R$^{12b}$;

X$^3$ is a bond;

R$^5$ is optionally substituted phenyl (e.g. phenyl or 4-chlorophenyl);

R$^9$ is hydrogen or C$_3$-C$_{12}$-heterocyclyl (e.g. 3-azetidinyl); and

R$^{12a}$ is hydrogen;

R$^{12b}$ is hydrogen, or

R$^{12a}$, R$^{12b}$ together are optionally substituted C$_1$-C$_4$-alkylene (e.g. 1,3-propylene).

Further particular embodiments of heterocyclic compounds of the invention result if A is a ring selected from the group consisting of the following 5- or 6-membered heterocyclic rings:

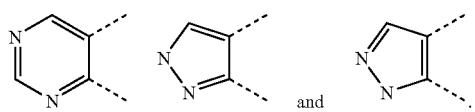

and

R is R$^1$—W-A$^1$-Q-Y-A$^2$-X$^1$—;

R$^1$ is hydrogen, C$_1$-C$_6$-alkyl (e.g. methyl, ethyl, n-propyl or n-butyl), C$_3$-C$_{12}$-cycloalkyl-C$_1$-C$_4$-alkyl (e.g. cyclopropylmethyl), halogenated C$_1$-C$_6$-alkyl (e.g. 3-fluoroprop-1-yl), C$_3$-C$_{12}$-cycloalkyl (e.g. cyclobutyl), optionally substituted C$_6$-C$_{12}$-aryl (e.g. phenyl), or optionally substituted C$_3$-C$_{12}$-heterocyclyl (e.g. 3-pyridyl, 1-methyl-1,2-diazol-4-yl or 1-methyl-1,3-diazol-4-yl);

W is a bond;

A$^1$ is a bond;

Q is —S(O)$_2$—, —C(O)— or a bond;

Y is —NR$^9$— or a bond;

with the proviso that if Q is a bond, Y is —NR$^9$—;

A$^2$ is C$_1$-C$_4$-alkylene (e.g. methylene or 1,2-ethylene);

X$^1$ is a bond;

R$^2$ is hydrogen;

R$^3$ is hydrogen;

R$^4$ is hydrogen or C$_1$-C$_4$-alkoxycarbonyl (e.g. t-butyloxycarbonyl);

X$^2$ is >CR$^{12a}$R$^{12b}$;

X$^3$ is a bond;

R$^5$ is optionally substituted phenyl (e.g. 4-chlorophenyl);

R$^9$ is hydrogen; and

R$^{12a}$, R$^{12b}$ together are optionally substituted C$_1$-C$_4$-alkylene (e.g. 1,3-propylene).

Particular compounds of the present invention are the heterocyclic compounds disclosed in preparation examples and physiologically tolerated acid addition salts thereof. These include for each preparation example the exemplified compound as well as the corresponding free base and any other physiologically tolerated acid addition salts of the free base (if the exemplified compound is a salt), or any physiologically tolerated acid addition salt of the free base (if the exemplified compound is a free base). These further include enantiomers, diastereomers, tautomers and any other isomeric forms of said compounds, be they explicitly or implicitly disclosed.

The compounds of the formula (I) can be prepared by analogy to methods which are well known in the art. Suitable methods for the preparation of compounds of formula (I) is outlined in the following schemes.

The processes depicted in schemes 1 and 2 are useful for obtaining 2-substituted piperidin-3-ones which then can be converted to 2-substituted 4-((dimethyl)methylene)-3-oxopiperidines according to the process depicted in scheme 3.

Scheme 1:

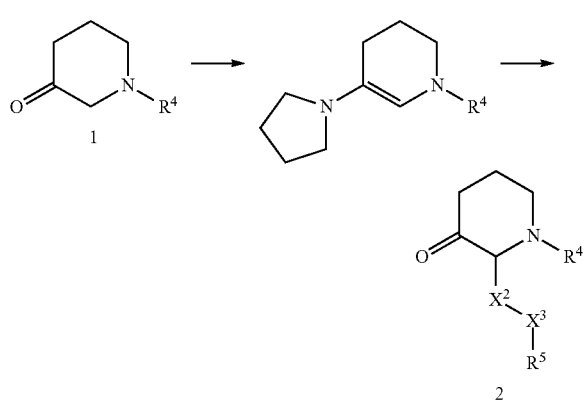

As shown in scheme 1, the compound of general formula 1 readily undergoes enamine alkylation to give the compound of general formula 2.

Scheme 2:

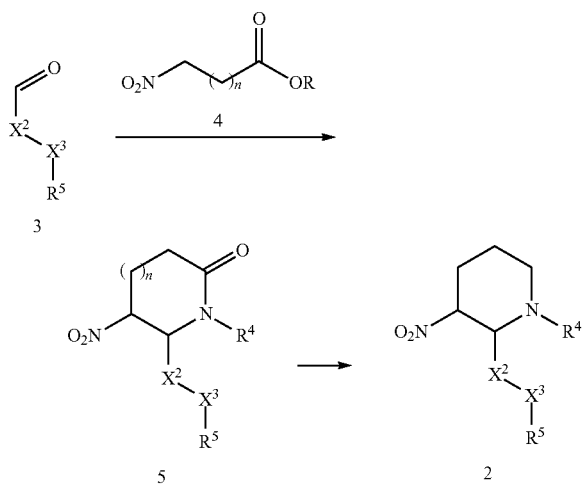

As shown in scheme 2, the compound of general formula 3 readily undergoes acid catalyzed condensation with the compound of general formula 4 in the presence of ammonium acetate to give the compound of general formula 5. The compound of general formula 5 can be further functionalized using standard transformations (e.g. amid reduction, Nef reaction) to yield the compound of general formula 2.

Scheme 3:

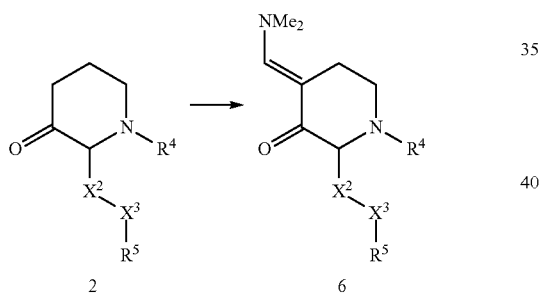

As shown in scheme 3, the compound of general formula 2 readily undergoes condensation with dimethylformamide dimethyl acetal to give the compound of general formula 6.

The process depicted in scheme 4 is useful for obtaining 4,5-dihydro-pyrazolo[3,4-c]pyridines of the present invention.

Scheme 4:

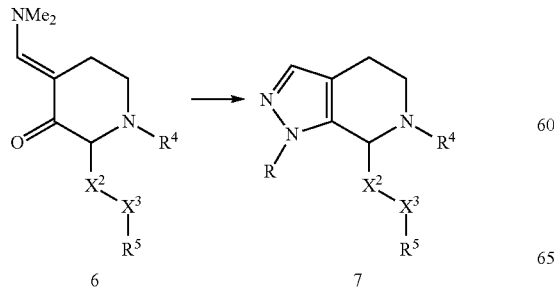

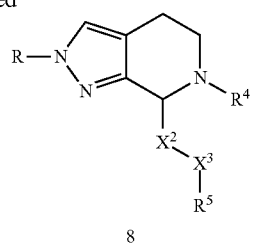

As shown in scheme 4, the intermediate of general formula 6 can be reacted with various nucleophiles of general formula H₂N—NH—R in an alcoholic solvent, preferably methanol or ethanol, at a temperature of about 20° to 80° C. to obtain the compounds of general formulae 7 and 8. In case of monosubstituted hydrazines regioisomeric products are formed.

The process depicted in scheme 5 is useful for obtaining 4,5,6,7-tetrahydroisoxazolo[3,4-c]pyridines of the present invention.

Scheme 5:

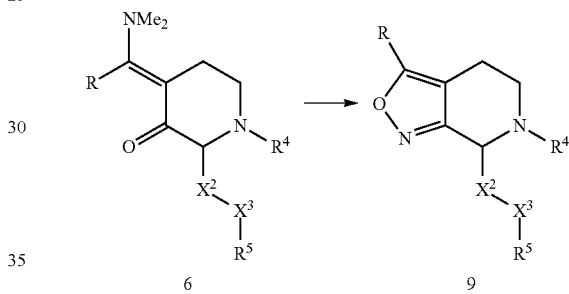

As shown in scheme 5, the intermediate of general formula 6 can be reacted with hydroxylamine under appropriate conditions to obtain compound of the general formula 9.

The process depicted in scheme 6 is useful for obtaining 5,6,7,8-tetrahydro-1,7-naphthyridines of the present invention.

Scheme 6:

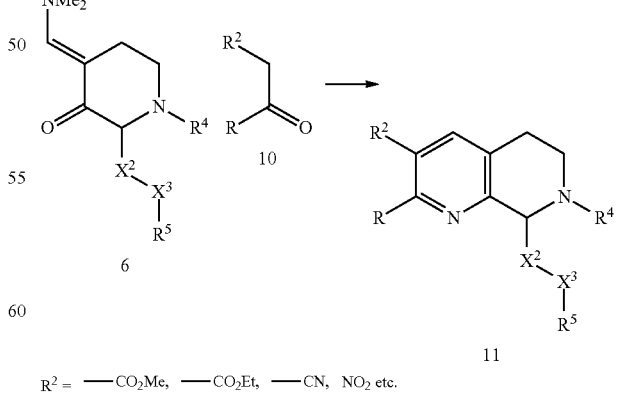

R² = —CO₂Me, —CO₂Et, —CN, NO₂ etc.

As shown in scheme 6, the condensation of compound of general formula 6 with the reagent of general formula 10 and ammonia acetate in refluxing acetic acid gives the compound of general formula 11. $R^2$ is —$CO_2Me$, —$CO_2Et$, —CN, $NO_2$, or the like.

The process depicted in scheme 7 is useful for obtaining 5,6,7,8-tetrahydro[3,4-d]pyrimidines of the present invention.

Scheme 7:

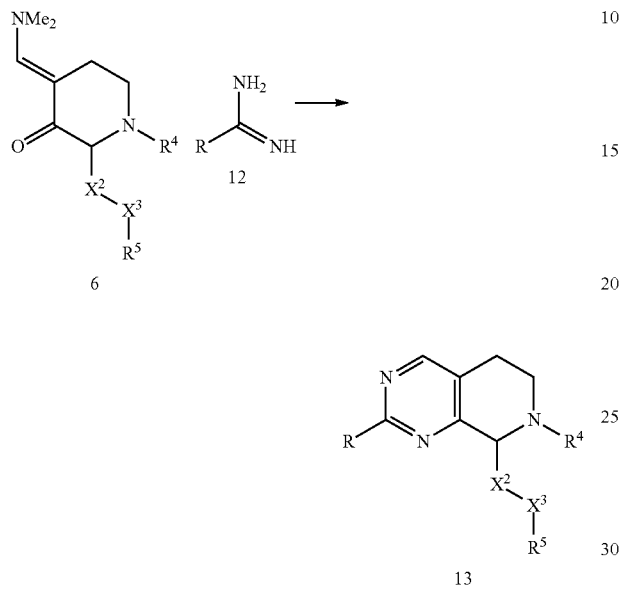

As shown in scheme 7, the cyclocondensation of the intermediate of general formula 6 with the 1,3-nucleophiles of general formula 12 in the presence of suitable organic or inorganic bases such as KOH, NaOH, NaHCO$_3$, sodium ethoxide, sodium methoxide, triethyl amine and diisopropyl ethyl amine in an alcoholic solvent, preferably ethanol or methanol, at a temperature of about 20° to 80° C. yields the compound of general formula 13.

The process depicted in scheme 8 is useful for obtaining 4,5,6,7-tetrahydrooxazolo[4,5-c]pyridines and 4,5,6,7-tetrahydrothiazolo[4,5-c]pyridines of the present invention.

Scheme 8:

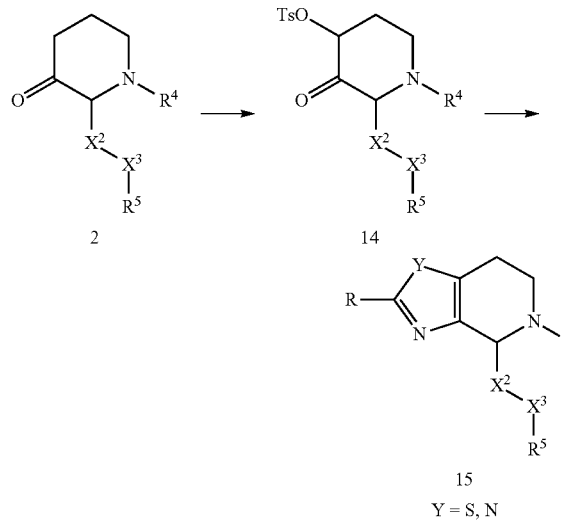

Y = S, N

As shown in scheme 8, the reaction of the compound of general formula 2 with standard agents, e.g. hydroxyl(tosyloxy)iodobenzene, gives the compound of formula 14 wherein Lg is a leaving group (e.g. tosylate, bromide, etc.). Reaction of the compound of general formula 14 with 1,3-nucleophiles under appropriate conditions yields the compound of general formula 15. Y is S or N.

The process depicted in scheme 9 is useful for obtaining 4,5,6,7-tetrahydro-1H-pyrrolo[2,3-c]pyridines of the present invention.

Scheme 9:

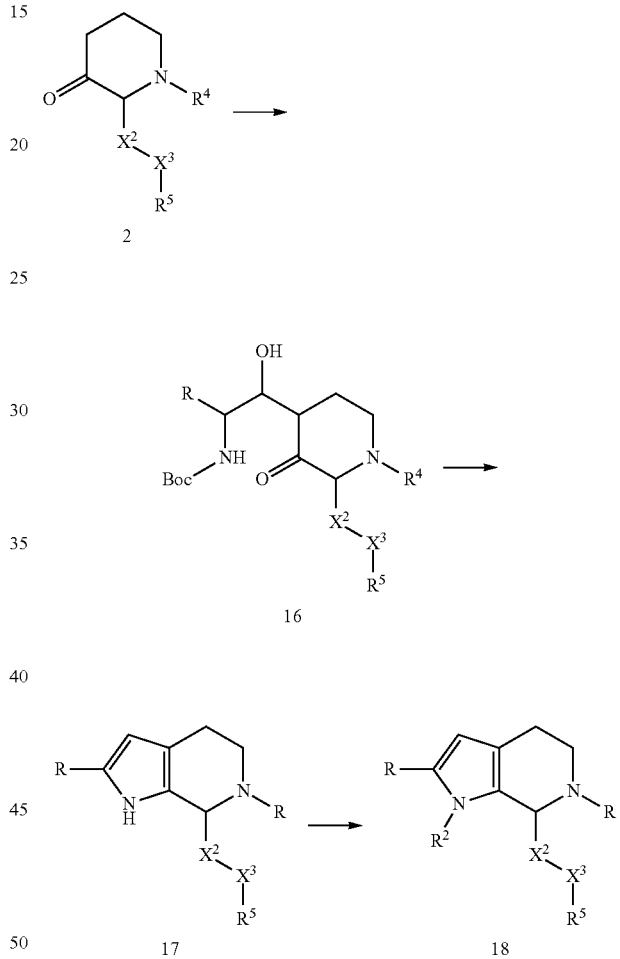

As shown in scheme 9, the reaction of the intermediate of general formula 2 with an optionally substituted aldehyde in presence of a suitable base such as alkyl lithium, LDA, LHMDS gives the intermediate of general formula 16. The intermediate of general formula 16 can be cyclised to the derivate of general formula 17 under suitable acidic conditions. The derivate of general formula 17 can be further functionalized to give the optionally substituted compound of general formula 18 using conventional chemical transformations.

The process depicted in scheme 10 is useful for obtaining 4,5,6,7-tetrahydrooxazolo[5,4-c]pyridines and 4,5,6,7-tetrahydrothiazolo[5,4-c]pyridines of the present invention.

Scheme 10:

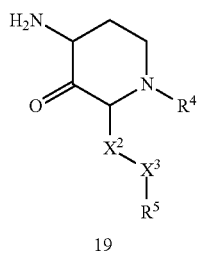
19

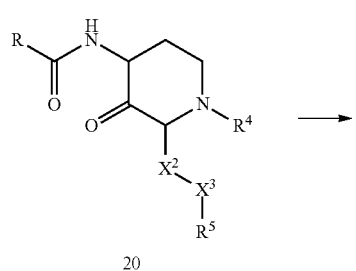
20

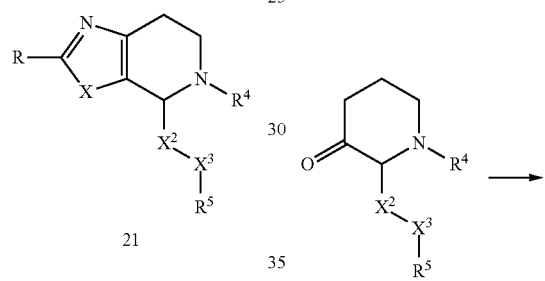
21

As shown in scheme 10, the reaction of intermediate of general formula 19 with an optionally substituted acid in presence of a standard coupling reagent (e.g. DCC, EDC, HATU, etc.) yields the intermediate of general formula 20. The intermediate of general formula 20 can be cyclised to the derivate of general formula 21 under suitable conditions using standard methodology (Lawesson's reagent, triphosgen). X is O or S.

The process depicted in scheme 11 is useful for obtaining 5,6,7,8-tetrahydropyrido[4,3-b]pyrazines of the present invention.

Scheme 11:

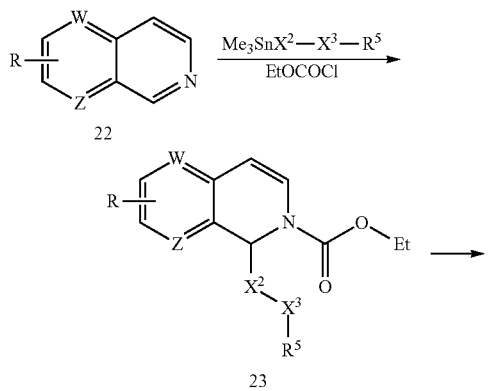

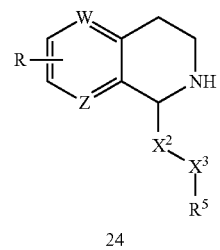
24

W = CH; Z = N
W = N; Z = CH

As shown in scheme 11, the reaction of the naphthyridine of general formula 22 with an optionally substituted stannane in the presence of ethylchloroformate gives the dihydronaphthyridine of general formula 23. Reduction of the olefin using conventional hydrogenation methods and removal of the protecting group gives the compound of general formula 24 (cf. Tetrahedron 2000, 41, 8053). W is CH and Z is N, or W is N and Z is CH.

The process depicted in scheme 12 is useful for obtaining 4,5,6,7-tetrahydrothieno[2,3-c]pyridines of the present invention.

Scheme 12

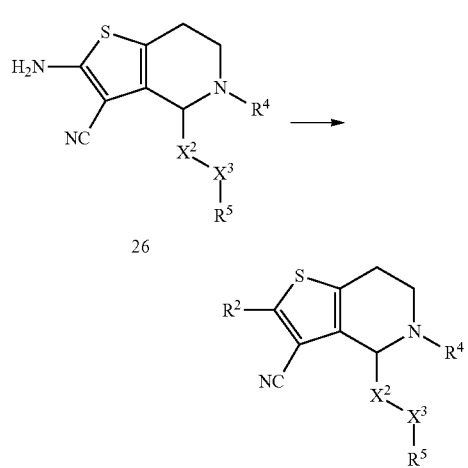

As shown in the scheme 12, the reaction of ketone of general formula 25 with malonic acid dinitrile in the presence of sulfur an a suitable base gives thiophenes of general formula 26. Conversion of the amino group by conventional reaction methods leads to thiophens of general formula 27. The thiophens of general formula 27 can be further functionalized to give optionally substituted compounds using conventional chemical transformations.

The processes depicted in schemes 13 and 14 are useful for obtaining 5,6,7,8-tetrahydrothiazolo[4,5-c]pyrazines of the present invention.

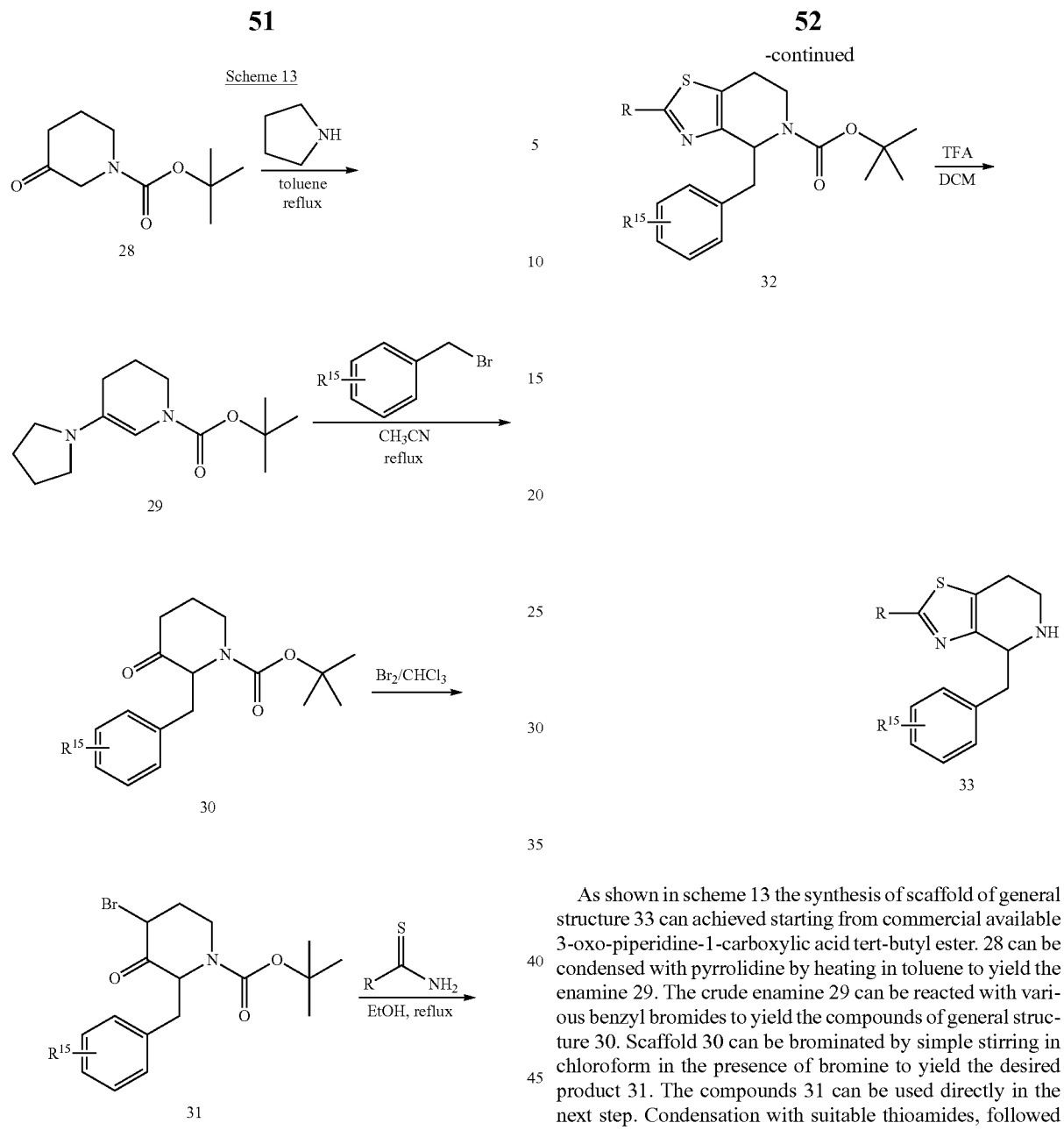

As shown in scheme 13 the synthesis of scaffold of general structure 33 can achieved starting from commercial available 3-oxo-piperidine-1-carboxylic acid tert-butyl ester. 28 can be condensed with pyrrolidine by heating in toluene to yield the enamine 29. The crude enamine 29 can be reacted with various benzyl bromides to yield the compounds of general structure 30. Scaffold 30 can be brominated by simple stirring in chloroform in the presence of bromine to yield the desired product 31. The compounds 31 can be used directly in the next step. Condensation with suitable thioamides, followed by acidic deprotection gives access to scaffold 33.

Scheme 14

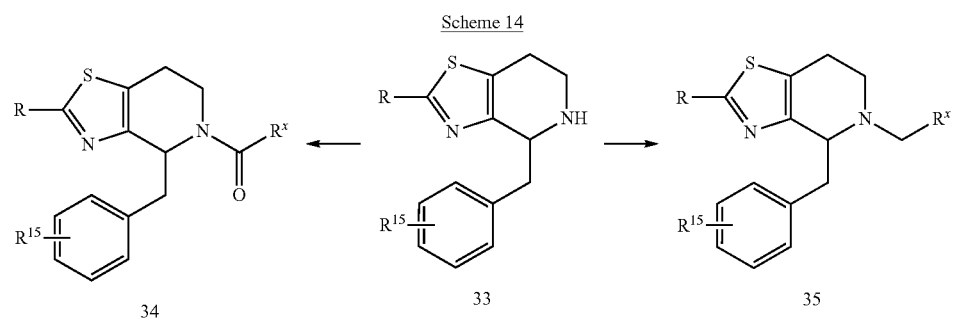

Scaffold 33 can easily be modified following the reaction outlined in scheme 14. Standard procedures like acylation or reductive amination using standard reaction protocols leads to scaffold of general structure 34 and 35.

In schemes 1 to 14, the variables R, $R^2$, $R^4$, $X^2$, $X^3$ and $R^5$ areas defined herein or represent a group that can be converted into the desired group, as shown in the following schemes 15 to 17.

Scheme 15:

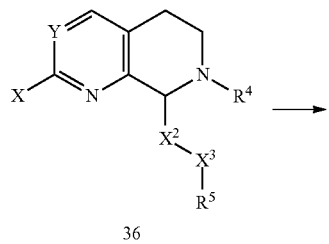

36

X = F, Br, Cl, —SO₂Me
Y = CH, N

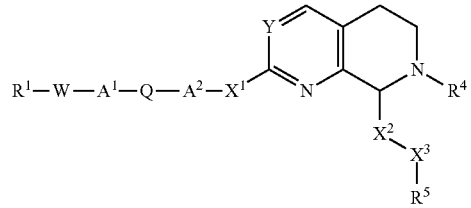

37
Y = CH, N

As shown in the scheme 15, the reaction of compounds of the general formula 36 with a suitable substituted nucleophile gives the compound of general formula 37.

Scheme 16:

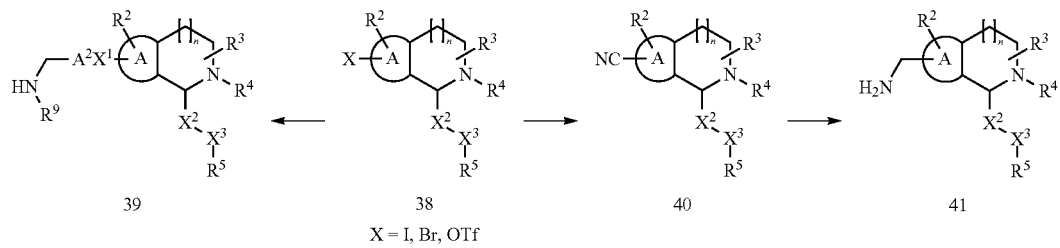

X = I, Br, OTf

As shown in the scheme 16, compounds of the general formula 38 give under standard Pd-cross coupling condition compounds of the general formula 38 and 40. Nitriles of general formula 40 give compounds of general formula 41 using standard reduction methods.

Scheme 17:

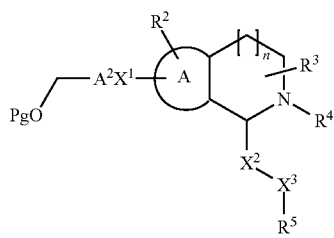

43

Pg = protecting group

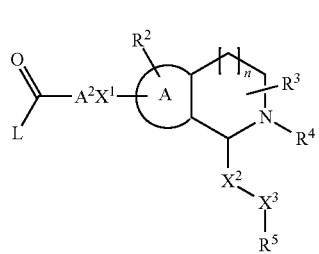

42
L = OH, OR, etc.

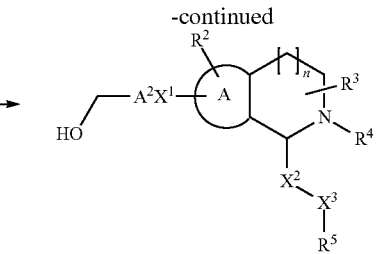

44

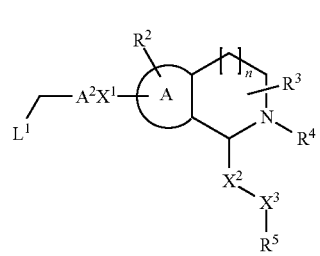

45

$L^1$ = I, Br, OTs, OMs, etc.

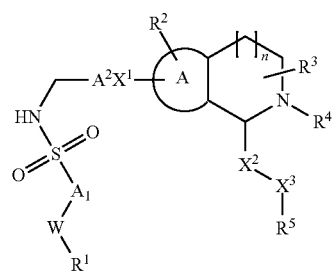

49

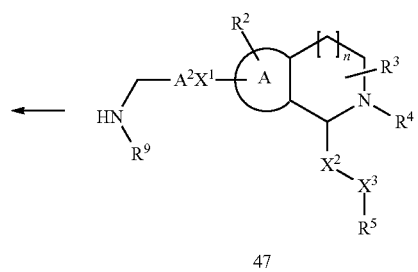

47

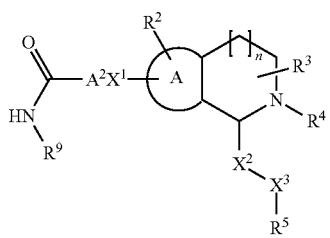

46
$L^2$ = CN, N$_3$

48

As shown in scheme 17, intermediates of general structure 44 give compounds of general structure 46 via introduction of a leaving group (halogen, tosylate, etc.) followed by nucleophilic replacement. Reduction of intermediates of general structure 46 and 48 gives compounds of general structure 47. The derivate of general formula 47 can be further functionalized to give the optionally substituted compound of general formula 49 using conventional chemical transformations.

The acid addition salts of the heterocyclic compounds of formula (I) are prepared in a customary manner by mixing the free base with a corresponding acid, optionally in solution in an organic solvent, for example a lower alcohol, such as methanol, ethanol or propanol, an ether, such as methyl tert-butyl ether or diisopropyl ether, a ketone, such as acetone or methyl ethyl ketone, or an ester, such as ethyl acetate.

The compounds of the formula (I) are capable of inhibiting the activity of glycine transporter, in particular glycine transporter 1 (GlyT1).

The utility of the compounds in accordance with the present invention as inhibiting the glycine transporter activity, in particular GlyT1 activity, may be demonstrated by methodology known in the art. For instance, human GlyT1c expressing recombinant hGlyT1c_5_CHO cells can be used for measuring glycine uptake and its inhibition ($IC_{50}$) by a compound of formula (I).

Amongst the compounds of the formula (I) those are preferred which achieve effective inhibition at low concentrations. In particular, compounds of the formula (I) are preferred which inhibit glycine transporter 1 (GlyT1) at a level of $IC_{50}$<1 µMol, more preferably at a level of $IC_{50}$<0.5 µMol, particularly preferably at a level of $IC_{50}$<0.2 µMol and most preferably at a level of $IC_{50}$<0.1 µMol.

The compounds of the formula (I) according to the present invention are thus useful as pharmaceuticals.

The present invention therefore also relates to pharmaceutical compositions which comprise an inert carrier and a compound of the formula (I).

The present invention also relates to the use of the compounds of the formula (I) in the manufacture of a medicament for inhibiting the glycine transporter GlyT1, and to corresponding methods of inhibiting the glycine transporter GlyT1.

The NMDA receptor is central to a wide range of CNS processes, and its role in a variety of diseases in humans or other species has been described. GlyT1 inhibitors slow the removal of glycine from the synapse, causing the level of synaptic glycine to rise. This in turn increases the occupancy of the glycine binding site on the NMDA receptor, which increases activation of the NMDA receptor following glutamate release from the presynaptic terminal. Glycine transport inhibitors and in particular inhibitors of the glycine trans-porter GlyT1 are thus known to be useful in treating a variety of neurologic and psychiatric disorders. Further, glycine A receptors play a role in a variety of diseases in humans or other species. Increasing extracellular glycine concentrations by inhibiting glycine trans-port may enhance the activity of glycine A receptors. Glycine transport inhibitors and in particular inhibitors of the glycine transporter GlyT1 are thus useful in treating a variety of neurologic and psychiatric disorders.

The present invention thus further relates to the use of the compounds of the formula (I) for the manufacture of a medicament for treating a neurologic or psychiatric disorder, and to corresponding methods of treating said disorders.

According to a particular embodiment, the disorder is associated with glycinergic or glutamatergic neurotransmission dysfunction.

According to a further particular embodiment, the disorder is one or more of the following conditions or diseases: schizophrenia or a psychotic disorder including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder, including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or cognitive impairment including age related cognitive decline; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); obesity, bulimia nervosa and compulsive eating disorders; bipolar disorders, mood disorders including depressive disorders; depression including unipolar depression, seasonal depression and post-partum depression, premenstrual syndrome (PMS) and premenstrual dysphoric disorder (PDD), mood disorders due to a general medical condition, and substance-induced mood disorders; learning disorders, pervasive developmental disorder including autistic disorder, attention deficit disorders including attention-deficit hyperactivity disorder (ADHD) and conduct disorder; movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, muscular spasms and disorders associated with muscular spasticity or weakness including tremors; dyskinesias [including tremor (such as rest tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writers cramp and hemiplegic dystonia)]; urinary incontinence; neuronal damage including ocular damage, retinopathy or macular degeneration of the eye, tinnitus, hearing impairment and loss, and brain edema; emesis; and sleep disorders including insomnia and narcolepsy.

According to a further particular embodiment, the disorder is pain, in particular chronic pain and especially neuropathic pain.

Pain can be classified as acute and chronic pain. Acute pain and chronic pain differ in their etiology, pathophysiology, diagnosis and treatment.

Acute pain, which occurs following tissue injury, is self-limiting, serves as an alert to ongoing tissue damage and following tissue repair it will usually subside. There are minimal psychological symptoms associated with acute pain apart from mild anxiety. Acute pain is nociceptive in nature and occurs following chemical, mechanical and thermal stimulation of A-delta and C-polymodal pain receptors.

Chronic pain, on the other hand, serves no protective biological function. Rather than being the symptom of tissue damage it is a disease in its own right. Chronic pain is unrelenting and not self-limiting and can persist for years, perhaps decades after the initial injury. Chronic pain can be refractory to multiple treatment regimes. Psychological symptoms associated with chronic pain include chronic anxiety, fear, depression, sleeplessness and impairment of social interaction. Chronic non-malignant pain is predominantly neuropathic in nature and involves damage to either the peripheral or central nervous systems.

Acute pain and chronic pain are caused by different neurophysiological processes and therefore tend to respond to different types of treatments. Acute pain can be somatic or visceral in nature. Somatic pain tends to be a well localised, constant pain and is described as sharp, aching, throbbing or gnawing. Visceral pain, on the other hand, tends to be vague in distribution, paroxysmal in nature and is usually described as deep, aching, squeezing or colicky in nature. Examples of acute pain include post-operative pain, pain associated with trauma and the pain of arthritis. Acute pain usually responds to treatment with opioids or non-steroidal anti-inflammatory drugs.

Chronic pain, in contrast to acute pain, is described as burning, electric, tingling and shooting in nature. It can be continuous or paroxysmal in presentation. The hallmarks of chronic pain are chronic allodynia and hyperalgesia. Allodynia is pain resulting from a stimulus that normally does not ellicit a painful response, such as a light touch. Hyperalgesia is an increased sensitivity to normally painful stimuli. Primary hyperalgesia occurs immediately within the area of the injury. Secondary hyperalgesia occurs in the undamaged area surrounding the injury. Examples of chronic pain include complex regional pain syndrome, pain arising from peripheral neuropathies, post-operative pain, chronic fatigue syndrome pain, tension-type headache, pain arising from mechanical nerve injury and severe pain associated with diseases such as cancer, metabolic disease, neurotropic viral disease, neurotoxicity, inflammation, multiple sclerosis or any pain arising as a consequence of or associated with stress or depressive illness.

Although opioids are cheap and effective, serious and potentially life-threatening side effects occur with their use, most notably respiratory depression and muscle rigidity. In addition the doses of opioids which can be administered are limited by nausea, emesis, constipation, pruritis and urinary retention, often resulting in patients electing to receive sub-optimal pain control rather than suffer these distressing side-effects. Furthermore, these side-effects often result in patients requiring extended hospitalisation. Opioids are highly addictive and are scheduled drugs in many territories.

The compounds of formula (I) are particularly useful in the treatment of schizophrenia, bipolar disorder, depression including unipolar depression, seasonal depression and post-partum depression, premenstrual syndrome (PMS) and pre-menstrual dysphoric disorder (PDD), learning disorders, pervasive developmental disorder including autistic disorder, attention deficit disorders including Attention-Deficit/Hyperactivity Disorder, tic disorders including Tourette's disorder, anxiety disorders including phobia and post traumatic stress disorder, cognitive disorders associated with dementia, AIDS dementia, Alzheimer's, Parkinson's, Huntington's disease, spasticity, myoclonus, muscle spasm, tinnitus and hearing impairment and loss are of particular importance.

Particular cognitive disorders are dementia, delirium, amnestic disorders and cognitive impairment including age-related cognitive decline.

Particular anxiety disorders are generalized anxiety disorder, obsessive-compulsive disorder and panic attack.

Particular schizophrenia or psychosis pathologies are paranoid, disorganized, catatonic or undifferentiated schizophrenia and substance-induced psychotic disorder.

Particular neurologic disorders that can be treated with the compounds of the formula (I) include in particular a cognitive disorder such as dementia, cognitive impairment, attention deficit hyperactivity disorder.

Particular psychiatric disorders that can be treated with the compounds of the formula (I) include in particular an anxiety disorder, a mood disorder such as depression or a bipolar disorder, schizophrenia, a psychotic disorder.

Within the context of the treatment, the use according to the invention of the compounds of the formula (I) involves a method. In this method, an effective quantity of one or more compounds or the formula (I), as a rule formulated in accordance with pharmaceutical and veterinary practice, is administered to the individual to be treated, preferably a mammal, in particular a human being. Whether such a treatment is indicated, and in which form it is to take place, depends on the individual case and is subject to medical assessment (diagnosis) which takes into consideration signs, symptoms and/or malfunctions which are present, the risks of developing particular signs, symptoms and/or malfunctions, and other factors.

As a rule, the treatment is effected by means of single or repeated daily administration, where appropriate together, or alternating, with other drugs or drug-containing preparations.

The invention also relates to the manufacture of pharmaceutical compositions for treating an individual, preferably a mammal, in particular a human being. Thus, the compounds of the formula (I) are customarily administered in the form of pharmaceutical compositions which comprise an inert carrier (e.g. a pharmaceutically acceptable excipient) together with at least one compound according to the invention and, where appropriate, other drugs. These compositions can, for example, be administered orally, rectally, transdermally, subcutaneously, intravenously, intramuscularly or intranasally.

Examples of suitable pharmaceutical formulations are solid medicinal forms, such as powders, granules, tablets, in particular film tablets, lozenges, sachets, cachets, sugar-coated tablets, capsules, such as hard gelatin capsules and soft gelatin capsules, suppositories or vaginal medicinal forms, semisolid medicinal forms, such as ointments, creams, hydrogels, pastes or plasters, and also liquid medicinal forms, such as solutions, emulsions, in particular oil-in-water emulsions, suspensions, for example lotions, injection preparations and infusion preparations, and eyedrops and eardrops. Implanted release devices can also be used for administering inhibitors according to the invention. In addition, it is also possible to use liposomes or microspheres.

When producing the compositions, the compounds according to the invention are optionally mixed or diluted with one or more carriers (excipients). Carriers (excipients) can be solid, semisolid or liquid materials which serve as vehicles, carriers or medium for the active compound.

Suitable carriers (excipients) are listed in the specialist medicinal monographs. In addition, the formulations can comprise pharmaceutically acceptable auxiliary substances, such as wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik and angrenzende Gebiete [Encyclopedia of auxiliary substances for pharmacy, cosmetics and related fields], $4^{th}$ edition, Aulendorf: ECV-Editio-Cantor-Verlag, 1996.

The compounds of formula (I) may also be suitable for combination with other therapeutic agents.

Thus, the present invention also provides:
i) a combination comprising a compound of formula (I) with one or more further therapeutic agents;
ii) a pharmaceutical composition comprising a combination product as defined in i) above and at least one carrier, diluent or excipient;
iii) the use of a combination as defined in i) above in the manufacture of a medicament for treating or preventing a disorder, disease or condition as defined herein;
iv) a combination as defined in i) above for use in treating or preventing a disorder, disease or condition as defined herein;
v) a kit-of-parts for use in the treatment of a disorder, disease or condition as defined herein, comprising a first dosage form comprising a compound of formula (I) and one or more further dosage forms each comprising one or more further therapeutic agents for simultaneous therapeutic administration,
vi) a combination as defined in i) above for use in therapy;
vii) a method of treatment or prevention of a disorder, disease or condition as defined herein comprising administering an effective amount of a combination as defined in i) above;

viii) a combination as defined in i) above for treating or preventing a disorder, disease or condition as defined herein.

The combination therapies of the invention may be administered adjunctively. By adjunctive administration is meant the coterminous or overlapping administration of each of the components in the form of separate pharmaceutical compositions or devices. This regime of therapeutic administration of two or more therapeutic agents is referred to generally by those skilled in the art and herein as adjunctive therapeutic administration; it is also known as add-on therapeutic administration. Any and all treatment regimes in which a patient receives separate but coterminous or overlapping therapeutic administration of the compounds of formula (I) and at least one further therapeutic agent are within the scope of the current invention. In one embodiment of adjunctive therapeutic administration as described herein, a patient is typically stabilised on a therapeutic administration of one or more of the components for a period of time and then receives administration of another component.

The combination therapies of the invention may also be administered simultaneously. By simultaneous administration is meant a treatment regime wherein the individual components are administered together, either in the form of a single pharmaceutical composition or device comprising or containing both components, or as separate compositions or devices, each comprising one of the components, administered simultaneously. Such combinations of the separate individual components for simultaneous combination may be provided in the form of a kit-of-parts.

In a further aspect, the invention provides a method of treatment of a psychotic disorder by adjunctive therapeutic administration of compounds of formula (I) to a patient receiving therapeutic administration of at least one antipsychotic agent. In a further aspect, the invention provides the use of compounds of formula (I) in the manufacture of a medicament for adjunctive therapeutic administration for the treatment of a psychotic disorder in a patient receiving therapeutic administration of at least one antipsychotic agent. The invention further provides compounds of formula (I) for use for adjunctive therapeutic administration for the treatment of a psychotic disorder in a patient receiving therapeutic administration of at least one antipsychotic agent.

In a further aspect, the invention provides a method of treatment of a psychotic disorder by adjunctive therapeutic administration of at least one antipsychotic agent to a patient receiving therapeutic administration of compounds of formula (I). In a further aspect, the invention provides the use of at least one antipsychotic agent in the manufacture of a medicament for adjunctive therapeutic administration for the treatment of a psychotic disorder in a patient receiving therapeutic administration of compounds of formula (I). The invention further provides at least one antipsychotic agent for adjunctive therapeutic administration for the treatment of a psychotic disorder in a patient receiving therapeutic administration of compounds of formula (I).

In a further aspect, the invention provides a method of treatment of a psychotic disorder by simultaneous therapeutic administration of compounds of formula (I) in combination with at least one antipsychotic agent. The invention further provides the use of a combination of compounds of formula (I) and at least one antipsychotic agent in the manufacture of a medicament for simultaneous therapeutic administration in the treatment of a psychotic disorder. The invention further provides a combination of compounds of formula (I) and at least one antipsychotic agent for simultaneous therapeutic administration in the treatment of a psychotic disorder. The invention further provides the use of compounds of formula (I) in the manufacture of a medicament for simultaneous therapeutic administration with at least one antipsychotic agent in the treatment of a psychotic disorder. The invention further provides compounds of formula (I) for use for simultaneous therapeutic administration with at least one antipsychotic agent in the treatment of a psychotic disorder. The invention further provides the use of at least one antipsychotic agent in the manufacture of a medicament for simultaneous therapeutic administration with compounds of formula (I) in the treatment of a psychotic disorder. The invention further provides at least one antipsychotic agent for simultaneous therapeutic administration with compounds of formula (I) in the treatment of a psychotic disorder.

In further aspects, the invention provides a method of treatment of a psychotic disorder by simultaneous therapeutic administration of a pharmaceutical composition comprising compounds of formula (I) and at least one mood stabilising or antimanic agent, a pharmaceutical composition comprising compounds of formula (I) and at least one mood stabilising or antimanic agent, the use of a pharmaceutical composition comprising compounds of formula (I) and at least one mood stabilising or antimanic agent in the manufacture of a medicament for the treatment of a psychotic disorder, and a pharmaceutical composition comprising compounds of formula (I) and at least one mood stabilising or antimanic agent for use in the treatment of a psychotic disorder.

Antipsychotic agents include both typical and atypical antipsychotic drugs. Examples of antipsychotic drugs that are useful in the present invention include, but are not limited to: butyrophenones, such as haloperidol, pimozide, and droperidol; phenothiazines, such as chlorpromazine, thioridazine, mesoridazine, trifluoperazine, perphenazine, fluphenazine, thiflupromazine, prochlorperazine, and acetophenazine; thioxanthenes, such as thiothixene and chlorprothixene; thienobenzodiazepines; dibenzodiazepines; benzisoxazoles; dibenzothiazepines; imidazolidinones; benziso-thiazolyl-piperazines; triazine such as lamotrigine; dibenzoxazepines, such as loxapine; dihydroindolones, such as molindone; aripiprazole; and derivatives thereof that have antipsychotic activity.

Examples of tradenames and suppliers of selected antipsychotic drugs are as follows: clozapine (available under the tradename CLOZARIL®, from Mylan, Zenith Goldline, UDL, Novartis); olanzapine (available under the tradename ZYPREX®, from Lilly); ziprasidone (available under the tradename GEODON®, from Pfizer); risperidone (available under the tradename RISPERDAL®, from Janssen); quetiapine fumarate (available under the tradename SEROQUEL®, from AstraZeneca); haloperidol (available under the tradename HALDOL®, from Ortho-McNeil); chlorpromazine (available under the tradename THORAZINE®, from SmithKline Beecham (GSK)); fluphenazine (available under the tradename PROLIXIN®, from Apothecon, Copley, Schering, Teva, and American Pharmaceutical Partners, Pasadena); thiothixene (available under the tradename NAVANE®, from Pfizer); trifluoperazine (10-[3-(4-methyl-1-piperazinyl)propyl]-2-(trifluoromethyl)phenothiazine dihydrochloride, available under the tradename STELAZINE®, from Smith Klein Beckman); perphenazine (available under the tradename TRILAFON®; from Schering); thioridazine (available under the tradename MELLARIL®; from Novartis, Roxane, HiTech, Teva, and Alpharma); molindone (available under the tradename MOBAN®, from Endo); and loxapine (available under the tradename LOXITANE (D; from Watson). Furthermore, benperidol (Glianimon®), perazine (Taxilan®) or melperone (Eunerpan®) may be used. Other antipsychotic drugs include promazine (available under the tradename SPARINE®), triflurpromazine (available under the tradename VESPRIN®), chlorprothixene (available under the tradename TARACTAN®), droperidol (available under the tradename INAPSINE®), acetophenazine (available under the tradename TINDAL®), prochlorperazine (available under the tradename COMPAZINE®), methotrimeprazine (available under the tradename NOZINAN®), pipotiazine (available under the tradename PIPOTRIL®), ziprasidone, and hoperidone.

In a further aspect, the invention provides a method of treatment of a neurodegenerative disorder such as Alzheimer Disease by adjunctive therapeutic administration of compounds of formula (I) to a patient receiving therapeutic administration of at least one agent suitable for the treatment of a neurodegenerative disorder such as Alzheimer Disease. In a further aspect, the invention provides the use of compounds of formula (I) in the manufacture of a medicament for adjunctive therapeutic administration for the treatment of a neurodegenerative disorder such as Alzheimer Disease in a patient receiving therapeutic administration of at least one agent suitable for the treatment of a neurodegenerative disorder such as Alzheimer Disease. The invention further provides compounds of formula (I) for use for adjunctive therapeutic administration for the treatment of a neurodegenerative disorder such as Alzheimer Disease in a patient receiving therapeutic administration of at least one agent suitable for the treatment of a neurodegenerative disorder such as Alzheimer Disease.

In a further aspect, the invention provides a method of treatment of a neurodegenerative disorder such as Alzheimer Disease by adjunctive therapeutic administration of at least one agent suitable for the treatment of a neurodegenerative disorder such as Alzheimer Disease to a patient receiving therapeutic administration of compounds of formula (I). In a further aspect, the invention provides the use of at least one agent suitable for the treatment of a neurodegenerative disorder such as Alzheimer Disease in the manufacture of a medicament for adjunctive therapeutic administration for the treatment of a neurodegenerative disorder such as Alzheimer Disease in a patient receiving therapeutic administration of compounds of formula (I). The invention further provides at least one agent suitable for the treatment of a neurodegenerative disorder such as Alzheimer Disease for adjunctive therapeutic administration for the treatment of a neurodegenerative disorder such as Alzheimer Disease in a patient receiving therapeutic administration of compounds of formula (I).

In a further aspect, the invention provides a method of treatment of a neurodegenerative disorder such as Alzheimer Disease by simultaneous therapeutic administration of compounds of formula (I) in combination with at least one agent suitable for the treatment of a neurodegenerative disorder such as Alzheimer Disease. The invention further provides the use of a combination of compounds of formula (I) and at least one agent suitable for the treatment of a neurodegenerative disorder such as Alzheimer Disease in the manufacture of a medicament for simultaneous therapeutic administration in the treatment of a neurodegenerative disorder such as Alzheimer Disease. The invention further provides a combination of compounds of formula (I) and at least one agent suitable for the treatment of a neurodegenerative disorder such as Alzheimer Disease for simultaneous therapeutic administration in the treatment of a neurodegenerative disorder such as Alzheimer Disease. The invention further provides the use of compounds of formula (I) in the manufacture of a medicament for simultaneous therapeutic administration with at least one agent suitable for the treatment of a neurodegenerative disorder such as Alzheimer Disease in the treatment of a neurodegenerative disorder such as Alzheimer Disease. The invention further provides compounds of formula (I) for use for simultaneous therapeutic administration with at least one agent suitable for the treatment of a neurodegenerative disorder such as Alzheimer Disease in the treatment of a neurodegenerative disorder such as Alzheimer Disease. The invention further provides the use of at least one agent suitable for the treatment of a neurodegenerative disorder such as Alzheimer Disease in the manufacture of a medicament for simultaneous therapeutic administration with compounds of formula (I) in the treatment of a neurodegenerative disorder such as Alzheimer Disease. The invention further provides at least one agent suitable for the treatment of a neurodegenerative disorder such as Alzheimer Disease for simultaneous therapeutic administration with compounds of formula (I) in the treatment of a neurodegenerative disorder such as Alzheimer Disease.

Examples of agents suitable for the treatment of a neurodegenerative disorder such as Alzheimer Disease that are useful in the present invention include, but are not limited to: cholinesterase inhibitors, agents targeting nicotinic or muscarinic acetylcholine receptors, NMDA receptors, amyloid formation, mitochondrial dysfunctions, disease associated calpain activity, neuroinflamation, tumor necrosis factor receptors, NF-kappaB, peroxisome proliferator activator receptor gamma, Apolipoprotein E variant 4 (ApoE4), disease-associated increase of the HPA axis, epileptic discharges, vascular dysfunction, vascular risk factors, and oxidative stress.

Suitable cholinesterase inhibitors which may be used in combination with the compounds of the inventions include for example tacrine, donepezil, galantamine and rivastigmine.

Suitable NMDA receptors targeting agents which may be used in combination with the compounds of the inventions include for example memantine.

Suitable agents affecting increased HPA axis activity which may be used in combination with the compounds of the inventions include for example CRF1 antagonists or V1 b antagonists.

In a further aspect therefore, the invention provides a method of treatment of pain by adjunctive therapeutic administration of compounds of formula (I) to a patient receiving therapeutic administration of at least one agent suitable for the treatment of pain. In a further aspect, the invention provides the use of compounds of formula (I) in the manufacture of a medicament for adjunctive therapeutic administration for the treatment of pain in a patient receiving therapeutic administration of at least one agent suitable for the treatment of pain. The invention further provides compounds of formula (I) for use for adjunctive therapeutic administration for the treatment of pain in a patient receiving therapeutic administration of at least one agent suitable for the treatment of pain.

In a further aspect, the invention provides a method of treatment of pain by adjunctive therapeutic administration of at least one agent suitable for the treatment of pain to a patient receiving therapeutic administration of compounds of formula (I). In a further aspect, the invention provides the use of at least one agent suitable for the treatment of pain in the manufacture of a medicament for adjunctive therapeutic administration for the treatment of pain in a patient receiving therapeutic administration of compounds of formula (I). The invention further provides at least one agent suitable for the treatment of pain for adjunctive therapeutic administration for the treatment of pain in a patient receiving therapeutic administration of compounds of formula (I).

In a further aspect, the invention provides a method of treatment of pain by simultaneous therapeutic administration of compounds of formula (I) in combination with at least one agent suitable for the treatment of pain. The invention further provides the use of a combination of compounds of formula (I) and at least one agent suitable for the treatment of pain in the manufacture of a medicament for simultaneous therapeutic administration in the treatment of pain. The invention further provides a combination of compounds of formula (I) and at least one agent suitable for the treatment of pain for simultaneous therapeutic administration in the treatment of pain. The invention further provides the use of compounds of formula (I) in the manufacture of a medicament for simultaneous therapeutic administration with at least one agent suitable for the treatment of pain in the treatment of pain. The invention further provides compounds of formula (I) for use for simultaneous therapeutic administration with at least one agent suitable for the treatment of pain in the treatment of pain. The invention further provides the use of at least one agent suitable for the treatment of pain in the manufacture of a medicament for simultaneous therapeutic administration with compounds of formula (I) in the treatment of pain. The invention further provides at least one agent suitable for the treatment of pain for simultaneous therapeutic administration with compounds of formula (I) in the treatment of pain.

Examples of agents suitable for the treatment of pain that are useful in the present invention include, but are not limited to: NSAIDs (Nonsteroidal Antiinflammatory Drugs), anticonvulsant drugs such as carbamazepine and gabapentin, sodium channel blockers, anti-depressant drugs, cannabinoids and local anaesthetics.

Suitable agents used in combination with the compounds of the inventions include for example celecoxib, etoricoxib, lumiracoxib, paracetamol, tramadol, methadone, venlafaxine, imipramine, duloxetine, bupropion, gabapentin, pregabalin, lamotrigine, fentanyl, parecoxib, nefopam, remifentanil, pethidine, diclofenac, rofecoxib, nalbuphine, sufentanil, pethidine, diamorphine and butorphanol.

It will be appreciated by those skilled in the art that the compounds according to the invention may advantageously be used in conjunction with one or more other therapeutic agents, for instance, antidepressant agents such as 5HT3 antagonists, serotonin agonists, NK-1 antagonists, selective serotonin reuptake inhibitors (SSRI), noradrenaline re-uptake inhibitors (SNRI), tricyclic antidepressants, dopaminergic antidepressants, H3 antagonists, 5HT1A antagonists, 5HT1 B antagonists, 5HT1 D antagonists, D1 agonists, M1 agonists and/or anticonvulsant agents, as well as cognitive enhancers.

Suitable 5HT3 antagonists which may be used in combination of the compounds of the inventions include for example ondansetron, granisetron, metoclopramide.

Suitable serotonin agonists which may be used in combination with the compounds of the invention include sumatriptan, rauwolscine, yohimbine, metoclopramide.

Suitable SSRIs which may be used in combination with the compounds of the invention include fluoxetine, citalopram, femoxetine, fluvoxamine, paroxetine, indalpine, sertraline, zimeldine.

Suitable SNRIs which may be used in combination with the compounds of the invention include venlafaxine and reboxetine.

Suitable tricyclic antidepressants which may be used in combination with a compound of the invention include imipramine, amitriptiline, chlomipramine and nortriptiline.

Suitable dopaminergic antidepressants which may be used in combination with a compound of the invention include bupropion and aminepine.

Suitable anticonvulsant agents which may be used in combination of the compounds of the invention include for example divalproex, carbamazepine and diazepam.

The following examples serve to explain the invention without limiting it.

The compounds were characterized by mass spectrometry, generally recorded via HPLC-MS in a fast gradient on C18-material (electrospray-ionisation (ESI) mode).

PREPARATION EXAMPLES

Intermediates

Intermediate 1

1-(4-Chlorophenyl)cyclobutanecarbaldehyde

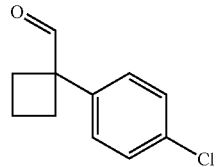

Chemical Formula: $C_{11}H_{11}ClO$
Exact Mass: 194.05

To a solution of 1-(4-chlorophenyl)cyclobutanecarbonitrile (36.2 g; 190 mmol) in toluene (500 ml) was added DiBAL-H (230 ml; 1 M; 1.2 eq) at −78° C. The mixture was stirred at −78° C. for 2 h. The cool mixture was added under vigorous stirring to HCl (2 M; 400 ml). The organic phase was separated, washed with HCl (2 M), water, brine, dried over $MgSO_4$ and evaporated. The crude product (34 g; 175 mmol; 92%) was used without further purification.

Intermediate 2

6-(1-(4-Chlorophenyl)cyclobutyl)-5-nitropiperidin-2-one

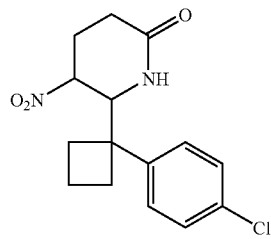

Chemical Formula: $C_{15}H_{17}ClN_2O_3$
Exact Mass: 308.09

A mixture of intermediate 1 (30 g; 154 mmol), methyl 4-nitrobutyrate (1 eq; 154 mmol; 19 ml) and ammonium acetate (2 eq; 300 mmol; 24 g) in ethanol (65 ml) was heated in the micro wave for 2 h. The mixture was diluted with EtOAc and washed with saturated Na—$HCO_3$ solution, water and brine, dried over $MgSO_4$ and evaporated. The residue was rinsed with n-heptan to yield a pale yellow solid. The product (29 g; 64%) was used without further purification.

ESI-MS [M+H$^+$]=309 Calculated for $C_{15}H_{17}ClN_2O_3$=308

Intermediate 3

2-(1-(4-Chlorophenyl)cyclobutyl)-3-nitropiperidine

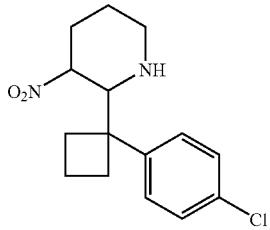

Chemical Formula: $C_{15}H_{19}ClN_2O_2$
Exact Mass: 294.11

A mixture of intermediate 2 (30 g; 97 mmol) and boran dimethylsulfid complex (1.6 eq; 15 ml) in THF was heated under reflux for 48 h. The reaction was cooled to room temperature and quenched by addition of aqueous NaOH solution. The phases were separated and the organic layer was washed with aqueous NaOH, water and brine, dried over MgSO$_4$ and evaporated. The crude product (25 g; 87%) was used without further purification.

ESI-MS [M+H$^+$]=295 Calculated for $C_{13}H_{13}ClN_2O_2$=294

Intermediate 4

2-(1-(4-Chlorophenyl)cyclobutyl)piperidin-3-one

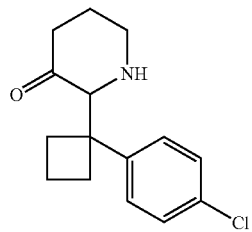

Chemical Formula: $C_{15}H_{18}ClNO$
Exact Mass: 263.11

A mixture of intermediate 3 (10 g; 35 mmol) and KOH (15 g; 280 mmol; 8 eq) in ethanol/water (100 ml; 1/1) was heated for 30 min at 40° C. To this solution was added a solution of TiCl$_3$ (10% in HCl; 170 mmol; 5 eq) and ammonium acetate (40 g; 500 mmol; 15 eq) in water at 40° C. The mixture was stirred for additional 2 h at 40° C. The cooled mixture was partitioned between EtOAc and HCl. The phases were separated and the aqueous layer was extracted with EtOAc. The combined organic layers were washed with saturated NaHCO$_3$ solution, water and brine, dried over MgSO$_4$ and evaporated. The crude intermediate (9.5 g; 106%) was used for the next step without further purification.

Intermediate 5 tert-Butyl 2-(1-(4-chlorophenyl)cyclobutyl)-3-oxopiperidine-1-carboxylate

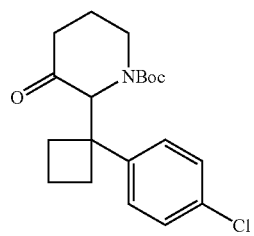

Chemical Formula: $C_{20}H_{26}ClNO_3$
Exact Mass: 363.16

A mixture of intermediate 4 (10.5 g; 40 mmol), diisopropyl ethylamine (1.2 eq; 8 ml) and Boc$_2$O (1.1 eq; 9 g) in acetonitrile was stirred at 65° C. for 5 h. The cooled mixture was diluted with EtOAc and washed with HCl, water and brine, dried over MgSO$_4$ and evaporated. The residue was purified by silica gel column chromatography to give the product (8.8 g; 61%) as colorless oil.

ESI-MS [M+Na$^{30}$]=386 Calculated for $C_{22}H_{25}ClNaNO_3$=386

Intermediate 6

(E)-tert-Butyl 2-(1-(4-chlorophenyl)cyclobutyl)-4-((dimethylamino)methylene)-3-oxopiperidine-1-carboxylate

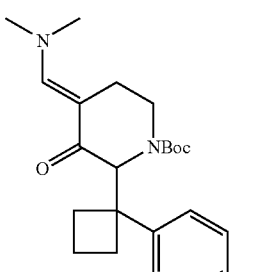

Chemical Formula: $C_{23}H_{31}ClN_2O_3$
Exact Mass: 418.2

A mixture of intermediate 5 (3.24 g; 8.9 mmol) and Bredereck's reagent (1.25 eq; 2.3 ml; 11 mmol) in toluene (90 ml) was stirred at 120° C. in the micro wave. The mixture was diluted with EtOAc and was washed with water and brine, dried over MgSO$_4$ and evaporated. The residue was purified by silica gel column chromatography using EtOAc/heptane (1/1) to give the product (2.95 g; 79%) as pale yellow foam.

ESI-MS [M+H$^+$]=419 Calculated for $C_{23}H_{31}ClN_2O_3$=418

Intermediate 7

8-(1-(4-Chlorophenyl)cyclobutyl)-5,6,7,8-tetrahydropyrido[3,4-d]pyrimidine hydrochloride

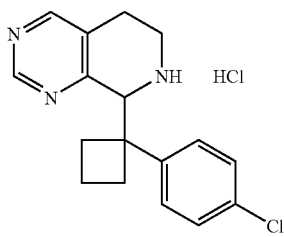

Chemical Formula: $C_{17}H_{18}ClN_3$
Exact Mass: 299.12

7.1 Step A

Intermediate 6 (100 mg; 0.275 mmol) and formadine acetate (86 mg; 3 eq) were dissolved in toluene and heated at 100° C. until complete conversation. The mixture was concentrated and the residue was dissolved in EtOAc and $H_2O$. The organic layer was washed with saturated $NaHCO_3$ solution, brine, dried over $MgSO_4$ and concentrated. The residue was purified by PTLC to give the product (32 mg; 29%) as colorless oil.

7.2 Step B

The product of step A was dissolved in 5 N isopropanolic hydrochloric acid (1 ml) and stirred for 2 h at room temperature. The solvents were evaporated and the product was dried in vacuo.

ESI-MS $[M+H^+]$=300 Calculated for $C_{17}H_{18}ClN_3$=299

Intermediate 8 tert-Butyl 7-(1-(4-chlorophenyl)cyclobutyl)-1-(2-hydroxyethyl)-4,5-dihydro-1H-pyrazolo[3,4-c]pyridine-6(7H)-carboxylate

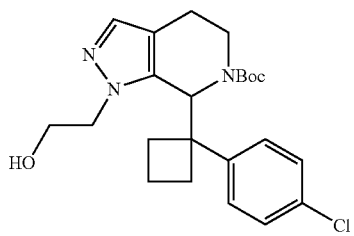

Chemical Formula: $C_{23}H_{30}ClN_3O_3$
Exact Mass: 431.2

A mixture of intermediate 6 (0.78 g; 2.15 mmol) and 2-hydrazinylethanol (1.25 eq; 0.2 g) in ethanol (2.5 ml) was stirred at 80° C. for 1 h. Ethanol was evaporated under reduced pressure and the residue was partitioned between EtOAc and water. The organic layer was washed with water, saturated $NaHCO_3$ solution and brine, dried over $MgSO_4$ and evaporated. The residue was purified by silica gel column chromatography (EtOAc/heptane (2/1) to EtOAc) to give a mixture of regioisomeric products as colourless oils. Yield (165 mg; 17%)

ESI-MS $[M+H^+]$=432 Calculated for $C_{23}H_{30}ClN_3O_3$=431

Intermediate 9 tert-Butyl 7-(1-(4-chlorophenyl)cyclobutyl)-2-(2-hydroxyethyl)-4,5-dihydro-2H-pyrazolo[3,4-c]pyridine-6(7H)-carboxylate

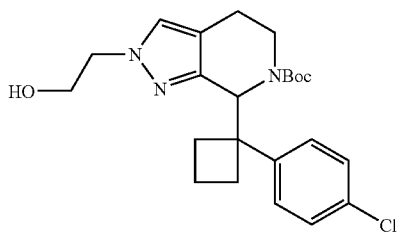

Chemical Formula: $C_{23}H_{30}ClN_3O_3$
Exact Mass: 431.2

The more polar product of the above reaction was identified as tert-butyl 7-(1-(4-chlorophenyl)cyclobutyl)-2-(2-hydroxyethyl)-4,5-dihydro-2H-pyrazolo[3,4-c]pyridine-6(7H)-carboxylate. Yield (401 mg; 43%)

ESI-MS $[M+H^+]$=432 Calculated for $C_{23}H_{30}ClN_3O_3$=431

Intermediate 10 tert-butyl 1-(2-aminoethyl)-7-(1-(4-chlorophenyl)cyclobutyl)-4,5-dihydro-1H-pyrazolo[3,4-c]pyridine-6(7H)-carboxylate

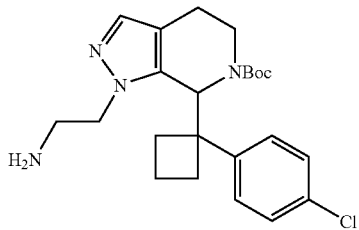

Chemical Formula: $C_{23}H_{31}ClN_4O_2$
Exact Mass: 430.21

10.1 Step A

The intermediate 8 (165 mg; 0.38 mmol) was dissolved in dichloromethane and treaded with triethylamine (0.08 ml; 1.5 eq) and mesylchloride (0.04 ml; 1.25) at 0° C. for 2 h. The mixture was diluted with dichloromethane and washed with dilute HCl, saturated $NaHCO_3$ solution, brine, dried over $MgSO_4$ and evaporated. The crude product was used without further purification for the next step.

10.2 Step B

A solution of the product of the step A and $NaN_3$ (0.04 g; 1.5 eq) in DMF (1 ml) was stirred for 90 min at 85° C. The mixture was diluted with EtOAc and washed with water, brine, dried over $MgSO_4$ and evaporated. The crude product was used without further purification for the next step.

10.3 Step C

A solution of the product of step B and $PPh_3$ (150 mg; 1.5 eq) in THF/water (1 ml; 20/1) was stirred at 65° C. for 2 h.

The mixture was cooled to room temperature and diluted with EtOAc. The organic layer was washed with water, brine, dried over MgSO$_4$ and evaporated. The residue was purified by silica gel column chromatography (DCM=>DCM/MeOH 10/1) give the product (0.98 g) as colourless oils.

ESI-MS [M+H$^+$]=431 Calculated for C$_{23}$H$_{31}$ClN$_4$O$_2$=430

Intermediate 11 tert-Butyl 2-(2-aminoethyl)-7-(1-(4-chlorophenyl) cyclobutyl)-4,5-dihydro-2H-pyrazolo[3,4-c]pyridine-6(7H)-carboxylate

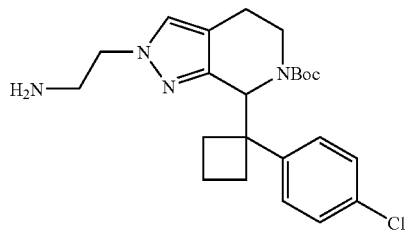

Chemical Formula: C$_{23}$H$_{31}$ClN$_4$O$_2$
Exact Mass: 430.21

The compound was prepared analogously to intermediate 10 from tert-butyl 7-(1-(4-chlorophenyl)cyclobutyl)-2-(2-hydroxyethyl)-4,5-dihydro-2H-pyrazolo[3,4-c]pyridine-6(7H)-carboxylate (intermediate 9).

ESI-MS [M+H$^+$]=431 Calculated for C$_{23}$H$_{31}$ClN$_4$O$_2$=430

Intermediate 12

Ethyl 8-(1-(4-chlorophenyl)cyclobutyl)-2-methyl-5,6,7,8-tetrahydro-1,7-naphthyridine-3-carboxylate dihydrochloride

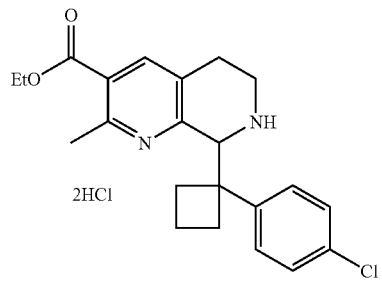

Chemical Formula: C$_{22}$H$_{25}$ClN$_2$O$_2$
Exact Mass: 384.16

12.1 Step A

A mixture of intermediate 6 (200 mg; 0.48 mmol), ethylacetoacetate (0.07 ml; 1.1 eq; 0.525 mmol) and ammonium acetate (300 mg; 8 eq) in acetic acid (5 ml) was stirred at 100° C. for 1 h. The mixture was cooled to room temperature and diluted with ethyl acetate. The mixture was washed with water (2×), saturated NaHCO$_3$ solution, brine and dried over anhydrous MgSO$_4$ and concentrated. The residue was purified by silica gel column chromatography to give the product (123 mg; 53%) as colorless oil.

12.2 Step B

The product of the step A (20.0 mg) was dissolved in 5N isopropanolic hydrochloric acid (1 ml) and stirred for 2 h at room temperature. The solvents were evaporated and the product (16.9 mg; 97%) was dried in vacuo.

ESI-MS [M+H$^+$]=385 Calculated for C$_{22}$H$_{25}$ClN$_2$O$_2$=384

Intermediate 13 tert-Butyl 2-(aminomethyl)-8-(1-(4-chlorophenyl) cyclobutyl)-5,6-dihydropyrido[3,4-d]pyrimidine-7(8H)-carboxylate

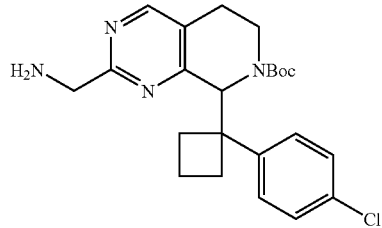

Chemical Formula: C$_{23}$H$_{29}$ClN$_4$O$_2$
Exact Mass: 428.2

A solution of intermediate 6 (0.5 g; 1.2 mmol), aminoacetamidine dibromide (0.35 g; 1.2 eq) and freshly prepared sodium ethoxide (0.14 g sodium; (5 eq) in 5 ml ethanol) in ethanol (5 ml) was stirred at 85° C. for 4 h. The solvent was removed under reduced pressure and the residue was diluted with EtOAc and water. The layers were separated and the organic layer was washed with water, brine, dried over MgSO$_4$ and evaporated. The residue was purified by silica gel column chromatography to give the product (0.153 g; 30%) as brown oil.

ESI-MS [M+H$^+$]=429 Calculated for C$_{18}$H$_{21}$ClN$_4$=428

Intermediate 14 tert-Butyl 4-bromo-2-(1-(4-chlorophenyl)cyclobutyl)-3-oxopiperidine-1-carboxylate

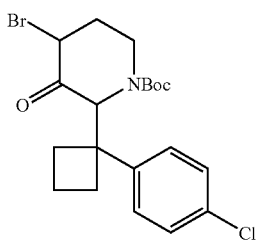

Chemical Formula: C$_{20}$H$_{25}$BrClNO$_3$
Exact Mass: 441.07

Intermediate 9 (2 g, 1.0 eq) was dissolved in THF and pyridinium bromide perbromide (2.15 g, 1.1 eq) was added. The resulting mixture was stirred for 2 h at room temperature until complete conversion. The reaction mixture was diluted with ethyl acetate and washed with saturated sodium thiosulfite, water and brine. The organic layer was dried over MgSO$_4$ and concentrated in vacuum. The residue was purified by silica gel column chromatography to give the product (1.6 g, 66%) as a yellow oil.

ESI-MS [M+H$^+$]=492 Calculated for C$_{24}$H$_{34}$ClN$_5$O$_2$S=491

Intermediate 15 tert-Butyl 4-(1-(4-chlorophenyl)cyclobutyl)-2-(cyanomethyl)-6,7-dihydrothiazolo[4,5-c]pyridine-5(4H)-carboxylate

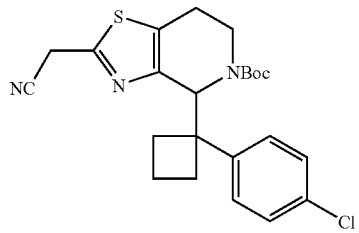

Chemical Formula: C$_{23}$H$_{26}$ClN$_3$O$_2$S
Exact Mass: 443.14

Intermediate 14 (500 mg, 1 eq) and 2-Cyanothioacetamide (136 mg, 1.2 eq) were dissolved in DMSO and heated to 65° C. for 5 h. The reaction mixture was dissolved with ethyl acetate and washed with water (3×) and brine. The organic layer was dried over MgSO$_4$ and concentrated in vacuum. The residue was purified by silica gel column chromatography to give the product (236 mg, 46%) as a yellow oil.

ESI-MS [M+H$^+$]=492 Calculated for C$_{24}$H$_{34}$ClN$_5$O$_2$S=491 Intermediate 16 tert-Butyl 2-(2-aminoethyl)-4-(1-(4-chlorophenyl)cyclobutyl)-6,7-dihydrothiazolo[4,5-c]pyridine-5(4H)-carboxylate

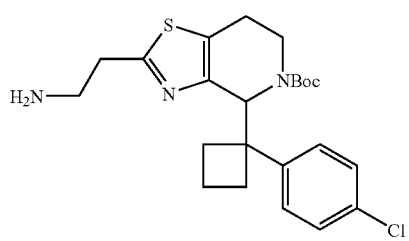

Chemical Formula: C$_{23}$H$_{30}$ClN$_3$O$_2$S
Exact Mass: 447.17

Raney-nickel (10 mg, 10 wt %) was added to a solution of intermediate 15 (100 mg) in ethanol. The reaction mixture was stirred under hydrogen atmosphere over night at room temperature. The reaction mixture was filtered over a plug of celite, concentrated and used for the next step without further purification.

ESI-MS [M+H$^+$]=448 Calculated for C$_{23}$H$_{30}$ClN$_3$O$_2$S=447

Example 1

7-(1-Phenylcyclobutyl)-2-(2-(propylsulfonamido)ethyl)-4,5,6,7-tetrahydro-2H-pyrazolo[3,4-c]pyridin-6-ium chloride

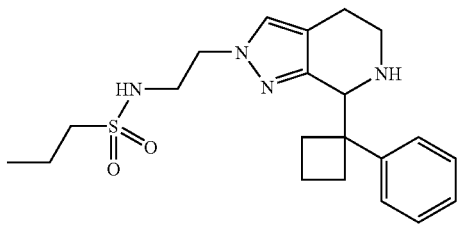

Chemical Formula: C$_{21}$H$_{30}$N$_4$O$_2$S
Exact Mass: 402.21

ESI-MS [M+H$^+$]=403 Calculated for C$_{21}$H$_{30}$ClN$_4$O$_2$S=402

Step A

The intermediate 11 was dissolved in dichloromethane. DMAP (1.5 eq) and n-propyl sulfonylchlorid were added. The reaction was stirred for 3 hours at room temperature. After complete conversation the reaction was diluted with dichloromethane and washed with HCl (0.1 N), water and brine, dried over MgSO$_4$ and evaporated. The residue was purified by PTLC to give the desired n-propyl sulfonylamid.

Step B

The product of the step above was dissolved in MeOH and Pd/C (10 wt %) and ammonia formate (25 eq) were added. The resulting reaction mixture was stirred over night at room temperature. The reaction mixture was filtered, diluted with EtOAc and washed with water (3×). The organic layer was dried over MgSO$_4$, evaporated and used directly for the next step.

Step C

The product of the step above was treated with HCl in isopropanol (5 N). After stirring for 2 hours at room temperature the reaction was complete. The solvents were evaporated and the product was dried in vacuo.

Example 2

N-(Azetidin-3-yl)-N-(2-(7-(1-(4-chlorophenyl)cyclobutyl)-4,5,6,7-tetrahydro-2H-pyrazolo[3,4-c]pyridin-2-yl)ethyl)propane-1-sulfonamide dihydrochloride

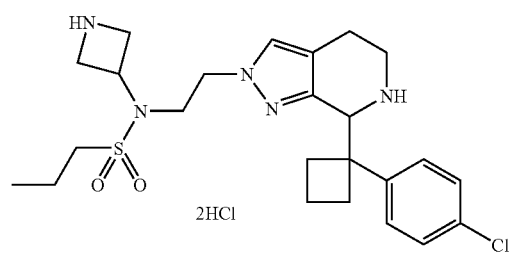

Chemical Formula: C$_{24}$H$_{34}$ClN$_5$O$_2$S
Exact Mass: 491.21

N-(Azetidin-3-yl)-N-(2-(7-(1-(4-chlorophenyl)cyclobutyl)-4,5,6,7-tetrahydro-2H-pyrazolo[3,4-c]pyridin-2-yl)ethyl)propane-1-sulfonamide dihydrochloride was prepared according to the procedure of example 10 using 1-Boc-3-iodo-azetidine.

ESI-MS [M+H$^+$]=492 Calculated for $C_{24}H_{34}ClN_5O_2S$=491

Example 3

8-(1-(4-Chlorophenyl)cyclobutyl)-5,6,7,8-tetrahydropyrido[3,4-d]pyrimidine-2-carbonitrile hydrochloride

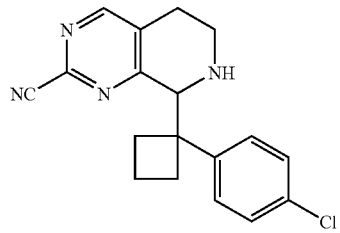

Chemical Formula: $C_{18}H_{17}ClN_4$
Exact Mass: 324.11

Step A

A solution of intermediate 6 (100 mg; 0.24 mmol), 2-methyl 2-thiopseudourea sulfate (86 mg; 1.3 eq; 0.312 mmol) and sodium ethoxide (freshly prepared; 1.5 eq) in ethanol (1 ml) was stirred at 90° C. for 4 h. The solvent was removed under reduced pressure and the residue was diluted with EtOAc and water. The layers were separated and the organic layer was washed with water, brine, dried over MgSO$_4$ and evaporated. The residue was purified by silica gel column chromatography to give the product (63 mg; 59%) as colorless oil.

Step B

To a stirred and cooled (0° C.) solution of the product (50 mg; 0.112 mmol) of the step A in dichloromethane (1 ml) was added m-CPBA (77 mg; 4 eq) and the mixture was stirred at the same temperature for 2 h. The mixture was diluted with dichloromethane and washed with 10% aqueous Na$_2$SO$_3$, saturated NaHCO$_3$ solution, brine, dried over MgSO$_4$ and evaporated. The residue was purified by PTLC using EtOAc/heptane (3/2) to give the product (25 mg; 47%) as colorless oil.

Step C

A mixture of the product (50 mg; 0.105 mmol) of the step B and NaCN (8 mg; 1.5 eq) in DMF (1 ml) was stirred at 110° C. for 90 min. The mixture was diluted with EtOAc and washed with water, brine dried over MgSO$_4$ and evaporated. The residue was purified by PTLC to give the product (18 mg; 40%) as colorless oil.

Step D

The product of the step C was diluted in dichloromethane and anhydrous 3 N HCl in dioxane was added. The mixture was stirred for 30 min at room temperature. The mixture was diluted with EtOAc and washed with saturated NaHCO$_3$ solution, brine dried and evaporated. The residue was purified by PTLC to give the product as colorless oil.

ESI-MS [M+H$^+$]=325 Calculated for $C_{22}H_{25}ClN_2O_2$=324

Example 4

(8-(1-(4-Chlorophenyl)cyclobutyl)-5,6,7,8-tetrahydropyrido[3,4-d]pyrimidin-2-yl)methanamine dihydrochloride

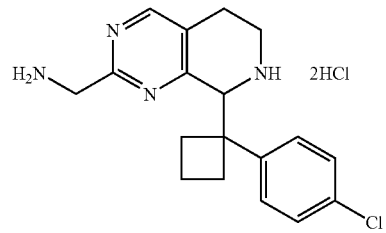

Chemical Formula: $C_{18}H_{21}ClN_4$
Exact Mass: 328.15

Intermediate 13 was dissolved in 5 N isopropanolic hydrochloric acid (1 ml) and stirred for 2 h at room temperature. The solvents were evaporated and the product was dried in vacuo.

ESI-MS [M+H$^+$]=329 Calculated for $C_{18}H_{21}ClN_4$=328

Example 5

2-(7-(1-(4-Chlorophenyl)cyclobutyl)-4,5,6,7-tetrahydro-1H-pyrazolo[3,4-c]pyridin-1-yl)ethanamine dihydrochloride

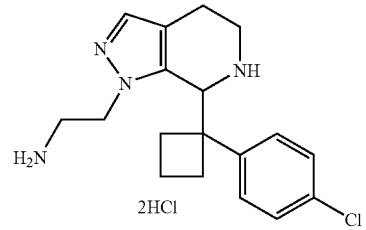

Chemical Formula: $C_{18}H_{23}ClN_4$
Exact Mass: 330.16

The intermediate 10 was dissolved in 5 N isopropanolic hydrochloric acid (1 ml) and stirred for 2 h at room temperature. The solvents were evaporated and the product was dried in vacuo.

ESI-MS [M+H$^+$]=431 Calculated for $C_{18}H_{23}ClN_4$=430

Example 6

2-(7-(1-(4-Chlorophenyl)cyclobutyl)-4,5,6,7-tetrahydro-2H-pyrazolo[3,4-c]pyridin-2-yl)ethanamine dihydrochloride

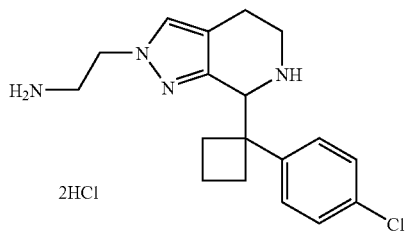

Chemical Formula: $C_{18}H_{23}ClN_4$
Exact Mass: 330.16

The intermediate 11 was dissolved in 5 N isopropanolic hydrochloric acid (1 ml) and stirred for 2 h at room temperature. The solvents were evaporated and the product was dried in vacuo.

ESI-MS [M+H$^+$]=331 Calculated for C$_{18}$H$_{23}$ClN$_4$=330

Example 7

General Procedure

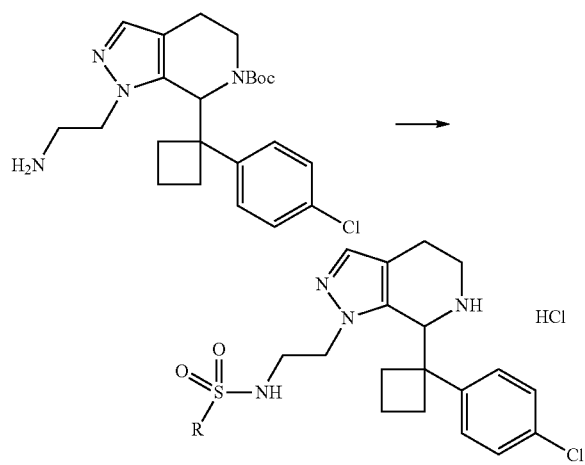

Step A

The intermediate 10 was dissolved in dichloromethane. DMAP (1.5 eq) and the appropriate sulfonylchlorid were added. The reaction was stirred for 3 hours at room temperature. After complete conversation the reaction was diluted with dichloromethane and washed with HCl (0.1 N), water and brine, dried over MgSO$_4$ and evaporated. The residue was purified by PTLC to give the desired sulfonylamid.

Step B

The product of the step A was treated with HCl in isopropanol (5 N). After stirring for 2 hours at room temperature the reaction was complete. The solvents were evaporated and the product was dried in vacuo.

Example 7.1

N-(2-(7-(1-(4-Chlorophenyl)cyclobutyl)-4,5,6,7-tetrahydro-1H-pyrazolo[3,4-c]pyridin-1-yl)ethyl)propane-1-sulfonamide hydrochloride

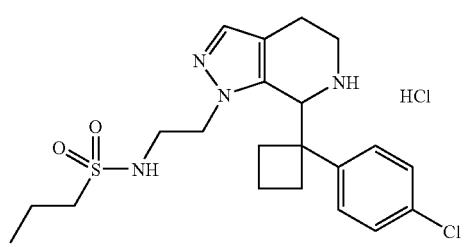

Chemical Formula: C$_{21}$H$_{29}$ClN$_4$O$_2$S
Exact Mass: 436.17

N-(2-(7-(1-(4-Chlorophenyl)cyclobutyl)-4,5,6,7-tetrahydro-1H-pyrazolo[3,4-c]pyridin-1-yl)ethyl)propane-1-sulfonamide hydrochloride was prepared according to the general procedure of example 7 using propane-1-sulfonyl chloride.

ESI-MS [M+H$^+$]=437 Calculated for C$_{21}$H$_{29}$ClN$_4$O$_2$S=436

Example 7.2

N-(2-(7-(1-(4-Chlorophenyl)cyclobutyl)-4,5,6,7-tetrahydro-1H-pyrazolo[3,4-c]pyridin-1-yl)ethyl)-1-methyl-1H-pyrazole-4-sulfonamide hydrochloride

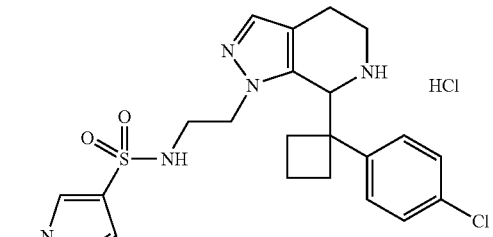

Chemical Formula: C$_{22}$H$_{27}$ClN$_6$O$_2$S
Exact Mass: 474.16

N-(2-(7-(1-(4-Chlorophenyl)cyclobutyl)-4,5,6,7-tetrahydro-1H-pyrazolo[3,4-c]pyridin-1-ylethyl)-1-methyl-1H-pyrazole-4-sulfonamide hydrochloride was prepared according to the general procedure of example 7 using 1-methyl-1H-pyrazole-4-sulfonyl chloride.

ESI-MS [M+H$^+$]=475 Calculated for C$_{22}$H$_{27}$ClN$_6$O$_2$S=474

Example 7.3

N-(2-(7-(1-(4-Chlorophenyl)cyclobutyl)-4,5,6,7-tetrahydro-1H-pyrazolo[3,4-c]pyridin-1-yl)ethyl)-3-fluoropropane-1-sulfonamide hydrochloride

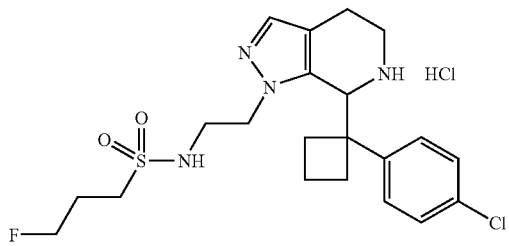

Chemical Formula: C$_{21}$H$_{28}$ClFN$_4$O$_2$S
Exact Mass: 454.16

N-(2-(7-(1-(4-Chlorophenyl)cyclobutyl)-4,5,6,7-tetrahydro-1H-pyrazolo[3,4-c]pyridin-1-yl)ethyl)-3-fluoropropane-1-sulfonamide hydrochloride was prepared according to the general procedure of example 7 using 3-fluoropropane-1-sulfonyl chloride.

ESI-MS [M+H$^+$]=455 Calculated for C$_{21}$H$_{28}$ClFN$_4$O$_2$S=455

Example 7.4

N-(2-(7-(1-(4-Chlorophenyl)cyclobutyl)-4,5,6,7-tetrahydro-1H-pyrazolo[3,4-c]pyridin-1-yl)ethyl)-1-methyl-1H-imidazole-4-sulfonamide hydrochloride

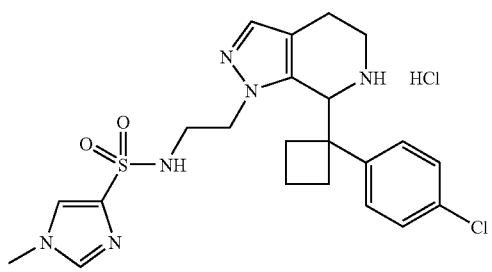

Chemical Formula: C$_{22}$H$_{27}$ClN$_6$O$_2$S
Exact Mass: 474.16

N-(2-(7-(1-(4-Chlorophenyl)cyclobutyl)-4,5,6,7-tetrahydro-1H-pyrazolo[3,4-c]pyridin-1-yl)ethyl)-1-methyl-1H-imidazole-4-sulfonamide hydrochloride was prepared according to the general procedure of example 7 using 1-methyl-1H-imidazole-4-sulfonyl chloride.

ESI-MS [M+H$^+$]=475 Calculated for C$_{22}$H$_{27}$ClN$_6$O$_2$S=474

Example 8

General Procedure

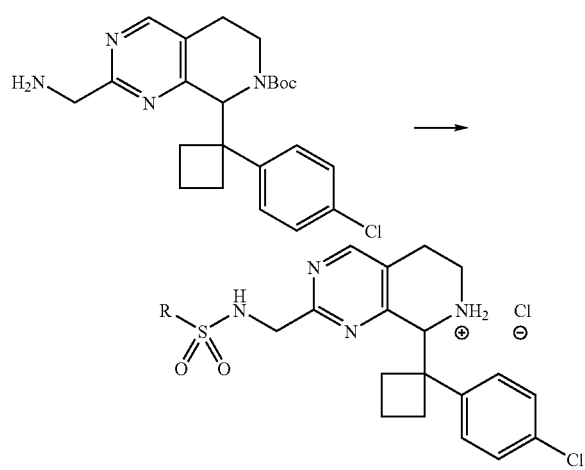

Step A

Intermediate 13 was dissolved in dichloromethane. DMAP (1.5 eq) and sulfonylchlorid were added. The reaction was stirred for 3 hours at room temperature. After complete conversation the reaction was diluted with dichloromethane and washed with HCl (0.1 N), water and brine, dried over MgSO$_4$ and evaporated. The residue was purified by PTLC to give the desired sulfonylamid.

Step B

The product of the step A was treated with HCl in isopropanol (5 N). After stirring for 2 hours at room temperature the reaction was complete. The solvents were evaporated and the product was dried in vacuo.

Example 8.1

N-((8-(1-(4-Chlorophenyl)cyclobutyl)-5,6,7,8-tetrahydropyrido[3,4-d]pyrimidin-2-yl)methyl)propane-1-sulfonamide hydrochloride

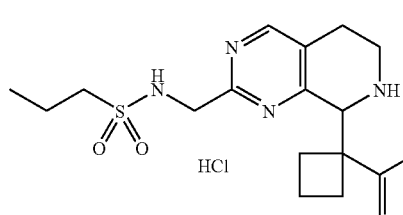

Chemical Formula: C$_{21}$H$_{27}$ClN$_4$O$_2$S
Exact Mass: 434.15

N-((8-(1-(4-Chlorophenyl)cyclobutyl)-5,6,7,8-tetrahydropyrido[3,4-d]pyrimidin-2-yl)methyl)propane-1-sulfonamide hydrochloride was prepared according to the general procedure of example 8 using propane-1-sulfonyl chloride.

ESI-MS [M+H$^+$]=435 Calculated for C$_{21}$H$_{27}$ClN$_4$O$_2$S=434

Example 8.2

N-((8-(1-(4-Chlorophenyl)cyclobutyl)-5,6,7,8-tetrahydropyrido[3,4-d]pyrimidin-2-yl)methyl)-1-cyclopropylmethanesulfonamide hydrochloride

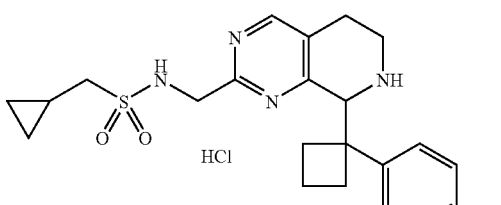

Chemical Formula: C$_{22}$H$_{27}$ClN$_4$O$_2$S
Exact Mass: 446.15

N-((8-(1-(4-Chlorophenyl)cyclobutyl)-5,6,7,8-tetrahydropyrido[3,4-d]pyrimidin-2-yl)methyl)-1-cyclopropylmethanesulfonamide hydrochloride was prepared according to the general procedure of example 8 using 1-cyclopropylmethanesulfonyl chloride.

ESI-MS [M+H⁺]=447 Calculated for C$_{22}$H$_{25}$ClN$_4$O$_2$S=446

Example 8.3

N-((8-(1-(4-Chlorophenyl)cyclobutyl)-5,6,7,8-tetrahydropyrido[3,4-d]pyrimidin-2-yl)methyl)-1-methyl-1H-pyrazole-4-sulfonamide hydrochloride

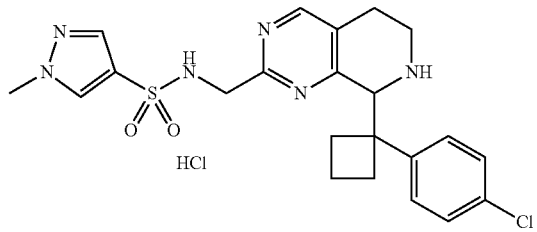

Chemical Formula: C$_{22}$H$_{25}$ClN$_6$O$_2$S
Exact Mass: 472.14

N-((8-(1-(4-Chlorophenyl)cyclobutyl)-5,6,7,8-tetrahydropyrido[3,4-d]pyrimidin-2-yl)methyl)-1-methyl-1H-pyrazole-4-sulfonamide hydrochloride was prepared according to the general procedure of example 8 using 1-methyl-1H-pyrazole-4-sulfonyl chloride.

ESI-MS [M+H⁺]=473 Calculated for C$_{22}$H$_{25}$ClN$_6$O$_2$S=472

Example 8.4

N-((8-(1-(4-Chlorophenyl)cyclobutyl)-5,6,7,8-tetrahydropyrido[3,4-d]pyrimidin-2-yl)methyl)-1-methyl-1H-imidazole-4-sulfonamide hydrochloride

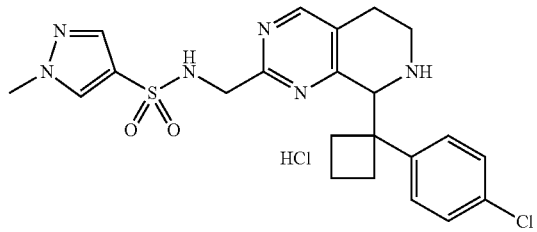

Chemical Formula: C$_{22}$H$_{25}$ClN$_6$O$_2$S
Exact Mass: 472.14

N-((8-(1-(4-Chlorophenyl)cyclobutyl)-5,6,7,8-tetrahydropyrido[3,4-d]pyrimidin-2-yl)methyl)-1-methyl-1H-imidazole-4-sulfonamide hydrochloride was prepared according to the general procedure of example 8 using 1-methyl-1H-imidazole-4-sulfonyl chloride.

ESI-MS [M+H⁺]=473 Calculated for C$_{22}$H$_{25}$ClN$_6$O$_2$S=472

Example 8.5

N-((8-(1-(4-Chlorophenyl)cyclobutyl)-5,6,7,8-tetrahydropyrido[3,4-d]pyrimidin-2-yl)methyl)-3-fluoropropane-1-sulfonamide hydrochloride

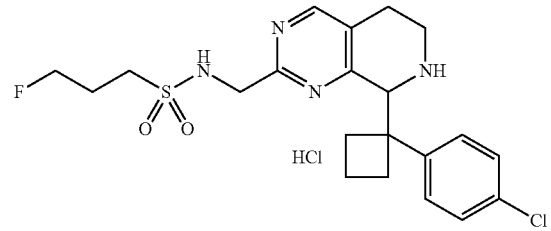

Chemical Formula: C$_{21}$H$_{26}$ClN$_4$O$_2$S
Exact Mass: 452.14

N-((8-(1-(4-Chlorophenyl)cyclobutyl)-5,6,7,8-tetrahydropyrido[3,4-d]pyrimidin-2-yl)methyl)-3-fluoropropane-1-sulfonamide hydrochloride was prepared according to the general procedure of example 8 using 3-fluoropropane-1-sulfonyl chloride.

ESI-MS [M+H⁺]=453 Calculated for C$_{21}$H$_{26}$ClN$_4$O$_2$S=452

Example 9

General Procedure

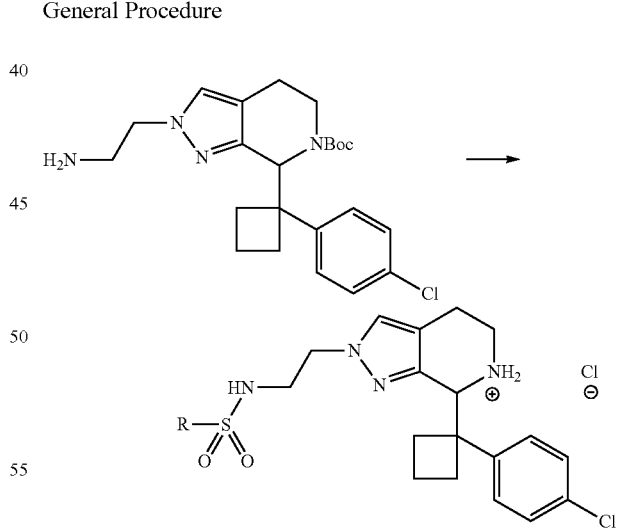

Step A

The intermediate 11 was dissolved in dichloromethane. DMAP (1.5 eq) and sulfonylchlorid were added. The reaction was stirred for 3 hours at room temperature. After complete conversation the reaction was diluted with dichloromethane and washed with HCl (0.1 N), water and brine, dried over MgSO$_4$ and evaporated. The residue was purified by PTLC to give the desired sulfonylamid.

Step B

The product of the step A was treated with HCl in isopropanol (5 N). After stirring for 2 hours at room temperature the reaction was complete. The solvents were evaporated and the product was dried in vacuo.

Example 9.1

N-(2-(7-(1-(4-Chlorophenyl)cyclobutyl)-4,5,6,7-tetrahydro-2H-pyrazolo[3,4-c]pyridin-2-yl)ethyl)propane-1-sulfonamide hydrochloride

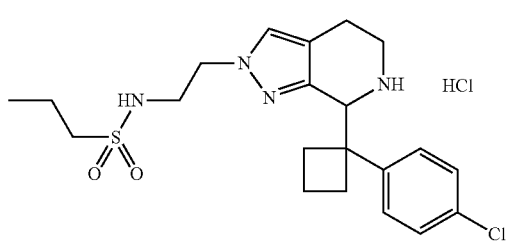

Chemical Formula: $C_{21}H_{29}ClN_4O_2S$
Exact Mass: 436.17

N-(2-(7-(1-(4-Chlorophenyl)cyclobutyl)-4,5,6,7-tetrahydro-2H-pyrazolo[3,4-c]pyridin-2-yl)ethyl)propane-1-sulfonamide hydrochloride was prepared according to the general procedure of example 9 using propane-1-sulfonyl chloride.

ESI-MS [M+H$^+$]=437 Calculated for $C_{21}H_{29}ClN_4O_2S$=436

Example 9.2

N-(2-(7-(1-(4-Chlorophenyl)cyclobutyl)-4,5,6,7-tetrahydro-2H-pyrazolo[3,4-c]pyridin-2-yl)ethyl)ethanesulfonamide hydrochloride

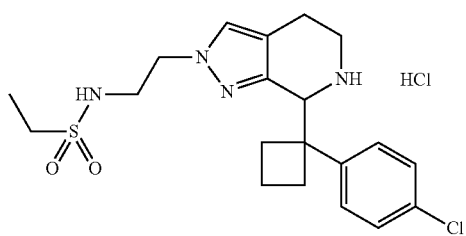

Chemical Formula: $C_{20}H_{27}ClN_4O_2S$
Exact Mass: 422.15

N-(2-(7-(1-(4-Chlorophenyl)cyclobutyl)-4,5,6,7-tetrahydro-2H-pyrazolo[3,4-c]pyridin-2-yl)ethyl)ethanesulfonamide hydrochloride was prepared according to the general procedure of example 9 using ethanesulfonyl chloride.

ESI-MS [M+H$^+$]=423 Calculated for $C_{20}H_{27}ClN_4O_2S$=422

Example 9.3

N-(2-(7-(1-(4-Chlorophenyl)cyclobutyl)-4,5,6,7-tetrahydro-2H-pyrazolo[3,4-c]pyridin-2-yl)ethyl)methanesulfonamide hydrochloride

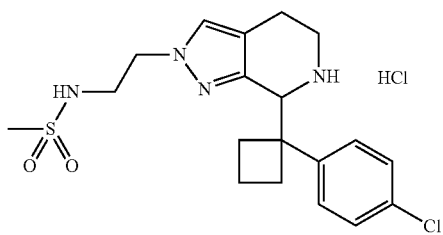

Chemical Formula: $C_{19}H_{25}ClN_4O_2S$
Exact Mass: 408.14

N-(2-(7-(1-(4-Chlorophenyl)cyclobutyl)-4,5,6,7-tetrahydro-2H-pyrazolo[3,4-c]pyridin-2-yl)ethyl)methanesulfonamide hydrochloride was prepared according to the general procedure of example 9 using methanesulfonyl chloride.

ESI-MS [M+H$^+$]=409 Calculated for $C_{19}H_{25}ClN_4O_2S$=408

Example 9.4

N-(2-(7-(1-(4-Chlorophenyl)cyclobutyl)-4,5,6,7-tetrahydro-2H-pyrazolo[3,4-c]pyridin-2-yl)ethyl)benzenesulfonamide hydrochloride

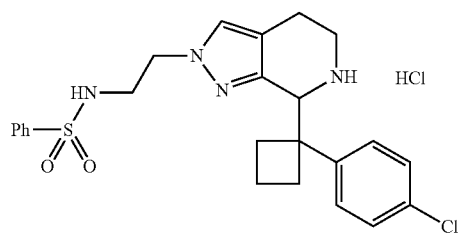

Chemical Formula: $C_{24}H_{27}ClN_4O_2S$
Exact Mass: 470.15

N-(2-(7-(1-(4-Chlorophenyl)cyclobutyl)-4,5,6,7-tetrahydro-2H-pyrazolo[3,4-c]pyridin-2-yl)ethyl)benzenesulfonamide hydrochloride was prepared according to the general procedure of example 9 using benzenesulfonyl chloride.

ESI-MS [M+H$^+$]=471 Calculated for $C_{24}H_{27}ClN_4O_2S$=470

Example 9.5

N-(2-(7-(1-(4-Chlorophenyl)cyclobutyl)-4,5,6,7-tetrahydro-2H-pyrazolo[3,4-c]pyridin-2-yl)-ethyl)butane-1-sulfonamide hydrochloride

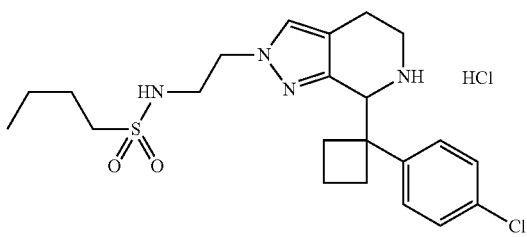

Chemical Formula: $C_{22}H_{31}ClN_4O_2S$
Exact Mass: 450.19

N-(2-(7-(1-(4-Chlorophenyl)cyclobutyl)-4,5,6,7-tetrahydro-2H-pyrazolo[3,4-c]pyridin-2-yl)ethyl)butane-1-sulfonamide hydrochloride was prepared according to the general procedure of example 9 using butane-1-sulfonyl chloride.

ESI-MS [M+H$^+$]=451 Calculated for $C_{22}H_{31}ClN_4O_2S$=450

Example 9.6

N-(2-(7-(1-(4-Chlorophenyl)cyclobutyl)-4,5,6,7-tetrahydro-2H-pyrazolo[3,4-c]pyridin-2-yl)-ethyl)-1-methyl-1H-pyrazole-4-sulfonamide hydrochloride

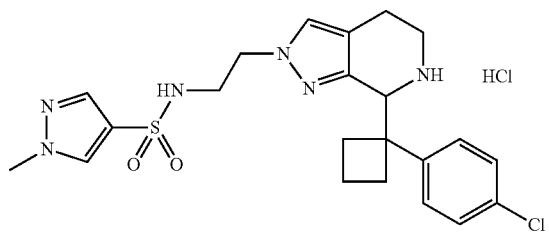

Chemical Formula: $C_{22}H_{27}ClN_6O_2S$
Exact Mass: 474.16

N-(2-(7-(1-(4-Chlorophenyl)cyclobutyl)-4,5,6,7-tetrahydro-2H-pyrazolo[3,4-c]pyridin-2-yl)ethyl)-1-methyl-1H-pyrazole-4-sulfonamide hydrochloride was prepared according to the general procedure of example 9 using 1-methyl-1H-pyrazole-4-sulfonyl chloride.

ESI-MS [M+H$^+$]=475 Calculated for $C_{22}H_{27}ClN_6O_2S$=474

Example 9.7

N-(2-(7-(1-(4-Chlorophenyl)cyclobutyl)-4,5,6,7-tetrahydro-2H-pyrazolo[3,4-c]pyridin-2-yl)ethyl)-1-methyl-1H-imidazole-4-sulfonamide hydrochloride

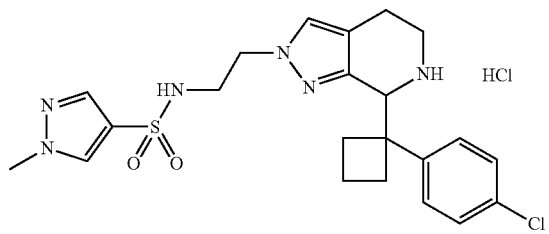

Chemical Formula: $C_{22}H_{27}ClN_6O_2S$
Exact Mass: 474.16

N-(2-(7-(1-(4-Chlorophenyl)cyclobutyl)-4,5,6,7-tetrahydro-2H-pyrazolo[3,4-c]pyridin-2-yl)ethyl)-1-methyl-1H-imidazole-4-sulfonamide hydrochloride was prepared according to the general procedure of example 9 using 1-methyl-1H-imidazole-4-sulfonyl chloride.

ESI-MS [M+H$^+$]=475 Calculated for $C_{22}H_{27}ClN_6O_2S$=474

Example 9.8

N-(2-(7-(1-(4-Chlorophenyl)cyclobutyl)-4,5,6,7-tetrahydro-2H-pyrazolo[3,4-c]pyridin-2-yl)ethyl)-3-fluoropropane-1-sulfonamide hydrochloride

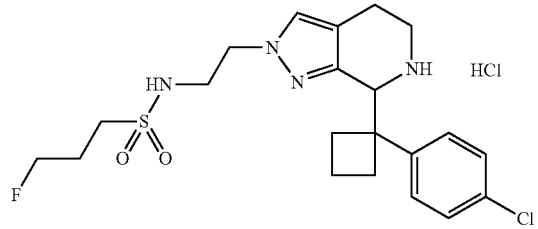

Chemical Formula: $C_{21}H_{28}ClN_4O_2S$
Exact Mass: 454.16

N-(2-(7-(1-(4-Chlorophenyl)cyclobutyl)-4,5,6,7-tetrahydro-2H-pyrazolo[3,4-c]pyridin-2-yl)ethyl)-3-fluoropropane-1-sulfonamide hydrochloride was prepared according to the general procedure of example 9 using 3-fluoropropane-1-sulfonyl chloride.

ESI-MS [M+H$^+$]=455 Calculated for $C_{21}H_{28}ClN_4O_2S$=454

Example 9.9

N-(2-(7-(1-(4-Chlorophenyl)cyclobutyl)-4,5,6,7-tetrahydro-2H-pyrazolo[3,4-c]pyridin-2-yl)-ethyl)cyclobutanesulfonamide hydrochloride

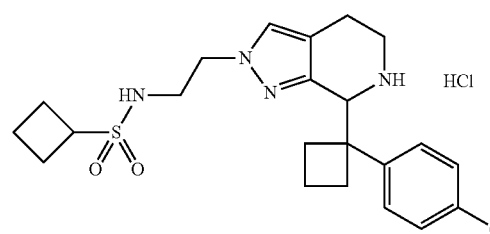

Chemical Formula: $C_{22}H_{29}ClN_4O_2S$
Exact Mass: 448.17

N-(2-(7-(1-(4-Chlorophenyl)cyclobutyl)-4,5,6,7-tetrahydro-2H-pyrazolo[3,4-c]pyridin-2-yl)-ethyl)cyclobutanesulfonamide hydrochloride was prepared according to the general procedure of example 9 using cyclobutanesulfonyl chloride.

ESI-MS [M+H$^+$]=449 Calculated for C$_{22}$H$_{29}$ClN$_4$O$_2$S=448

Example 9.10

N-(2-(7-(1-(4-Chlorophenyl)cyclobutyl)-4,5,6,7-tetrahydro-2H-pyrazolo[3,4-c]pyridin-2-yl)-ethyl)-1-cyclopropylmethanesulfonamide hydrochloride

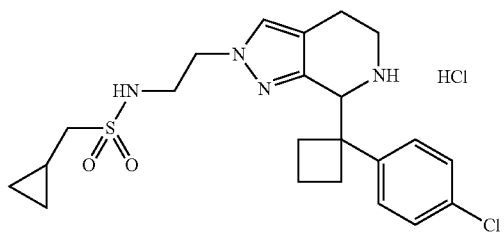

Chemical Formula: C$_{22}$H$_{29}$ClN$_4$O$_2$S
Exact Mass: 448.17

N-(2-(7-(1-(4-Chlorophenyl)cyclobutyl)-4,5,6,7-tetrahydro-2H-pyrazolo[3,4-c]pyridin-2-yl)ethyl)-1-cyclopropylmethanesulfonamide hydrochloride was prepared according to the general procedure of example 9 using 1-cyclopropylmethanesulfonyl chloride.

ESI-MS [M+H$^+$]=449 Calculated for C$_{22}$H$_{23}$ClN$_4$O$_2$S=448

Example 9.11

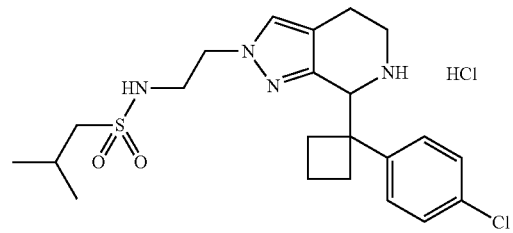

Chemical Formula: C$_{22}$H$_{31}$ClN$_4$O$_2$S
Exact Mass: 450.19

N-(2-(7-(1-(4-chlorophenyl)cyclobutyl)-4,5,6,7-tetrahydro-2H-pyrazolo[3,4-c]pyridin-2-yl)ethyl)-2-methylpropane-1-sulfonamide hydrochloride was prepared according to the general procedure of example 9 using 2-methylpropane-1-sulfonyl chloride.

ESI-MS [M+H$^+$]=451 Calculated for C$_{22}$H$_{31}$ClN$_4$O$_2$S=450

Example 9.12

N-(2-(7-(1-(4-Chlorophenyl)cyclobutyl)-4,5,6,7-tetrahydro-2H-pyrazolo[3,4-c]pyridin-2-yl)ethyl)pyridine-3-sulfonamide dihydrochloride

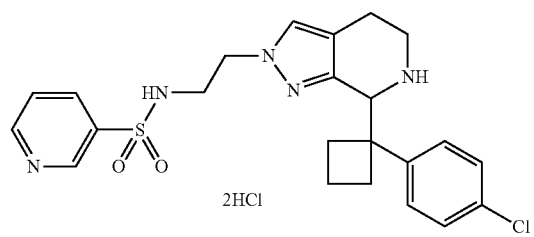

Chemical Formula: C$_{23}$H$_{26}$ClN$_5$O$_2$S
Exact Mass: 471.15

N-(2-(7-(1-(4-Chlorophenyl)cyclobutyl)-4,5,6,7-tetrahydro-2H-pyrazolo[3,4-c]pyridin-2-yl)ethyl)pyridine-3-sulfonamide dihydrochloride was prepared according to the general procedure of example 9 using pyridine-3-sulfonyl chloride.

ESI-MS [M+H$^+$]=472 Calculated for C$_{23}$H$_{26}$ClN$_5$O$_2$S=471

Example 10

N-(2-(7-(1-(4-chlorophenyl)cyclobutyl)-4,5,6,7-tetrahydro-2H-pyrazolo[3,4-c]pyridin-2-yl)ethyl)-N-methylpropane-1-sulfonamide hydrochloride

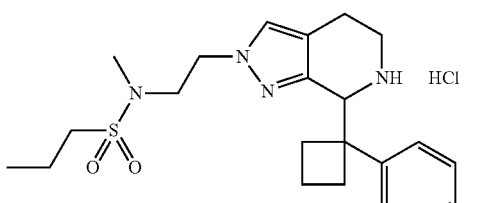

Chemical Formula: C$_{22}$H$_{31}$ClN$_4$O$_2$S
Exact Mass: 450.19

Step A

A mixture of the product of example 9.1, step A, methyl iodide and CsCO$_3$ in acetonitrile was heated for 2 hours at 100° C. in the micro wave. The mixture was diluted with EtOAc and washed with water and brine, dried over MgSO$_4$ and evaporated. The residue was purified by PTLC to yield the desired product.

Step B

The product of the step A was treated with HCl in isopropanol (5 N). After stirring for 2 hours at room temperature the reaction was complete. The solvents were evaporated and the product was dried in vacuo.

ESI-MS [M+H$^+$]=451 Calculated for C$_{22}$H$_{31}$ClN$_4$O$_2$S=450

Example 11

N-(2-{1-[1-(4-Chlorophenyl)cyclobutyl]-1,2,3,4-tetrahydro-9H-b-carbolin-9-yl}ethyl)propane-1-sulfonamide

11.1 1-[1-(4-Chlorophenyl)cyclobutyl]-2,3,4,9-tetrahydro-1H-b-carboline

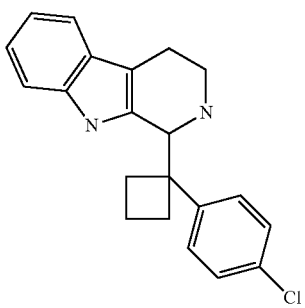 [SMILES: Clc1ccc(C2(C3NCCc4c3[nH]c3ccccc43)CCC2)cc1]

1-(4-Chlorophenyl)cyclobutanecarbaldehyde (30 mg, 0.154 mmol) and 2-(1H-indol-3-yl)ethanamine (27.7 mg, 0.17 mmol) were dissolved in dichloromethane (3 mL). Trifluoroacetic acid (88 mg, 0.771 mmol) were added at 0° C. and the reaction mixture was stirred at room temperature over night. The 5% NaHCO$_3$ solution was added. The aqueous layer was extracted with dichloromethane. The combined organic layers were washed successively with 5% NaHCO$_3$ solution and saturated sodium chloride solution, dried (MgSO$_4$) and concentrated in vacuo. Yield: 36 mg (oil, 0.107 mmol, 69%).

ESI-MS [M+H$^+$]=337 Calculated for C$_{21}$H$_{21}$ClN$_2$=336.

11.2 tert-Butyl 1-[1-(4-chlorophenyl)cyclobutyl]-1,3,4,9-tetrahydro-2H-b-carboline-2-carboxylate

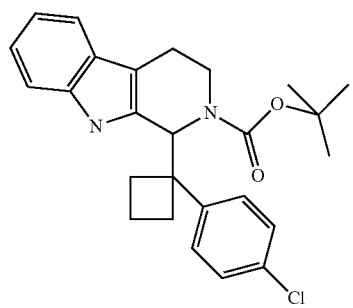 [SMILES: CC(C)(C)OC(=O)N1CCc2c([nH]c3ccccc23)C1C1(c2ccc(Cl)cc2)CCC1]

1-[1-(4-Chlorophenyl)cyclobutyl]-2,3,4,9-tetrahydro-1H-b-carboline (2.5 g, 7.42 mmol) were dissolved in tetrahydrofuran (30 mL). Triethylamine (2.253 g, 22.26 mmol) was added followed by di-tert-butyl dicarbonate (1.944 g, 8.91 mmol). The reaction mixture was stirred at room temperature over night. The solvent was evaporated in vacuo. Di-chloromethane (50 mL) was added and the organic layer washed successively with saturated ammonium chloride solution (2×40 mL) and water (40 mL). The organic phase was dried (MgSO$_4$) and concentrated in vacuo. The crude product was used for the next step without further purification. Yield: 3.1 g (beige solid, 96%).

ESI-MS [M+H$^+$]=437 Calculated for C$_{26}$H$_{29}$ClN$_2$O$_2$=436.

11.3 tert-Butyl 1-[1-(4-chlorophenyl)cyclobutyl]-9-(cyanomethyl)-1,3,4,9-tetrahydro-2H-b-carboline-2-carboxylate

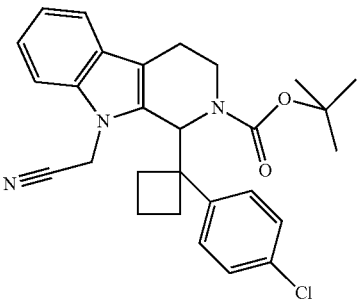 [SMILES: CC(C)(C)OC(=O)N1CCc2c(n(CC#N)c3ccccc23)C1C1(c2ccc(Cl)cc2)CCC1]

60% Sodium hydride suspension in mineral oil (0.412 g, 10.3 mmol) in dry dimethylformamide (25 mL) was stirred at room temperature under an atmosphere of nitrogen. tert-Butyl 1-[1-(4-chlorophenyl)cyclobutyl]-1,3,4,9-tetrahydro-2H-b-carboline-2-carboxylate (3.0 g, 6.87 mmol) was added in small portions. After 30 min stirring at room temperature 2-bromoacetonitrile (1.235 g, 10.3 mmol) in dimethylformamide (5 mL) was added dropwise. The reaction mixture was stirred at room temperature for two days. Water was added (1 mL). The reaction mixture was concentrated in vacuo, dichloromethane (100 mL) was added and the organic solution successively washed with water (50 mL), saturated NaHCO$_3$ solution (30 mL) and water (30 mL). The organic layer was dried (MgSO$_4$) and concentrated in vacuo. The crude product was purified by flash chromatography (silica, dichloromethane). Yield: 2.7 g (83%).

ESI-MS [M+-isobutene+H$^+$]=420 Calculated for C$_{28}$H$_{30}$ClN$_3$O$_2$=475.

11.4 tert-Butyl 9-(2-aminoethyl)-1-[1-(4-chlorophenyl)cyclobutyl]-1,3,4,9-tetrahydro-2H-b-carboline-2-carboxylate

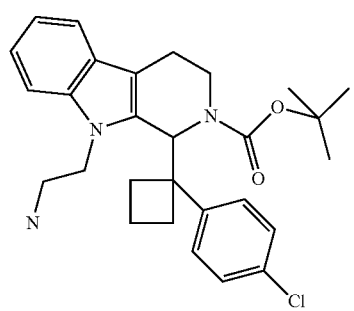 [SMILES: CC(C)(C)OC(=O)N1CCc2c(n(CCN)c3ccccc23)C1C1(c2ccc(Cl)cc2)CCC1]

Lithium aluminium hydride (0.281 g, 7.41 mmol) was suspended in diethyl ether (40 mL). The slurry was cooled to −5° C. and tert-butyl 1-[1-(4-chlorophenyl)cyclobutyl]-9-(cyanomethyl)-1,3,4,9-tetrahydro-2H-b-carboline-2-carboxylate (2.35 g, 4.94 mmol) was added in small portions.

After stirring at −5° C. for 1 h 2N sodium hydroxide solution (15 mL) was added dropwise. After 10 min additional 2N sodium hydroxide solution (60 mL) was added. The aqueous layer was extracted with ethyl acetate (3×40 mL). The combined organic layers were washed with water (30 mL), dried (MgSO$_4$) and concentrated in vacuo. The crude product was purified by flash chromatography (silica, dichloromethane, methanol). Yield: 0.16 g (7%).

ESI-MS [M+H$^+$]=480 Calculated for C$_{28}$H$_{34}$ClN$_3$O$_2$=479.

11.5 N-(2-{1-[1-(4-chlorophenyl)cyclobutyl]-1,2,3,4-tetrahydro-9H-b-carbolin-9-yl}ethyl)propane-1-sulfonamide

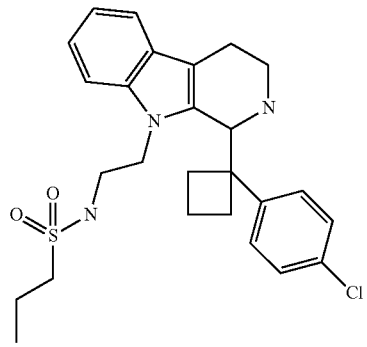 [SMILES: CCCS(=O)(=O)NCCn1c2c(c3ccccc31)CCNC2C1(c2ccc(Cl)cc2)CCC1]

tert-Butyl 9-(2-aminoethyl)-1-[1-(4-chlorophenyl)cyclobutyl]-1,3,4,9-tetrahydro-2H-b-carboline-2-carboxylate (90 mg, 0.187 mmol) was dissolved in pyridine (2 mL). Triethylamine (38 mg, 0.375 mmol) followed by propane-1-sulfonyl chloride (40 mg, 0.280 mmol) were added. The reaction mixture was stirred over night. The solvent was evaporated in vacuo. The residue was treated with dichloromethane (10 mL) and washed successively with saturated ammonium chloride solution (2×10 mL) and water (10 mL). The organic layer was dried (MgSO$_4$) and concentrated in vacuo. The crude intermediate was purified by flash chromatography (silica, dichloromethane, methanol). The obtained compound (58 mg, 0.099 mmol) was dissolved in dichloromethane (2 mL) and excess 5M isopropanolic hydrochloric acid was added. The reaction mixture was stirred over night at room temperature. The solvent was evaporated in vacuo. Yield: 35 mg (0.067 mmol, 68%).

ESI-MS [M+H$^+$]=486 Calculated for C$_{26}$H$_{32}$ClN$_3$O$_2$S=485.

Example 12

N-(2-(4-(1-(4-chlorophenyl)cyclobutyl)-4,5,6,7-tetrahydrothiazolo[4,5-c]pyridin-2-ylethyl)propane-1-sulfonamide hydrochloride

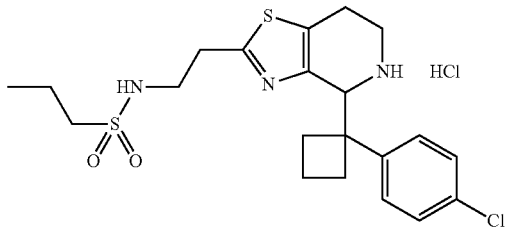

Chemical Formula: C$_{21}$H$_{28}$ClN$_3$O$_2$S$_2$
Exact Mass: 453,13

Step A

The crude intermediate 16 (30 mg) was dissolved in dichloromethane. DMAP (14 mg, 1.5 eq) and sulfonylchlorid (7 μl, 1.1 eq) were added. The reaction was stirred for 3 hours at room temperature. After complete conversation the reaction was diluted with dichloromethane and washed with HCl (0.1 N), water and brine, dried over MgSO$_4$ and evaporated. The residue was purified by PTLC to give the desired sulfonylamid.

Step B

The product of the step above was treated with HCl in isopropanol (1 ml, 5 N). After stirring for 2 hours at room temperature the reaction was complete. The solvents were evaporated and the product (2.1 mg, 6% over 2 steps) was dried in vacuo.

ESI-MS [M+H$^+$]=454 Calculated for C$_{21}$H$_{28}$ClN$_3$O$_2$S$_2$=455

Example 13

N-(2-(4-(1-(4-chlorophenyl)cyclobutyl)-4,5,6,7-tetrahydrothiazolo[4,5-c]pyridin-2-yl)ethyl)-1-methyl-1H-pyrazole-4-sulfonamide hydrochloride

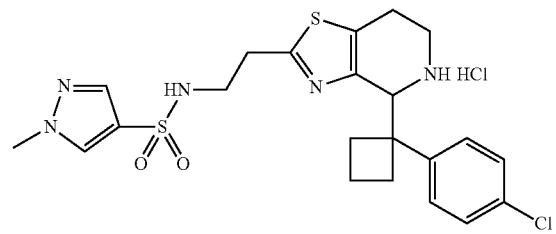

Chemical Formula: C$_{22}$H$_{26}$ClN$_5$O$_2$S$_2$
Exact Mass: 491,12

N-(2-(4-(1-(4-chlorophenyl)cyclobutyl)-4,5,6,7-tetrahydrothiazolo[4,5-c]pyridin-2-yl)ethyl)-1-methyl-1H-pyrazole-4-sulfonamide hydrochloride was prepared analogously to example 12 using 1-methyl-1H-pyrazole-4-sulfonyl chloride.

ESI-MS [M+H$^+$]=492 Calculated for C$_{22}$H$_{26}$ClN$_5$O$_2$S$_2$=491

Example 14

N-(2-(4-(1-(4-chlorophenyl)cyclobutyl)-4,5,6,7-tetrahydrothiazolo[4,5-c]pyridin-2-yl)ethyl)-1-methyl-1H-imidazole-4-sulfonamide hydrochloride

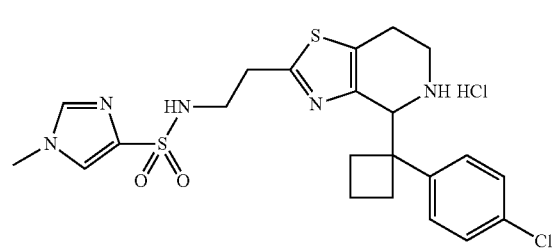

Chemical Formula: C$_{22}$H$_{26}$ClN$_5$O$_2$S$_2$
Exact Mass: 491,12

N-(2-(4-(1-(4-chlorophenyl)cyclobutyl)-4,5,6,7-tetrahydrothiazolo[4,5-c]pyridin-2-yl)ethyl)-1-methyl-1H-imidazole-4-sulfonamide hydrochloride was prepared analogously to example 12 using 1-methyl-1H-imidazole-4-sulfonyl chloride.

ESI-MS [M+H$^+$]=492 Calculated for C$_{22}$H$_{26}$ClN$_5$O$_2$S$_2$=491

Example 15

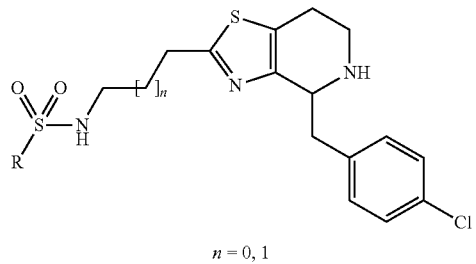

n = 0, 1

General Procedure
Step A

Preparation of 5-pyrrolidin-1-yl-3,4-dihydro-2H-pyridine-1-carboxylic acid tert-butyl

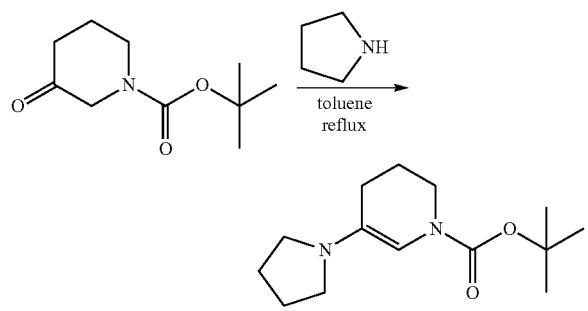

To a stirred solution of 3-oxo-piperidine-1-carboxylic acid tert-butyl ester (50, 0.25 mol) in anhydrous toluene (500 mL) was added pyrrolidine (26.6 g, 0.375 mol) in a round bottom flask filled with a Dean-Stark trap. After refluxing for 4 hrs, the mixture was concentrated under reduced pressure to give an orange oil, which was used directly in next step.

Step B

Preparation of 2-benzyl-3-oxo-piperidine-1-carboxylic acid tert-butyl ester

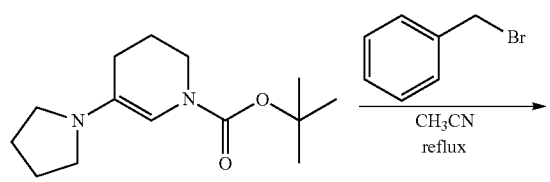

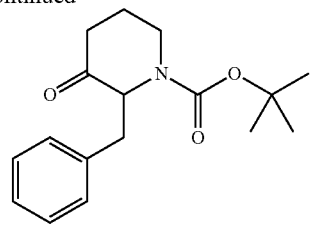

To a solution of crude 5-pyrrolidin-1-yl-3,4-dihydro-2H-pyridine-1-carboxylic acid tert-butyl ester (0.25 mol) in anhydrous CH$_3$CN (500 mL) was added benzyl bromide (33 mL, 0.275 mol) at 25° C. After refluxing for 16 hrs, the mixture was concentrated under reduced pressure, and then diluted with water, extracted with EtOAc (3×200 mL). The combined organic layer was washed with brine, dried over Na$_2$SO$_4$, concentrated and further purified by column chromatography on silica gel (PE:EtOAc=15:1~8:1) to afford 2-benzyl-3-oxo-piperidine-1-carboxylic acid tert-butyl ester (42 g, yield 58%, 2 steps) as a white solid.

Step C

Preparation of 2-benzyl-4-bromo-3-oxo-piperidine-1-carboxylic acid tert-butyl ester

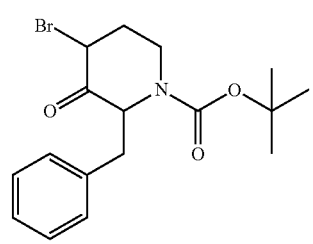

To a solution of 2-benzyl-3-oxo-piperidine-1-carboxylic acid tert-butyl ester (25.9 g, 0.09 mol) in CHCl$_3$ (200 mL) was added Br$_2$ (15.8 g, 0.099 mol, dissolved into 80 mL of CHCl$_3$) dropwise at 0° C. After the addition, the mixture was stirred at 25° C. for 2 hrs, and then it was filtered. The filtrate was washed with saturated NaHSO$_3$ and brine, dried over Na$_2$SO$_4$ and concentrated under reduced pressure to afford crude 2-benzyl-4-bromo-3-oxo-piperidine-1-carboxylic acid tert-butyl ester (18 g) as brown oil, which was used directly in the next step.

Step D

Preparation of 4-benzyl-2-ethyl-6,7-dihydro-4H-thiazolo[4,5-c]pyridine-5-carboxylic acid tert-butyl esters

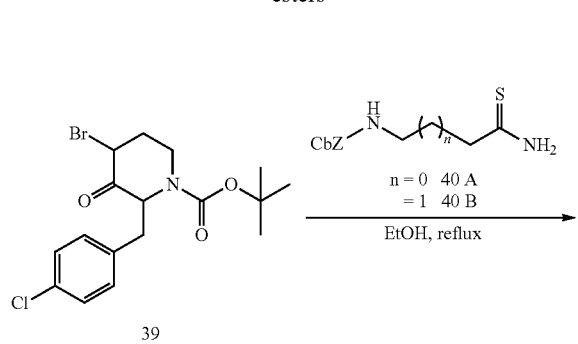

To a solution of 2-benzyl-3-oxo-piperidine-1-carboxylic acid tert-butyl ester in EtOH was added thioamide 40 A or 40 B at 25° C. After refluxing for 2 hrs, TLC indicated the completed conversion of starting material. The mixture was concentrated under reduced pressure to give a residue, which was used directly in next step.

Step E

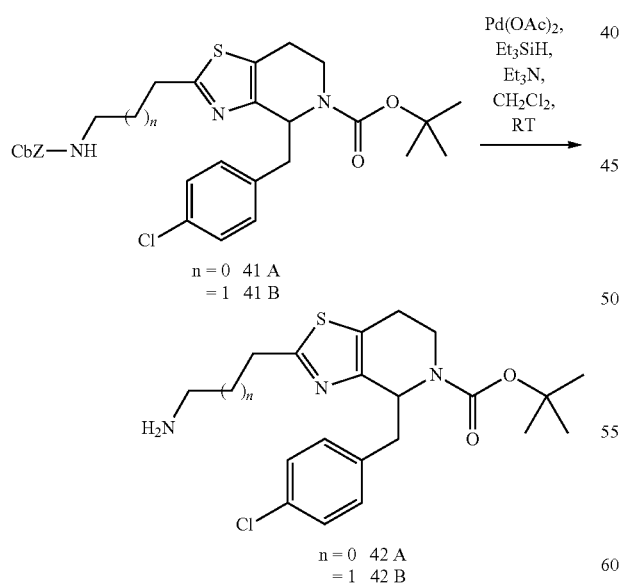

The protecting group was removed following standard protocol using a catalytic amount palladium and an excess of triethyl silane in the presence of triethyl amine in dichloro methane at room temperature yielding the desired product 42 A or 42 B in 84% yield.

Step F

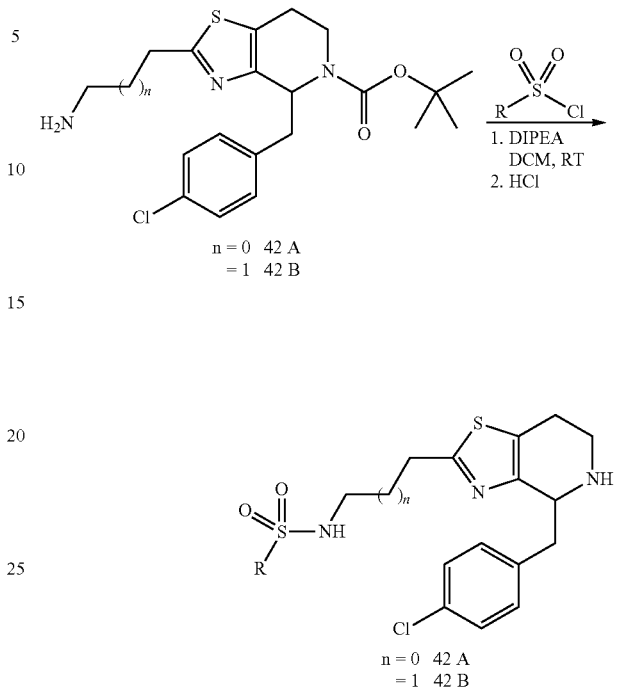

1 Equivalent of amine 42 A or 42 B was dissolved in CH$_2$Cl$_2$ and to this, 2 equivalents of DIEA in CH$_2$Cl$_2$ was added followed by 1 equivalent of sulfonyl chloride in CH$_2$Cl$_2$. The reaction was shaken at room temperature until completion. Any unreacted sulfonyl chloride can be scavenged by using a Si-amine cartridge (from SiliCycle). The reaction was dried down and the crude product was purified by RP-HPLC.

The product of the step above was treated with HCl in isopropanol (1 ml, 5 N). After stirring for 2 hours at room temperature the reaction was complete. The solvents were evaporated and the product was dried in vacuo.

The following compounds were obtained or can be obtained using the procedure described above.

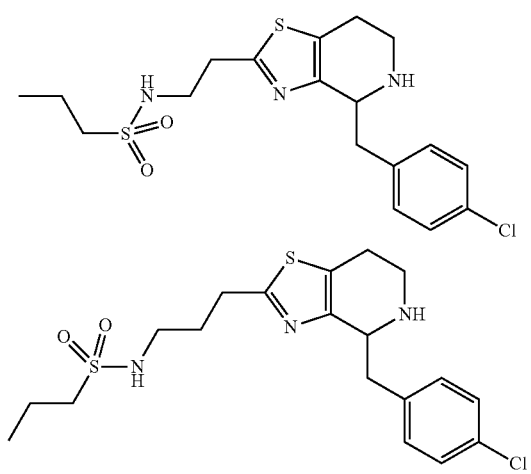

97
-continued
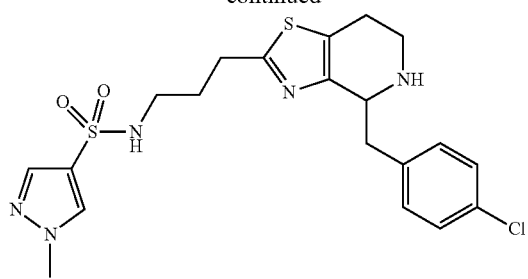
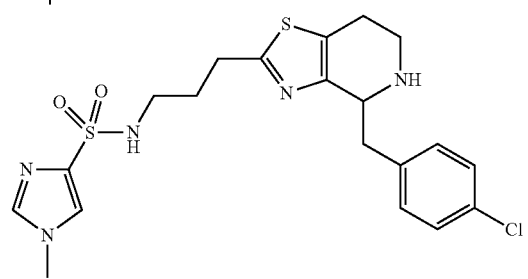
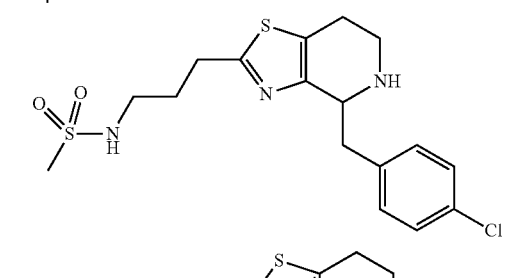
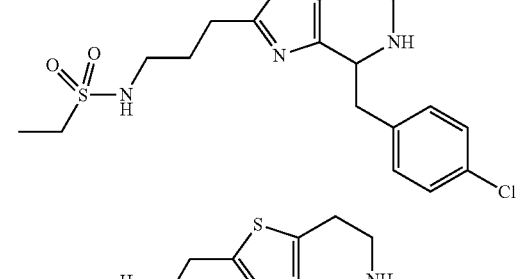
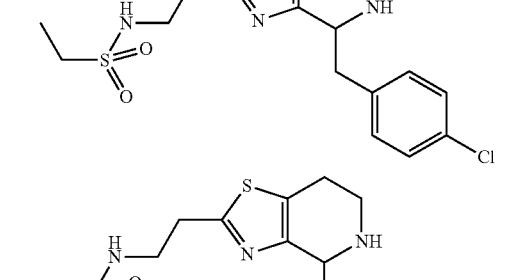
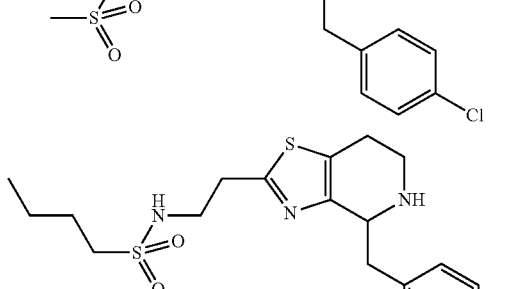
98
-continued
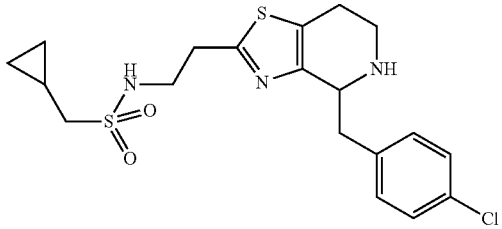
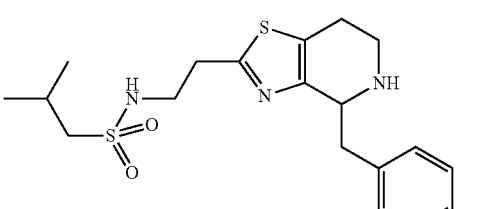
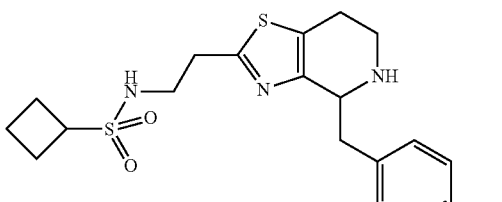
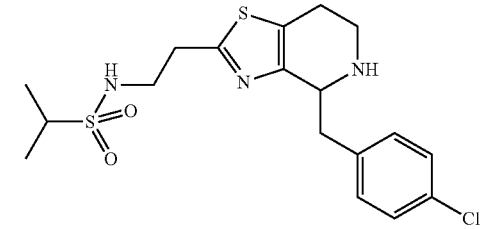
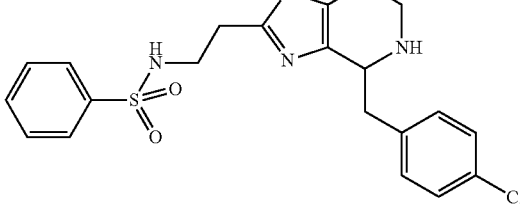
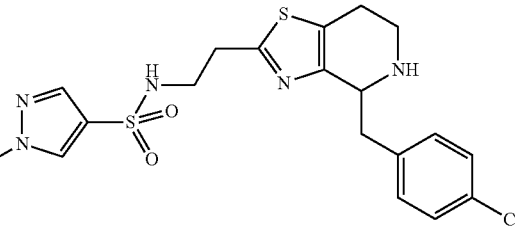
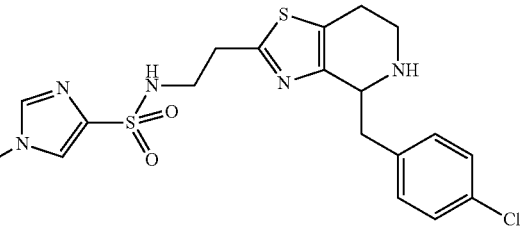

99
-continued
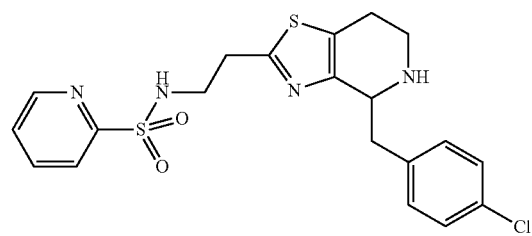
100
-continued
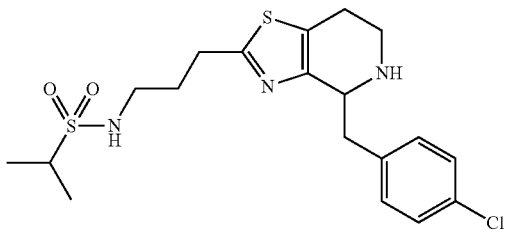
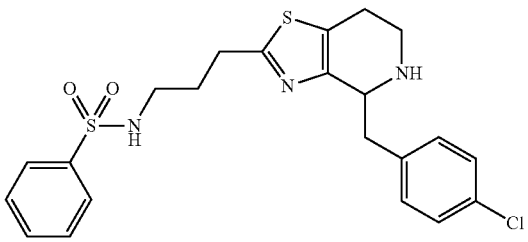
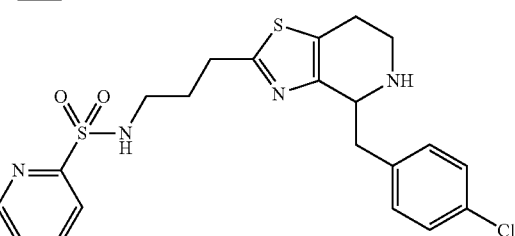
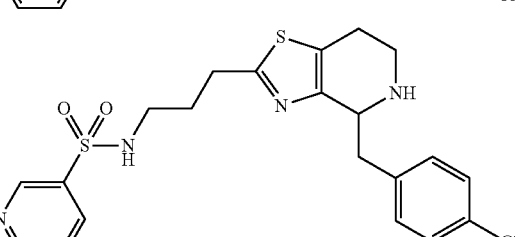
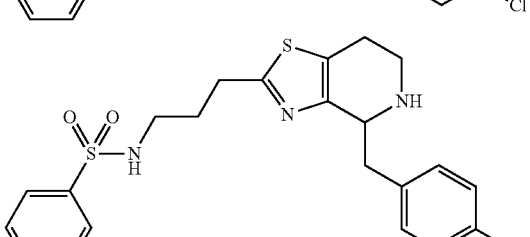
Example 16
Further compounds of the invention which were obtained or can be obtained using the procedures disclosed herein include the following:

101
-continued

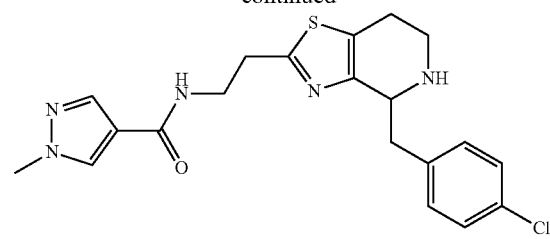

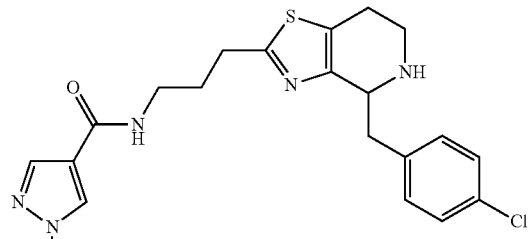

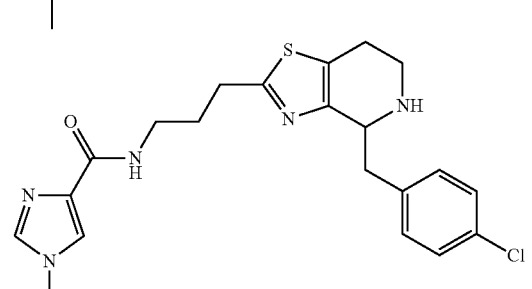

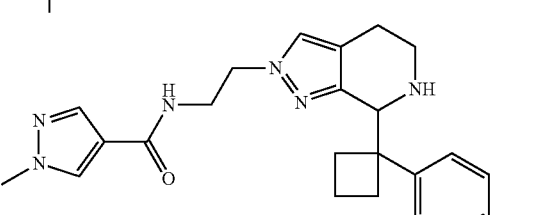

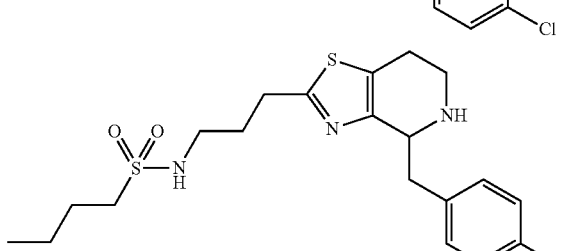

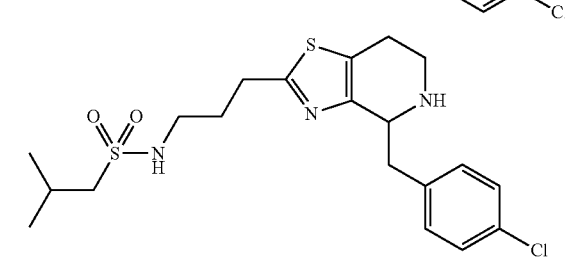

102
-continued

Biological Testing

1. [$^3$H]-Glycine uptake into recombinant CHO cells expressing human GlyT1: Human GlyT1c expressing recombinant hGlyT1c_5_CHO cells were plated at 20,000 cells per well in 96 well Cytostar-T scintillation microplates (Amersham Biosciences) and cultured to sub-confluency for 24 h. For glycine uptake assays the culture medium was aspirated and the cells were washed once with 100 μl HBSS (Gibco BRL, #14025-050) with 5 mM L-Alanine (Merck #1007). 80 μl HBSS buffer were added, followed by 10 μl inhibitor or vehicle (10% DMSO) and 10 μl [$^3$H]-glycine (TRK71, Amersham Biosciences) to a final concentration of 200 nM for initiation of glycine uptake. The plates were placed in a Wallac Microbeta (PerkinElmer) and continuously counted by solid phase scintillation spectrometry during up to 3 hours. Nonspecific uptake was determined in the presence of 10 µM Org24598. $IC_{50}$ calculations were made by four-parametric logistic nonlinear regression analysis (GraphPad Prism) using determinations within the range of linear increase of [$^3$H]-glycine incorporation between 60 and 120 min.

2. Radioligand binding assays using recombinant CHO cell membranes expressing human GlyT1:

Radioligand binding to human GlyT1c transporter-expressing membranes was carried out as described in Mezler et al., Molecular Pharmacology 74:1705-1715, 2008.

The following results were obtained with the compounds disclosed in the examples:

| Example | radioligand binding $K_{iapp}$[µmol] |
|---------|--------------------------------------|
| 6       | ≥10                                  |
| 7.1     | ≤1                                   |
| 7.2     | ≤10                                  |
| 7.3     | ≤1                                   |
| 7.4     | ≤1                                   |
| 8.1     | ≤1                                   |
| 8.2     | ≤1                                   |
| 8.3     | ≤1                                   |
| 8.4     | ≤1                                   |
| 8.5     | ≤1                                   |
| 9.1     | ≤1                                   |
| 9.2     | ≤10                                  |
| 9.3     | ≤1                                   |
| 9.4     | ≤1                                   |
| 9.5     | ≤1                                   |
| 9.6     | ≤1                                   |
| 9.7     | ≤1                                   |
| 9.8     | ≤1                                   |
| 9.9     | ≤1                                   |
| 9.10    | ≤1                                   |
| 9.11    | ≤1                                   |
| 9.12    | ≤1                                   |
| 10      | ≤1                                   |
| 11      | ≤1                                   |

We claim:

1. A heterocyclic compound of the formula (I)

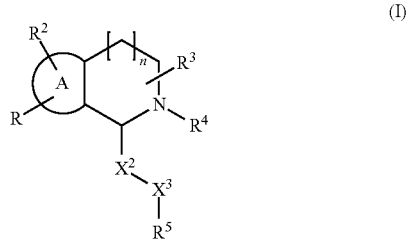
(I)

wherein

A is

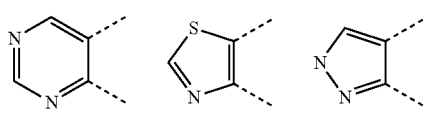

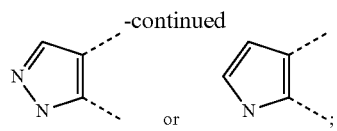
or

R is $R^1$—W—$A^1$—Q—Y—$A^2$—$X^1$—, wherein —Y—$A^2$—$X^1$— comprises at least atoms in the main chain;

$R^1$ is hydrogen, $C_1$-$C_6$-alkyl, $C_3$-$C_{12}$-cycloalkyl-$C_1$-$C_4$-alkyl, halogenated $C_1$-$C_6$-alkyl, hydroxy-$C_1$-$C_4$alkyl, $C_1$-$C_6$-alkoxy-$C_1$-$C_4$-alkyl, amino-$C_1$-$C_4$-alkyl, $C_1$-$C_6$-alkylamino-$C_1$-$C_4$-alkyl, di-$C_1$-$C_6$-alkylamino-$C_1$-$C_4$-alkyl, $C_1$-$C_6$-alkyloxycarbonylamino-$C_1$-$C_4$-alkyl, $C_1$-$C_6$-alkylaminocarbonylamino-$C_1$-$C_4$-alkyl, $C_1$-$C_6$-alkylsulfonylamino-$C_1$-$C_4$-alkyl, optionally substituted $C_6$-$C_{12}$-aryl-$C_1$-$C_4$-alkyl, optionally substituted $C_3$-$C_{12}$-heterocyclyl-$C_1$-$C_4$-alkyl, $C_3$-$C_{12}$-cycloalkyl, aminocarbonyl, $C_1$-$C_6$-alkylaminocarbonyl, $C_2$-$C_6$-alkenyl, optionally substituted $C_6$-$C_{12}$aryl, hydroxy, $C_1$-$C_6$-alkylamino, (halogenated $C_1$-$C_6$-alkyl)amino, di-$C_1$-$C_6$-alkylamino, di-(halogenated $C_1$-$C_6$-alkyl)amino, $C_1$-$C_6$-alkylcarbonylamino, (halogenated $C_1$-$C_6$alkyl)carbonylamino, $C_6$-$C_{12}$-arylcarbonylamino, $C_1$-$C_6$-alkylsulfonylamino, (halogenated $C_1$-$C_6$-alkyl)sulfonylamino, $C_6$-$C_1$-arylsulfonylamino or optionally substituted $C_3$-$C_{12}$-heterocyclyl;

W is —$NR^8$— or a bond;

$A^1$ is optionally substituted $C_1$-$C_4$-alkylene or a bond;

Q is —$S(O)_2$—, —$C(O)$— or a bond;

Y is —$NR^9$—or a bond;

$A^2$ is optionally substituted $C_1$-$C_4$-alkylene, $C_1$-$C_4$-alkylene-CO—, —CO—$C_1$-$C_4$-alkylene, $C_1$-$C_4$-alkylene-O—$C_1$-$C_4$-alkylene, $C_1$-$C_4$-alkylene-$NR^{10}$—$C_1$-$C_4$-alkylene, optionally substituted $C_2$-$C_4$-alkenylen, optionally substituted $C_2$-$C_4$-alkynylene, optionally substituted $C_6$-$C_{12}$-arylene, optionally substituted $C_6$-$C_1$-heteroarylene or a bond;

$X^1$ is —O—, —$NR^{11}$—, —S—, optionally substituted $C_1$-$C_4$-alkylene, optionally substituted $C_2$-$C_4$-alkenylen, optionally substituted $C_2$-$C_4$-alkynylene or a bond, with the proviso that if Q is a bond, W is —$NR^8$— or Y is —$NR^9$—;

$R^2$ is hydrogen, halogen, $C_1$-$C_6$-alkyl, halogenated $C_1$-$C_4$-alkyl, hydroxy-$C_1$-$C_4$-alkyl, —CN, $C_2$-$C_6$-alkenyl, $C_2$-$C_6$-alkynyl, optionally substituted $C_6$-$C_{12}$-aryl, hydroxy, $C_1$-$C_6$-alkoxy, halogenated $C_1$-$C_6$-alkoxy, $C_1$-$C_6$-alkoxycarbonyl, $C_2$-$C_6$-alkenyloxy, $C_6$-$C_{12}$-aryl-$C_1$-$C_4$-alkoxy, $C_1$-$C_6$-alkylcarbonyloxy, $C_1$-$C_6$-alkylthio, $C_1$-$C_6$-alkylsulfinyl, $C_1$-$C_6$-alkylsulfonyl, aminosulfonyl, amino, $C_1$-$C_6$-alkylamino, $C_2$-$C_6$-alkenylamino, nitro or optionally substituted $C_3$-$C_{12}$-heterocyclyl, or two radicals $R^2$ together with the ring atoms of A to which they are bound form an optionally substituted 5-or 6-membered ring;

$R^3$ is hydrogen, halogen, $C_1$-$C_6$-alkyl or $C_1$-$C_6$-alkoxy, or two radicals $R^3$ together with the carbon atom to which they are attached form a carbonyl group;

$R^4$ is hydrogen, $C_1$-$C_6$-alkyl, halogenated $C_1$-$C_4$-alkyl, hydroxy-$C_1$-$C_4$-alkyl, $C_1$-$C_6$-alkoxy-$C_1$-$C_4$-alkyl, amino-$C_1$-$C_4$-alkyl, $CH_2CN$, —CHO, $C_1$-$C_4$-alkylcarbonyl, (halogenated $C_1$-$C_4$-alkyl)carbonyl, $C_1$-$C_4$-alkoxycarbonyl, $C_6$-$C_{12}$-arylcarbonyl, $C_1$-$C_6$-alkylaminocarbonyl, $C_2$-$C_6$-alkenyl, —C(=NH)$NH_2$, —C(=NH)NHCN, $C_1$-$C_6$-alkylsulfonyl, $C_6$-$C_{12}$-arylsulfonyl, amino or $C_3$-$C_{12}$-heterocyclyl;

$X^2$ is —O—, —$NR^6$—, —S—, >$CR^{12a}R^{12b}$ or a bond;
$X^3$ is —O—, —$NR^7$—, —S—, >$CR^{13a}R^{13b}$ or a bond;
$R^5$ is optionally substituted $C_6$-$C_{12}$-aryl, optionally substituted $C_3$-$C_{12}$-cycloalkyl or optionally substituted $C_3$-$C_{12}$-heterocyclyl;
n is 0, 1, or 2;
$R^6$ is hydrogen or $C_1$-$C_6$-alkyl;
$R^7$ is hydrogen or $C_1$-$C_6$-alkyl;
$R^8$ is hydrogen or $C_1$-$C_6$-alkyl;
$R^9$ is hydrogen, $C_1$-$C_6$-alkyl, $C_3$-$C_{12}$-cycloalkyl, amino-$C_1$-$C_6$-alkyl, optionally substituted $C_6$-$C_{12}$-aryl-$C_1$-$C_4$-alkyl or $C_3$-$C_{12}$-heterocyclyl; or
$R^9$, $R^1$
together are $C_1$-$C_4$-alkylene; or
$R^9$ is $C_1$-$C_4$-alkylene that is bound to a carbon atom in $A^2$ and $A^2$ is $C_1$-$C_4$-alkylene or to a carbon atom in $X^1$ and $X^1$ is $C_1$-$C_4$-alkylene;
$R^{10}$ is hydrogen, $C_1$-$C_6$-alkyl or $C_1$-$C_6$-alkylsulfonyl;
$R^{11}$ is hydrogen or $C_1$-$C_6$-alkyl, or
$R^9$, $R^{11}$
together are $C_1$-$C_4$-alkylene,
$R^{12a}$ is hydrogen, optionally substituted $C_1$-$C_6$-alkyl, $C_1$-$C_6$-alkylamino-$C_1$-$C_4$-alkyl, di-$C_1$-$C_6$-alkylamino-$C_1$-$C_4$-alkyl, $C_3$-$C_{12}$-heterocyclyl-$C_1$-$C_6$-alkyl, optionally substituted $C_6$-$C_{12}$-aryl or hydroxy;
$R^{12b}$ is hydrogen or $C_1$-$C_6$-alkyl, or
$R^{12a}$, $R^{12b}$
together are carbonyl or optionally substituted $C_1$-$C_4$-alkylene, wherein one —$CH_2$— of $C_1$-$C_4$-alkylene may be replaced by an oxygen atom or —$NR^{14}$—;
$R^{13a}$ a is hydrogen, optionally substituted $C_1$-$C_6$-alkyl, $C_1$-$C_6$-alkylamino-$C_1$-$C_4$-alkyl, di-$C_1$-$C_6$-alkylamino-$C_1C_4$-alkyl, $C_3$-$C_{12}$-heterocyclyl-$C_1$-$C_6$-alkyl, optionally substituted $C_6$-$C_{12}$-aryl or hydroxy;
$R^{13b}$ is hydrogen or $C_1$-$C_6$-alkyl, or
$R^{13a}$, $R^{13b}$
together are carbonyl or optionally substituted $C_1$-$C_4$-alkylene, wherein one —$CH_2$— of $C_1$-$C_4$-alkylene may be replaced by an oxygen atom or —$NR^{15}$—;
$R^{14}$ is hydrogen or $C_1$-$C_6$-alkyl;
$R^{15}$ is hydrogen or $C_1$-$C_6$-alkyl; and
or a physiologically tolerated salt thereof.

2. The compound or physiologically tolerated salt thereof of claim 1, wherein $R^1$ is hydrogen, $C_1$-$C_6$-alkyl, $C_3$-$C_{12}$-cycloalkyl-$C_1$-$C_4$-alkyl, halogenated $C_1$-$C_6$-alkyl, $C_1$-$C_6$-alkoxy-$C_1$-$C_4$-alkyl, amino-$C_1$-$C_4$-alkyl, $C_1$-$C_6$-alkylamino-$C_1$-$C_4$-alkyl, di-$C_1$-$C_6$-alkylamino-$C_1$-$C_4$-alkyl, $C_1$-$C_6$-alkyloxycarbonylamino-$C_1$-$C_4$-alkyl, $C_1$-$C_6$-alkylaminocarbonylamino-$C_1$-$C_4$-alkyl, $C_6$-$C_{12}$-aryl-$C_1$-$C_4$-alkyl, $C_3$-$C_{12}$-cycloalkyl, $C_2$-$C_6$-alkenyl, optionally substituted $C_6$-$C_{12}$-aryl, hydroxy, $C_1$-$C_6$-alkylamino, (halogenated $C_1$-$C_6$-alkyl)amino, di-$C_1$-$C_6$-alkylamino or optionally substituted $C_3$-$C_{12}$-heterocyclyl.

3. The compound or physiologically tolerated salt thereof of claim 1, wherein $A^1$ is a bond, or $A^1$ is $C_1$-$C_4$alkylene and W is —$NR^8$—.

4. The compound or physiologically tolerated salt thereof of claim 1, wherein $A^2$ is optionally substituted $C_1$-$C_4$-alkylene, or $A^2$ is $C_6$-$C_{12}$-arylene selected from the group consisting of phen-1,4-ylene and phen-1,3-ylene, or $C_6$-$C_{12}$-heteroarylene selected from the group consisting of pyrid-2,5-ylene and pyrid-2,4-ylene.

5. The compound or physiologically tolerated salt thereof of claim 1, wherein $X^1$ is —O— or —$NR^{11}$, or $X^1$ is optionally substituted $C_1$-$C_4$-alkylene and $A^2$ is a bond, or $X^1$ is a bond.

6. The compound or physiologically tolerated salt thereof of claim 1, wherein —Y-$A^2$-$X^1$— is —$NR^9$—$C_1$-$C_4$-alkylene-.

7. The compound or physiologically tolerated salt thereof of claim 1, wherein $R^1$—W-$A^1$-Q-Y-$A^2$-$X^1$— is $R^1$—S(O)$_2$—NH-$A^2$-$X^1$—, $R^1$NH—S(O)$_2$-$A^2$-$X^1$—, $R^1$—C(O)—NH-$A^2$-$X^1$—, $R^1$—NH—C(O)-$A^2$-$X^1$— or $R^1$—NH-$A^2$-$X^1$—.

8. The compound or physiologically tolerated salt thereof of claim 1, having one of the formulae

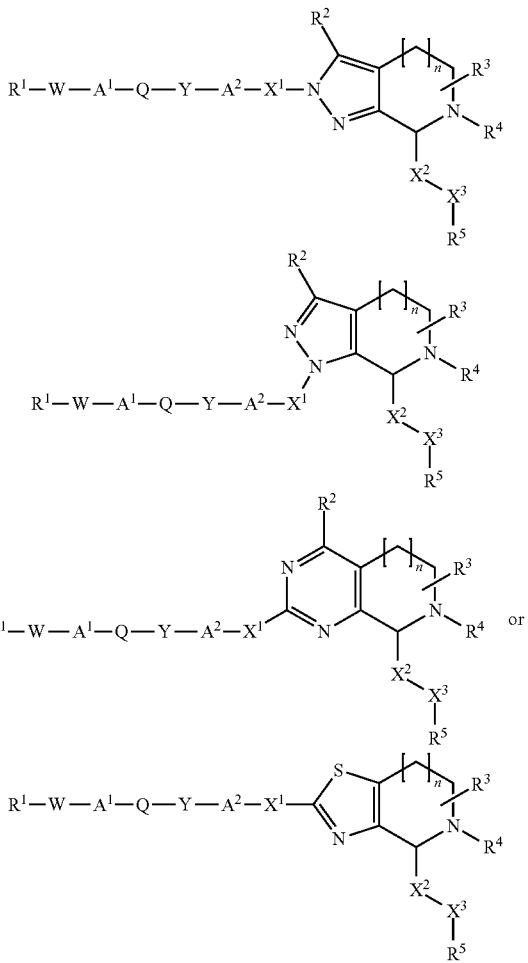

wherein $R^1$, W, $A^1$, Q, Y, $A^2$, $X^1$, $R^2$, $R^3$, $R^4$, $X^2$, $X^3$, $R^5$, n are as defined in claim 1.

9. The compound or physiologically tolerated salt thereof of claim 1, wherein $R^4$ is hydrogen, $C_1$-$C_6$-alkyl, halogenated $C_1$-$C_4$-alkyl, amino-$C_1$-$C_4$-alkyl, $CH_2CN$, $C_1$-$C_4$-alkylcarbonyl, (halogenated $C_1$-$C_4$-alkyl)carbonyl, $C_1$-$C_4$alkoxycarbonyl, —C(=NH)NH$_2$, —C(=NH)NHCN, $C_1$-$C_6$-alkylsulfonyl, amino or $C_3$-$C_{12}$-heterocyclyl.

10. The compound or physiologically tolerated salt thereof of claim 1, wherein $X^2$ is >$CR^{12a}R^{12b}$, and $X^3$ is a bond.

11. The compound or physiologically tolerated salt thereof of claim 1, wherein $R^{12a}$ is hydrogen and $R^{12b}$ is hydrogen, or $R^{12a}$ is $C_1$-$C_6$-alkyl and $R^{12b}$ is hydrogen or $C_1$-$C_6$-alkyl, or $R^{12a}$, $R^{12b}$ together are optionally substituted $C_1$-$C_4$-alkylene.

12. The compound or physiologically tolerated salt thereof of claim 1, wherein $R^5$ is optionally substituted aryl.

13. The compound or physiologically tolerated salt thereof of claim 12, having the formula

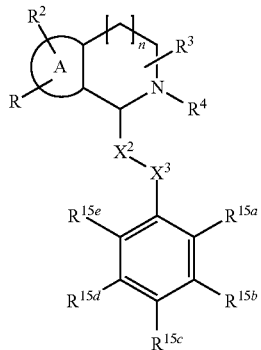

wherein A, R, $R^2$, $R^3$, $R^4$, $X^2$, $X^3$, n are as defined in claim 1; and $R^{15a}$, $R^{15b}$, $R^{15c}$, $R^{15d}$, $R^{15e}$, $R^{15f}$ independently are hydrogen, halogen, optionally substituted $C_1$-$C_6$-alkyl, halogenated $C_1$-$C_6$-alkyl, CN, hydroxy, $C_1$-$C_6$-alkoxy, amino, $C_1$-$C_6$-alkylamino, di-$C_1$-$C_6$-alkylamino or $C_3$-$C_{12}$-heterocyclyl.

14. The compound or physiologically tolerated salt thereof of claim 13, wherein $R^9$ is hydrogen.

15. The compound or physiologically tolerated salt thereof of claim 14, wherein n is 1.

16. The compound or physiologically tolerated salt thereof of claim 1, wherein

A is a ring selected from the group consisting of the following 5- or 6-membered heterocyclic rings:

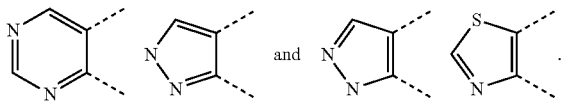

R is $R^1$—W-$A^1$-Q-Y-$A^2$-$X^1$—, wherein —Y-$A^2$-$X^1$— comprises at least 2 atoms in the main chain;

$R^1$ is hydrogen, $C_1$-$C_6$-alkyl, $C_3$-$C_{12}$-cycloalkyl-$C_1$-$C_4$-alkyl, halogenated $C_1$-$C_6$-alkyl, $C_3$-$C_{12}$-cycloalkyl, optionally substituted $C_6$-$C_{12}$-aryl, or optionally substituted $C_3$-$C_{12}$-heterocyclyl;

W is a bond;

$A^1$ is a bond;

Q is —S(O)$_2$—, —C(O)— or a bond;

Y is —$NR^9$— or a bond;

with the proviso that if Q is a bond, Y is —$NR^9$—;

$A^2$ is $C_1$-$C_4$-alkylene;

$X^1$ is a bond;

$R^2$ is hydrogen;

$R^3$ is hydrogen;

$R^4$ is hydrogen or $C_1$-$C_4$-alkoxycarbonyl;

$X^2$ is >$CR^{12a}R^{12b}$;

$X^3$ is a bond;

$R^5$ is optionally substituted phenyl;

$R^9$ is hydrogen or $C_3$-$C_{12}$-heterocyclyl; and $R^{12a}$ is hydrogen;

$R^{12b}$ is hydrogen, or $R^{12a}$, $R^{12b}$ together are optionally substituted $C_1$-$C_4$-alkylene.

17. A pharmaceutical composition comprising a carrier and the compound of claim 1.

18. A method for treating a neurologic or psychiatric disorder or pain in a mammalian patient in need thereof comprising administering to the patient a therapeutically effective amount of the compound or physiologically tolerated salt thereof of claim 1, wherein the neurologic or psychiatric disorder is selected from the group consisting of: glycinergic neurotransmission dysfunction, glutamatergic neurotransmission dysfunction, dementia, cognitive impairment, attention deficit disorder, hyperactivity, anxiety disorder, depression, a bipolar disorder, schizophrenia, and a psychotic disorder.

19. The compound or physiologically tolerated salt thereof of claim 1, selected from the group consisting of:

7-(1-Phenylcyclobutyl)-2-(2-(propylsulfonamido)ethyl)-4,5,6,7-tetrahydro-2H-pyrazolo[3,4-c]pyridine;

N-(Azetidin-3-yl)-N-(2-(7-(1-(4-chlorophenyl)cyclobutyl)-4,5,6,7-tetrahydro-2H-pyrazolo[3,4-c]pyridin-2-yl)ethyl)propane-1-sulfonamide;

(8-(1-(4-Chlorophenyl)cyclobutyl)-5,6,7,8-tetrahydropyrido[3,4-d]pyrimidin-2-yl)methanamine;

2-(7-(1-(4-Chlorophenyl)cyclobutyl)-4,5,6,7-tetrahydro-1H-pyrazolo[3,4-c]pyridin-1-yl)ethanamine;

2-(7-(1-(4-Chlorophenyl)cyclobutyl)-4,5,6,7-tetrahydro-2H-pyrazolo[3,4-c]pyridin-2-yl)ethanamine;

N-(2-(7-(1-(4-Chlorophenyl)cyclobutyl)-4,5,6,7-tetrahydro-1H-pyrazolo[3,4-c]pyridin-1-yl)ethyl)propane-1-sulfonamide;

N-(2-(7-(1-(4-Chlorophenyl)cyclobutyl)-4,5,6,7-tetrahydro-1H-pyrazolo[3,4-c]pyridin-1-yl)ethyl)-1-methyl-1H-pyrazole-4-sulfonamide;

N-(2-(7-(1-(4-Chlorophenyl)cyclobutyl)-4,5,6,7-tetrahydro-1H-pyrazolo[3,4-c]pyridin-1-yl)ethyl)-3-fluoropropane-1-sulfonamide;

N-(2-(7-(1-(4-Chlorophenyl)cyclobutyl)-4,5,6,7-tetrahydro-1H-pyrazolo[3,4-c]pyridin-1-yl)ethyl)-1-methyl-1H-imidazole-4-sulfonamide;

N-((8-(1-(4-Chlorophenyl)cyclobutyl)-5,6,7,8-tetrahydropyrido[3,4-d]pyrimidin-2-yl)methyl)propane-1-sulfonamide;

N-((8-(1-(4-Chlorophenyl)cyclobutyl)-5,6,7,8-tetrahydropyrido[3,4-d]pyrimidin-2-yl)methyl)-1-cyclopropylmethanesulfonamide;

N-((8-(1-(4-Chlorophenyl)cyclobutyl)-5,6,7,8-tetrahydropyrido[3,4-d]pyrimidin-2-yl)methyl)-1-methyl-1H-pyrazole-4-sulfonamide;

N-((8-(1-(4-Chlorophenyl)cyclobutyl)-5,6,7,8-tetrahydropyrido[3,4-d]pyrimidin-2-yl)methyl)-1-methyl-1H-imidazole-4-sulfonamide;

N-((8-(1-(4-Chlorophenyl)cyclobutyl)-5,6,7,8-tetrahydropyrido[3,4-d]pyrimidin-2-yl)methyl)-3-fluoropropane-1-sulfonamide;

N-(2-(7-(1-(4-Chlorophenyl)cyclobutyl)-4,5,6,7-tetrahydro-2H-pyrazolo[3,4-c]pyridin-2-yl)ethyl)propane-1-sulfonamide;

N-(2-(7-(1-(4-Chlorophenyl)cyclobutyl)-4,5,6,7-tetrahydro-2H-pyrazolo[3,4-c]pyridin-2-yl)ethyl)ethanesulfonamide;

N-(2-(7-(1-(4-Chlorophenyl)cyclobutyl)-4,5,6,7-tetrahydro-2H-pyrazolo[3,4-c]pyridin-2-yl)ethyl)methanesulfonamide;

N-(2-(7-(1-(4-Chlorophenyl)cyclobutyl)-4,5,6,7-tetrahydro-2H-pyrazolo[3,4-c]pyridin-2-yl)ethyl)benzenesulfonamide;

N-(2-(7-(1-(4-Chlorophenyl)cyclobutyl)-4,5,6,7-tetrahydro-2H-pyrazolo[3,4-c]pyridin-2-yl)ethyl)butane-1-sulfonamide;

N-(2-(7-(1-(4-Chlorophenyl)cyclobutyl)-4,5,6,7-tetrahydro-2H-pyrazolo[3,4-c]pyridin-2-yl)ethyl)-1-methyl-1H-pyrazole-4-sulfonamide;

N-(2-(7-(1-(4-Chlorophenyl)cyclobutyl)-4,5,6,7-tetrahydro-2H-pyrazolo[3,4-c]pyridin-2-yl)ethyl)-1-methyl-1H-imidazole-4-sulfonamide;

N-(2-(7-(1-(4-Chlorophenyl)cyclobutyl)-4,5,6,7-tetrahydro-2H-pyrazolo[3,4-c]pyridin-2-yl)ethyl)-3-fluoropropane-1-sulfonamide;

N-(2-(7-(1-(4-Chlorophenyl)cyclobutyl)-4,5,6,7-tetrahydro-2H-pyrazolo[3,4-c]pyridin-2-yl)ethyl)cyclobutanesulfonamide;

N-(2-(7-(1-(4-Chlorophenyl)cyclobutyl)-4,5,6,7-tetrahydro-2H-pyrazolo[3,4-c]pyridin-2-yl)ethyl)-1-cyclopropylmethanesulfonamide;

N-(2-(7-(1-(4-chlorophenyl)cyclobutyl)-4,5,6,7-tetrahydro-2H-pyrazolo[3,4-c]pyridin-2-yl)ethyl)-2-methylpropane-1-sulfonamide;

N-(2-(7-(1-(4-Chlorophenyl)cyclobutyl)-4,5,6,7-tetrahydro-2H-pyrazolo[3,4-c]pyridin-2-yl)ethyl)pyridine-3-sulfonamide;

N-(2-(7-(1-(4-chlorophenyl)cyclobutyl)-4,5,6,7-tetrahydro-2H-pyrazolo[3,4-c]pyridin-2-yl)ethyl)-N-methylpropane-1-sulfonamide;

N-(2-{1-[1-(4-Chlorophenyl)cyclobutyl]-1,2,3,4-tetrahydro-9H-b-carbolin-9-yl}ethyl)propane-1-sulfonamide;

N-(2-(4-(1-(4-chlorophenyl)cyclobutyl)-4,5,6,7-tetrahydrothiazolo[4,5-c]pyridin-2-yl)ethyl)propane-1-sulfonamide;

N-(2-(4-(1-(4-chlorophenyl)cyclobutyl)-4,5,6,7-tetrahydrothiazolo[4,5-c]pyridin-2-yl)ethyl)-1-methyl-1H-pyrazole-4-sulfonamide;

N-(2-(4-(1-(4-chlorophenyl)cyclobutyl)-4,5,6,7-tetrahydrothiazolo[4,5-c]pyridin-2-yl)ethyl)-1-methyl-1H-imidazole-4-sulfonamide;

N-(2-(4-(4-chlorobenzyl)-4,5,6,7-tetrahydrothiazolo[4,5-c]pyridin-2-yl)ethyl)propane-1-sulfonamide;

N-(3-(4-(4-chlorobenzyl)-4,5,6,7-tetrahydrothiazolo[4,5-c]pyridin-2-yl) propyl)propane-1-sulfonamide;

N-(3-(4-(4-chlorobenzyl)-4,5,6,7-tetrahydrothiazolo[4,5-c]pyridin-2-yl)propyl)-1-methyl-1H-pyrazole-4-sulfonamide;

N-(3-(4-(4-chlorobenzyl)-4,5,6,7-tetrahydrothiazolo[4,5-c]pyridin-2-yl) propyl)-1-methyl-1H-imidazole-4-sulfonamide;

N-(3-(4-(4-chlorobenzyl)-4,5,6,7-tetrahydrothiazolo[4,5-c]pyridin-2-yl)propyl)methanesulfonamide;

N-(3-(4-(4-chlorobenzyl)-4,5,6,7-tetrahydrothiazolo[4,5-c]pyridin-2-yl)propyl)ethanesulfonamide;

N-(2-(4-(4-chlorobenzyl)-4,5,6,7-tetrahydrothiazolo[4,5-c]pyridin-2-yl)ethyl)ethanesulfonamide;

N-(2-(4-(4-chlorobenzyl)-4,5,6,7-tetrahydrothiazolo[4,5-c]pyridin-2-yl)ethyl)methanesulfonamide;

N-(2-(4-(4-chlorobenzyl)-4,5,6,7-tetrahydrothiazolo[4,5-c]pyridin-2-yl)ethyl)butane-1-sulfonamide;

N-(2-(4-(4-chlorobenzyl)-4,5,6,7-tetrahydrothiazolo[4,5-c]pyridin-2-yl)ethyl)-1-cyclopropylmethanesulfonamide;

N-(2-(4-(4-chlorobenzyl)-4,5,6,7-tetrahydrothiazolo[4,5-c]pyridin-2-yl)ethyl)-2-methylpropane-1-sulfonamide;

N-(2-(4-(4-chlorobenzyl)-4,5,6,7-tetrahydrothiazolo[4,5-c]pyridin-2-yl)ethyl)cyclobutanesulfonamide;

N-(2-(4-(4-chlorobenzyl)-4,5,6,7-tetrahydrothiazolo[4,5-c]pyridin-2-yl)ethyl)propane-2-sulfonamide;

N-(2-(4-(4-chlorobenzyl)-4,5,6,7-tetrahydrothiazolo[4,5-c]pyridin-2-yl)ethyl)benzenesulfonamide;

N-(2-(4-(4-chlorobenzyl)-4,5,6,7-tetrahydrothiazolo[4,5-c]pyridin-2-yl)ethyl)-1-methyl-1H-pyrazole-4-sulfonamide;

N-(2-(4-(4-chlorobenzyl)-4,5,6,7-tetrahydrothiazolo[4,5-c]pyridin-2-yl)ethyl)-1-methyl-1H-imidazole-4-sulfonamide;

N-(2-(4-(4-chlorobenzyl)-4,5,6,7-tetrahydrothiazolo[4,5-c]pyridin-2-yl)ethyl)pyridine-2-sulfonamide;

N-(2-(4-(4-chlorobenzyl)-4,5,6,7-tetrahydrothiazolo[4,5-c]pyridin-2-yl)ethyl)pyridine-3-sulfonamide;

N-(2-(4-(4-chlorobenzyl)-4,5,6,7-tetrahydrothiazolo[4,5-c]pyridin-2-yl)ethyl)pyridine-4-sulfonamide;

N-(3-(4-(4-chlorobenzyl)-4,5,6,7-tetrahydrothiazolo[4,5-c]pyridin-2-yl)propyl)butane-1-sulfonamide;

N-(3-(4-(4-chlorobenzyl)-4,5,6,7-tetrahydrothiazolo[4,5-c]pyridin-2-yl)propyl)-2-methylpropane-1-sulfonamide;

N-(3-(4-(4-chlorobenzyl)-4,5,6,7-tetrahydrothiazolo[4,5-c]pyridin-2-yl)propyl)-1-cyclopropylmethanesulfonamide;

N-(3-(4-(4-chlorobenzyl)-4,5,6,7-tetrahydrothiazolo[4,5-c]pyridin-2-yl)propyl)cyclobutanesulfonamide;

N-(3-(4-(4-chlorobenzyl)-4,5,6,7-tetrahydrothiazolo[4,5-c]pyridin-2-yl)propyl)propane-2-sulfonamide;

N-(3-(4-(4-chlorobenzyl)-4,5,6,7-tetrahydrothiazolo[4,5-c]pyridin-2-yl)propyl)benzenesulfonamide;

N-(3-(4-(4-chlorobenzyl)-4,5,6,7-tetrahydrothiazolo[4,5-c]pyridin-2-yl)propyl)pyridine-2-sulfonamide;

N-(3-(4-(4-chlorobenzyl)-4,5,6,7-tetrahydrothiazolo[4,5-c]pyridin-2-yl)propyl)pyridine-3-sulfonamide;

N-(3-(4-(4-chlorobenzyl)-4,5,6,7-tetrahydrothiazolo[4,5-c]pyridin-2-yl)propyl)pyridine-4-sulfonamide;

N-(2-(4-(4-chlorobenzyl)-4,5,6,7-tetrahydrothiazolo[4,5-c]pyridin-2-yl)ethyl)-1-methyl-1H-imidazole-4-carboxamide;

N-(2-(4-(4-chlorobenzyl)-4,5,6,7-tetrahydrothiazolo[4,5-c]pyridin-2-yl)ethyl)-1-methyl-1H-pyrazole-4-carboxamide;

N-(3-(4-(4-chlorobenzyl)-4,5,6,7-tetrahydrothiazolo[4,5-c]pyridin-2-yl)propyl)-1-methyl-1H-pyrazole-4-carboxamide;

N-(3-(4-(4-chlorobenzyl)-4,5,6,7-tetrahydrothiazolo[4,5-c]pyridin-2-yl)propyl)-1-methyl-1H-imidazole-4-carboxamide; and N-(2-(4-(4-chlorobenzyl)-4,5,6,7-tetrahydrothiazolo[4,5-c]pyridin-2-yl)ethyl)-1-methyl-1H-pyrazole-4-carboxamide.

* * * * *

UNITED STATES PATENT AND TRADEMARK OFFICE
CERTIFICATE OF CORRECTION

| | | |
|---|---|---|
| PATENT NO. | : 8,642,587 B2 | Page 1 of 1 |
| APPLICATION NO. | : 12/706321 | |
| DATED | : February 4, 2014 | |
| INVENTOR(S) | : Lange et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 373 days.

Signed and Sealed this
Fourteenth Day of July, 2015

Michelle K. Lee
*Director of the United States Patent and Trademark Office*